United States Patent
Koike et al.

(10) Patent No.: US 9,624,184 B2
(45) Date of Patent: Apr. 18, 2017

(54) HETEROCYCLIC COMPOUND

(71) Applicant: TAKEDA PHARMACEUTICAL COMPANY LIMITED, Osaka (JP)

(72) Inventors: Tatsuki Koike, Kanagawa (JP); Masato Yoshikawa, Kanagawa (JP); Izumi Nomura, Kanagawa (JP); Yoshiteru Ito, Kanagawa (JP); Eiji Kimura, Kanagawa (JP); Haruhi Ando, Kanagawa (JP); Tomoaki Hasui, Kanagawa (JP); Toshiya Nishi, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/781,665

(22) PCT Filed: Apr. 3, 2014

(86) PCT No.: PCT/JP2014/059893
§ 371 (c)(1),
(2) Date: Oct. 1, 2015

(87) PCT Pub. No.: WO2014/163162
PCT Pub. Date: Oct. 9, 2014

(65) Prior Publication Data
US 2016/0052897 A1    Feb. 25, 2016

(30) Foreign Application Priority Data

Apr. 4, 2013   (JP) ................. 2013-079024

(51) Int. Cl.
| | |
|---|---|
| C07D 413/10 | (2006.01) |
| C07D 491/08 | (2006.01) |
| C07D 413/12 | (2006.01) |
| C07D 413/14 | (2006.01) |
| C07D 263/32 | (2006.01) |
| C07D 413/04 | (2006.01) |

(52) U.S. Cl.
CPC ......... *C07D 263/32* (2013.01); *C07D 413/04* (2013.01); *C07D 413/10* (2013.01); *C07D 413/12* (2013.01); *C07D 413/14* (2013.01); *C07D 491/08* (2013.01)

(58) Field of Classification Search
CPC .. C07D 491/08; C07D 413/14; C07D 413/10; C07D 263/32; C07D 413/04; C07D 413/12
USPC ...................................................... 546/268.1
See application file for complete search history.

(56) References Cited

U.S. PATENT DOCUMENTS

| | | | |
|---|---|---|---|
| 9,296,746 B2* | 3/2016 | Koike ................. | C07D 471/04 |
| 2006/0100196 A1* | 5/2006 | Gailunas ............. | C07D 207/26 |
| | | | 514/211.15 |

| | | |
|---|---|---|
| 2006/0276433 A1 | 12/2006 | Kawagoe et al. |
| 2008/0132477 A1 | 6/2008 | Betschart et al. |
| 2008/0146573 A1 | 6/2008 | Gant et al. |
| 2009/0111848 A1 | 4/2009 | Anglada et al. |
| 2010/0063040 A1 | 3/2010 | Kugimiya |
| 2010/0069638 A1 | 3/2010 | Kugimiya et al. |
| 2012/0095024 A1 | 4/2012 | Alonson et al. |
| 2013/0090341 A1 | 4/2013 | Koike et al. |
| 2013/0331401 A1 | 12/2013 | Anglada et al. |
| 2013/0331610 A1 | 12/2013 | Anglada et al. |
| 2014/0088118 A1 | 3/2014 | Koike et al. |
| 2014/0088146 A1 | 3/2014 | Koike et al. |
| 2014/0228373 A1 | 8/2014 | Koike et al. |
| 2015/0158833 A1 | 6/2015 | Kugimiya et al. |
| 2015/0266872 A1 | 9/2015 | Koike et al. |
| 2015/0315209 A1 | 11/2015 | Koike et al. |

FOREIGN PATENT DOCUMENTS

| | | |
|---|---|---|
| JP | 2010-110400 | 5/2010 |
| JP | 2010-248183 | 11/2010 |
| WO | 2004/087641 | 10/2004 |
| WO | 2006/074950 | 7/2006 |
| WO | 2007/037187 | 4/2007 |
| WO | 2008/070619 | 6/2008 |
| WO | 2010/075869 | 7/2010 |

(Continued)

OTHER PUBLICATIONS

Vance; Disease Models & Mechanisms 2012 5, 746-755.*
Leoni; Chemistry and Physics of Lipids 2011, 164, 515-524.*
Iwanowicz; Bioorganic & Medicinal Chemistry Letters 13 (2003) 2059-2063.*
International Search Report issued Jul. 8, 2014 in International Application No. PCT/JP2014/059893.
Hung-Kai Chen et al., "Small Molecule Structure Correctors Abolish Detrimental Effects of Apolipoprotein E4 in Cultured Neurons", Journal of Biological Chemistry, Feb. 17, 2012, vol. 287, No. 8. pp. 5253-5266.

(Continued)

*Primary Examiner* — Noble Jarrell
*Assistant Examiner* — Daniel Carcanague
(74) *Attorney, Agent, or Firm* — Wenderoth, Lind & Ponack, L.L.P.

(57) ABSTRACT

The present invention relates to a compound represented by the formula (I), which is useful as an agent for the prophylaxis or treatment of epilepsy, neurodegenerative disease and the like. In the formula (I), each symbol is as defined in the specification.

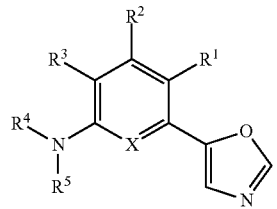

(I)

10 Claims, No Drawings

(56) References Cited

FOREIGN PATENT DOCUMENTS

| WO | 2010/076033 | | 7/2010 |
|----|----|----|----|
| WO | 2010/110400 | | 9/2010 |
| WO | 2010/126002 | | 11/2010 |
| WO | 2011/097491 | | 8/2011 |
| WO | 2013/054822 | | 4/2013 |
| WO | 2013/059648 | | 4/2013 |
| WO | 2014/061676 | | 4/2014 |
| WO | WO2014052566 | * | 4/2014 |
| WO | 2014/092100 | | 6/2014 |
| WO | WO2014186313 | * | 11/2014 |
| WO | WO2015010297 | * | 1/2015 |

OTHER PUBLICATIONS

Supplementary European Search Report issued Oct. 12, 2016 in corresponding EP 14 77 9878.

* cited by examiner

SEQUENCE LISTING

<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: PCR primer

<400> SEQUENCE: 1
gccccggagc catgagcccc gggctg      26

<210> SEQ ID NO 2
<211> LENGTH: 26
<212> TYPE: DNA
<213> ORGANISM: Artificial
<220> FEATURE:
<223> OTHER INFORMATION: PCR primer

<400> SEQUENCE: 2
gtcctgcctg gaggccccct cagcag      26

HETEROCYCLIC COMPOUND

TECHNICAL FIELD

The present invention relates to a heterocyclic compound having a cholesterol 24-hydroxylase (in the present specification, sometimes to be abbreviated as "CH24H") inhibitory action, a pharmaceutical composition comprising same, and the like.

BACKGROUND OF THE INVENTION

Alzheimer's disease is a progressive neurodegenerative disease characterized by the deposition of amyloid β protein (Aβ), accumulation of phosphorylated tau in a nerve cell (neurofibrillary tangle), and nerve cell death. In recent years, the number of patients with Alzheimer's disease is increasing because of aging, but an effective treatment method has not been developed as yet. The therapeutic drugs for Alzheimer's disease which are currently used in the medical practice are mainly acetylcholinesterase (AchE) inhibitors. While AchE inhibitors is confirmed to provide a certain level of usefulness, since they are used with the aim of supplementing decreased acetylcholine, the treatment with AchE inhibitor is merely a symptomatic therapy. Thus, the prompt development of a basic remedy and prophylactic drug has been strongly desired.

It has been clarified that the presence of allele ε4 of apolipoprotein E (ApoE) controlling the cholesterol metabolism is a strong risk factor of Alzheimer's disease [non-patent document 1: Science, vol. 261, 921-923, 1993]. After this finding, the correlation between plural gene polymorphisms playing a role in the expression of protein controlling the cholesterol metabolism and the onset frequency of Alzheimer's disease has been shown, suggesting the correlation between the cholesterol metabolism and Alzheimer's disease [non-patent document 2: Neurobiol. Aging, vol. 24, 421-426, 2003, non-patent document 3: Mol. Psychiatry, vol. 8, 635-638, 2003]. Moreover, it has been reported that Cyp46 (same as "cholesterol 24-hydroxylase (CH24H)"), which is cholesterol oxidase specifically expressed in the brain, is a risk factor of Alzheimer's disease [non-patent document 4: Neurosci. Lett., vol. 328, pages 9-12, 2002]. Furthermore, it has also been reported that Cyp46 (CH24H) is expressed in periphery of deposited amyloid in Alzheimer's disease patients [non-patent document 5: J. Biol. Chem., vol. 279, pages 34674-34681, 2004], 24S-hydroxycholesterol (24-HC), which is a metabolite thereof, increases in the brain spinal cord fluid (CSF) of Alzheimer's disease patients [non-patent document 6: Neurosci. Lett., vol. 324, pages 83-85, 2002, non-patent document 7: Neurosci. Lett., vol. 397, pages 83-87, 2006], 24-HC induces cell death of SH-SY5Y cell, which is a human neuroblast line [non-patent document 8: Brain Res., vol. 818, pages 171-175, 1999], and rats in which 24-EC was injected into the lateral cerebral ventricle showed impaired short-term memory, which is commonly observed in Alzheimer's disease, suggesting that hippocampal neurons were damaged by 24-HC [non-patent document 9: Neuroscience, vol. 164, pages 398-403, 2009]. These findings suggest that Cyp46 (CH24H) is deeply involved in the pathology of Alzheimer's disease. Therefore, a compound that inhibits the Cyp46 (CH24H) activity (i.e., Cyp46 (CH24H) inhibitor) suppresses neuronal cell death, increase in Aβ, intracerebral inflammation and the like observed in Alzheimer's disease, by decreasing intracerebral 24-HC, and is promising as a therapeutic or prophylactic drug showing not only an improvement of symptoms but also a suppression of progression. Moreover, it has been reported that an AchE inhibitor clinically used as a therapeutic drug for Alzheimer's disease shows an improvement effect on memory disorders induced by Aβ in mouse [non-patent document 10: British Journal of Pharmacology, vol. 149, pages 998-1012, 2006]. Thus, a Cyp46 (CH24H) inhibitor showing an improvement effect for memory disorders in Aβ overexpression animal model (APP transgenic mouse, APP/PS1 double transgenic mouse, etc.) is promising as a therapeutic drug for Alzheimer's disease.

As a concept of the preclinical stage of Alzheimer's disease, a mild cognitive impairment has been proposed, and about half of those having this disorder is said to progress into the Alzheimer's disease in the future. In recent years, it has been reported that 24-HC increases not only in patients with Alzheimer's disease but also in CSF of patients with mild cognitive impairment [non-patent document 7: Neurosci. Lett., vol. 397, pages 83-87, 2006]. This finding suggests that Cyp46 (CH24H) is involved in the pathology of mild cognitive impairment, and therefore, a Cyp46 (CH24H) inhibitor is promising as a new therapeutic drug for Alzheimer's disease or a prophylactic drug for the progression into the Alzheimer's disease.

In recent years, moreover, it has been reported that 24-HC in the blood increases before expression of the symptom in an autoimmune encephalomyelitis model, which is an animal model of multiple sclerosis which is one of the demyelination diseases in the central nervous system [non-patent document 11: J. Neurosci. Res., vol. 85, pages 1499-1505, 2007]. Multiple sclerosis is often developed in younger people of about 30 years old, and scarcely developed in the elderly of 60 years or older. It has also been reported that 24-HC in the blood increases in multiple sclerosis patients aged from 21 to 50 [non-patent document 12: Neurosci. Lett., vol. 331, pages 163-166, 2002]. These findings suggest that Cyp46 (CH24H) is involved in the pathology of multiple sclerosis, and therefore, a Cyp46 (CH24H) inhibitor is promising as a new therapeutic or prophylactic drug for multiple sclerosis.

Traumatic brain injury (also referred to as TBI in the present specification) is a condition having an extremely harmful influence on the personal health, for which no effective cure has been established. In the repair process following tissue damage by TBI, reconstruction of neuronal cell membrane and distribution of intracerebral cholesterol along with the growth of glial cell are suggested to be activated [non-patent document 13: Proc. Natl. Acad. Sci. USA, vol. 102, pages 8333-8338, 2005]. In a rat TBI model, an enhanced expression of Cyp46 (CH24H) after trauma has been reported [non-patent document 14: J. Neurotrauma, pages 1087-1098, 2008]. Moreover, it has also been reported that 24-HC is injurious to neuronal cells [non-patent document 8: Brain Res., vol. 818, pages 171-175, 1999]. Therefore, a Cyp46 (CH24H) inhibitor is promising as a new therapeutic or prophylactic drug for TBI.

As a pathological significance of 24-HC in neurodegenerative diseases, an inflammatory gene expression-enhancing action in neuronal cells has been reported [non-patent document 15: NeuroReport, vol. 16, pages 909-913, 2005]. In addition, it is suggested that an intracerebral inflammation reaction accompanied by activation of glial cell is a pathological change characteristic of neurodegenerative diseases [non-patent document 16: Glia, vol. 50, pages 427-434, 2005]. In recent years, an effectiveness of therapy by suppression of intracerebral inflammation has also been reported for neurodegenerative diseases such as Huntington's disease, Parkinson's disease and amyotrophic lateral sclerosis and the like [non-patent document 17: Mol. Neurodegeneration, vol. 4, pages 47-59, 2009]. Therefore, suppression of intracerebral inflammation via decreasing 24-HC by the inhibition of Cyp46 (CH24H) is promising as a new therapeutic or prophylactic drug for neurodegenerative diseases such as Huntington's disease, Parkinson's disease, cerebral infarction, glaucoma, amyotrophic lateral sclerosis and the like.

Glaucoma is the main cause of blindness, and is considered to be a serious social problem. However, there is no effective cure of a normal intraocular pressure type-visual field constriction, which is the major symptom of the disease. In recent years, it has been reported that gene polymorphisms of Cyp46 (CH24H) associated with high value of 24-HC in blood is related to the risk of the onset of glaucoma [non-patent document 18: Invest. Ophthalmol. Vis. Sci., vol. 50, pages 5712-5717, 2009]. Thus, a Cyp46 (CH24H) inhibitor is promising as a therapeutic or prophylactic drug for glaucoma.

Spasm is a disorder that convulsively occurs with abnormal electrical excitation of neuronal cell in the brain. Spasm is one of the characteristic clinical findings of Alzheimer's disease [Non-Patent Document 19: Epilepsia, vol. 47, pages 867-872, 2006], and the relationship between epilepsy and onset of Alzheimer's disease has been indicated [Non-Patent Document 20: Epilepsia, vol. 52, Supplement 1, pages 39-46, 2011]. It has been reported that spasm occurs with high frequency in APP/PS1 double transgenic mouse which is one of the Alzheimer's disease models due to Aβ overexpression [non-patent document 21: J. Neurosci., vol. 29, pages 3453-3462, 2012]. Furthermore, since hippocampus astrocytes induce the expression of Cyp46 (CH24H) in a kainic acid lesion rat model, which is one of the epilepsy models, the relationship between this enzyme and pathology of epilepsy has been indicated [Non-Patent Document 22: J. Neurol., vol. 65, pages 652-663, 2006]. It has been reported that a therapeutic drug for spasm, carbamazepine, shows an improving effect on short-term memory in Y-maze test in an epileptic spasm mouse model [Non-Patent Document 23: J. Neurol. Neurosurg. Psychiatry, vol. 48, pages 459-468, 1985]. Therefore, a CH24H inhibitor, which shows an improving effect on short-term memory in a model animal showing a spasm symptom, is promising as a novel therapeutic drug or prophylaxis drug for spasm, epilepsy, and the like.

Since schizophrenia shows a variety of psychological symptoms such as hallucination, delusion, excitation, manic-depressive state and the like, therapeutic drugs therefor have been developed with various approaches. In recent years, it has been pointed out that changes in the cholesterol metabolism are involved in the abnormality of neural activity seen in schizophrenia [non-patent document 24: J. Psychiatry Neurosci., vol. 36, pages 47-55, 2011]. Since cytotoxic factors such as oxidative stress also contribute to the pathology of schizophrenia, neuronal cell toxicity of 24-HC may aggravate the symptoms [non-patent document 25: Psychoneuroendocrinology, vol. 28, pages 83-96, 2003]. Therefore, a Cyp46 (CH24H) inhibitor that inhibits metabolizing cholesterol to 24-HC in the brain is promising as a therapeutic or prophylactic drug for schizophrenia.

Patent Document 1 discloses the following compound as an agent for the treatment of virus infection.

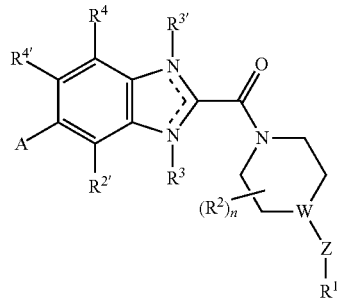

wherein

Z is bond or $(C_1-C_3)$alkylene;

W is selected from CH or N;

A is selected from the group consisting of hydrogen, halo, $(C_1-C_6)$alkyl, $(C_1-C_6)$ alkoxy and the like;

$R^1$ is selected from the group consisting of hydrogen, halo, cyano, hydroxy, $(C_1-C_6)$ alkyl, $(C_1-C_6)$ alkoxy and the like;

$R^2$ is independently selected from the group consisting of hydroxy, oxo, $(C_1-C_6)$alkyl, $(C_3-C_{14})$cycloalkyl and the like;

$R^{2'}$, $R^3$, $R^{3'}$ and $R^{4'}$ are independently selected from hydrogen, $(C_1-C_6)$ alkyl, $(C_3-C_{14})$ cycloalkyl and the like;

$R^4$ is selected from the group consisting of hydrogen, hydroxy, halo, nitrile, $(C_1-C_6)$ alkyl, $(C_1-C_6)$ alkoxy and the like; and n is an integer of 1 to 4.

Patent Documents 2 and 3 disclose the following compound having an HIF inhibitory action as an agent for the prophylaxis or treatment of inflammatory disease, cancer and the like.

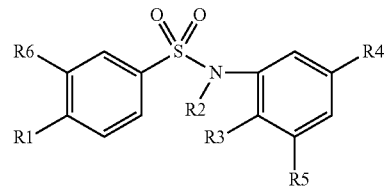

wherein

R1 is H, alkyl, alkenyl, alkynyl, —CN, halogen or the like,

R2 is H or $C_1-C_4$ alkyl,

R3 is H or —$CH_3$,

R4 is an optionally substituted phenyl or the like,

R5 is H or —$CH_3$, and

R6 is H, halogen, alkyl, alkoxy, alkenyl, alkynyl or the like, provided that

R4 is not 3-alkoxy-pyridazin-5-yl, when R4 is phenyl, then the 2- and 5-positions of the phenyl ring may not be substituted with two methoxy substituents at the same time, and R3 and R5 are not at the same time H.

Patent Document 4 discloses the following compound having a PGD2 receptor antagonistic action as an agent for the prophylaxis or treatment of allergic disease and the like.

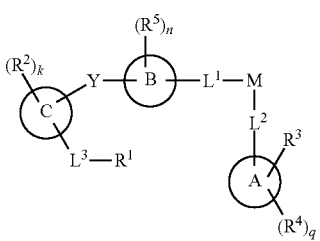

wherein
Ring A is an aromatic carbocycle or an aromatic heterocycle;
Ring B is a nitrogen-containing non-aromatic heterocycle or a nitrogen-containing aromatic heterocycle;
Ring C is an aromatic carbocycle or an aromatic heterocycle;
$R^1$ is hydroxyalkyl, carboxy, alkyloxycarbonyl or the like;
each $R^2$ is independently a halogen atom, optionally substituted alkyl or the like;
$R^3$ is a hydrogen atom, optionally substituted alkyloxy or the like;
each $R^4$ is independently a halogen atom, optionally substituted alkyl or the like;
each $R^5$ is independently a halogen atom, optionally substituted alkyl or the like;
M is carbonyl or sulfonyl;
Y is a single bond, alkylene which optionally contains 1 or 2 hetero atoms and is optionally substituted, or the like;
$L^1$, $L^2$, and $L^3$ are each independently a single bond, alkylene which optionally contains 1 or 2 hetero atoms and is optionally substituted, or the like;
K is 0, 1, 2, 3 or 4;
n is 0, 1 or 2; and
q is 0, 1, 2 or 3

Patent Document 5 discloses the following compound as an inhibitor of BACE2, Cathepsin D and the like, which is an agent for the treatment of neurodegenerative disease (e.g., Alzheimer's disease, Down syndrome, etc.).

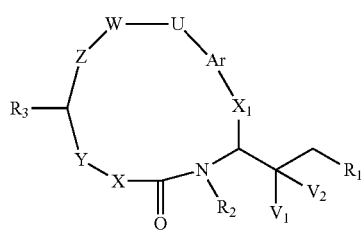

wherein
$R_1$ is CH ($R_e$) C(=O)N($R_a$)$R_b$ or $(CH_2)_k$N($R_c$)$R_d$
  wherein
  k is 0, 1 or 2;
  $R_a$ and $R_b$ are independently hydrogen or optionally substituted $(C_{1-8})$alkyl or the like,
  $R_c$ and $R_d$ are independently hydrogen or optionally substituted $(C_{1-8})$alkyl or the like, or
  $R_a$ and $R_b$ in combination or $R_c$ and $R_d$ in combination form, together with the nitrogen that they are bonded to,
  optionally substituted pyrrolidinyl, 1-piperidinyl or the like; and
  $R_e$ is optionally substituted $(C_{1-8})$ alkyl, $(C_{1-4})$alkoxy$(C_{1-4})$alkyl or the like;
$R_2$ is hydrogen or $(C_{1-4})$alkyl;

$R_3$ is hydrogen, $(C_{1-6})$ alkyl, optionally substituted $(C_{1-6})$ alkylOC(=O)NH or the like;
Ar is an aromatic or hetero aromatic ring, each optionally substituted by halogen, $(C_{1-4})$alkoxy, hydroxy or $(C_{1-4})$ alkyl, and
U and $X_1$ are bonded to the ring at ortho- or meta-position, each other;
U is a bond, —O—, $CF_2$, $CF_2CF_2$ or the like,
$R_g$ is hydrogen, $(C_{1-8})$ alkyl or $(C_{3-7})$cycloalkyl;
$V_1$ is hydrogen, and
$V_2$ is hydroxy, or
$V_1$ and $V_2$ in combination form oxo;
W is CH=CH, cycloprop-1,2-ylene or the like,
$X_1$ is $CR_fR_f$,
  wherein each $R_f$ is independently hydrogen, fluorine, optionally substituted $(C_{1-8})$ alkyl, $(C_{1-4})$alkoxy$(O_{1-4})$ alkyl, $(C_{3-7})$cycloalkyl or $(C_{3-7})$cycloalkyl$(C_{1-4})$alkyl group;
Y is a bond, O, S(=O)$_2$, S(=O)$_2$NR$_g$, N(R$_g$)S(=O)$_2$ or the like,
  wherein $R_g$ is hydrogen, $(C_{1-8})$alkyl or $(C_{3-7})$cycloalkyl; and
Z is O, $CH_2$, $CF_2$, CHF, cycloprop-1,2-ylene or a bond, the large cyclic ring contains 14, 15, 16 or 17 ring atoms.

Patent Document 6 discloses the following compound having a CH24H inhibitory action as an agent for the treatment of neurodegenerative disease (e.g., Alzheimer's disease, mild cognitive disorder, multiple sclerosis and the like).

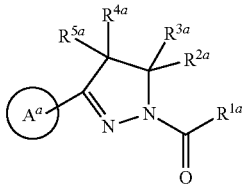

(Ia)

wherein
Ring $A^a$ is an optionally substituted ring;
$R^{1a}$ is
(1) a group represented by the formula: —$X^{1a}$—$R^{6a}$
  wherein $X^{1a}$ is a $C_{1-6}$ alkylene group, a $C_{2-6}$ alkenylene group or a $C_{3-6}$ cycloalkylene group, and $R^{6a}$ is an optionally substituted $C_{6-14}$ aryl group, an optionally substituted $C_{6-14}$ aryloxy group or an optionally substituted heterocyclic group,
(2) an optionally substituted $C_{6-14}$ aryl group,
(3) an optionally substituted $C_{6-14}$ aryloxy group, or
(4) an optionally substituted heterocyclic group;
$R^{2a}$ is a hydrogen atom, an optionally substituted $C_{1-6}$ alkyl group, an optionally substituted $C_{3-6}$ cycloalkyl group or an optionally substituted hydroxy group,
$R^{3a}$ is an optionally substituted $C_{1-6}$ alkyl group, an optionally substituted $C_{3-6}$ cycloalkyl group or an optionally substituted hydroxy group, or
$R^{2a}$ and $R^{3a}$ in combination optionally form an oxo group, a $C_{1-3}$ alkylidene group or an optionally substituted ring; and
$R^{4a}$ and $R^{5a}$ are the same or different and each is a hydrogen atom, a halogen atom, an optionally substituted $C_{1-6}$ alkyl group, an optionally substituted $C_{3-6}$ cycloalkyl group or an optionally substituted hydroxy group, or
$R^{4a}$ and $R^{5a}$ in combination optionally form an oxo group, a $C_{1-3}$ alkylidene group or an optionally substituted ring.

Patent Document 7 discloses the following compound having a calcium-sensing receptor (CaSR) antagonistic action as an agent for the treatment of bone disease (e.g., osteoporosis, bone fracture and the like).

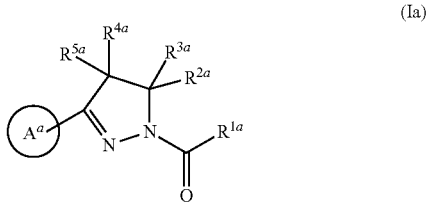

(Ia)

wherein

Ring $A^a$ is an optionally substituted ring;

$R^{1a}$ is (1) a group represented by the formula: $-X^{1a}-R^{6a}$ wherein $X^{1a}$ is a $C_{1-6}$ alkylene group, a $C_{2-6}$ alkenylene group or a $C_{3-6}$ cycloalkylene group, and $R^{6a}$ is an optionally substituted $C_{3-6}$ cycloalkyl group, an optionally substituted $C_{3-6}$ cycloalkyloxy group, an optionally substituted $C_{6-14}$ aryl group, an optionally substituted $C_{6-14}$ aryloxy group, an optionally substituted $C_{7-14}$ aralkyloxy group, an optionally substituted heterocyclic group, an optionally substituted heterocyclyloxy group or optionally substituted amino group, (2) an optionally substituted $C_{3-6}$ cycloalkyl group,
(3) an optionally substituted $C_{3-6}$ cycloalkyloxy group,
(4) an optionally substituted $C_{6-14}$ aryl group,
(5) an optionally substituted $C_{6-14}$ aryloxy group,
(6) an optionally substituted $C_{7-14}$ aralkyloxy group,
(7) an optionally substituted heterocyclic group,
(8) an optionally substituted heterocyclyloxy group, or
(9) an optionally substituted amino group;

$R^{2a}$ is a hydrogen atom, an optionally substituted $C_{1-6}$ alkyl group, an optionally substituted $C_{3-6}$ cycloalkyl group or an optionally substituted hydroxy group, $R^{3a}$ is an optionally substituted $C_{1-6}$ alkyl group, an optionally substituted $C_{3-6}$ cycloalkyl group or an optionally substituted hydroxy group, or $R^{2a}$ and $R^{3a}$ in combination optionally form a $C_{1-3}$ alkylidene group or an optionally substituted ring; and $R^{4a}$ and $R^{5a}$ are the same or different and each is a hydrogen atom, a halogen atom, an optionally substituted $C_{1-6}$ alkyl group, an optionally substituted $C_{3-6}$ cycloalkyl group or an optionally substituted hydroxy group, or $R^{4a}$ and $R^{5a}$ in combination optionally form an oxo group, a $C_{1-3}$ alkylidene group or an optionally substituted ring.

DOCUMENT LIST

Patent Document

Patent Document 1: WO 2011/097491
Patent Document 2: WO 2010/075869
Patent Document 3: WO 2010/076033
Patent Document 4: WO 2007/037187
Patent Document 5: WO 2006/074950
Patent Document 6: WO 2010/110400
Patent Document 7: JP 2010-248183

Non-Patent Document

Non-Patent Document 1: Science, vol. 261, pages 921-923, 1993
Non-Patent Document 2: Neurobiology of Aging (Neurobiol. Aging), vol. 24, pages 421-426, 2003
Non-Patent Document 3: Molecular Psychiatry (Mol. Psychiatry), vol. 8, pages 635-638, 2003
Non-Patent Document 4: Neuroscience Letters (Neurosci. Lett.), vol. 328, pages 9-12, 2002
Non-Patent Document 5: Journal of the Biological Chemistry (J. Biol. Chem.), vol. 279, pages 34674-34681, 2004
Non-Patent Document 6: Neuroscience Letters (Neurosci. Lett.), vol. 324, pages 83-85, 2002
Non-Patent Document 7: Neuroscience Letters (Neurosci. Lett.), vol. 397, pages 83-87, 2006
Non-Patent Document 8: Brain Research (Brain Res.), vol. 818, pages 171-175, 1999
Non-Patent Document 9: Neuroscience, vol. 164, pages 398-403, 2009
Non-Patent Document 10: British Journal of Pharmacology, vol. 149, pages 998-1012, 2006
Non-Patent Document 11: Journal of Neuroscience Research (J. Neurosci. Res.), vol. 85, pages 1499-1505, 2007
Non-Patent Document 12: Neuroscience Letters (Neurosci. Lett.), vol. 331, pages 163-166, 2002
Non-Patent Document 13: Proceedings of the National Academy of Sciences USA (Proc. Natl. Acad. Sci. USA), vol. 102, pages 8333-8338, 2005
Non-Patent Document 14: Journal of Neurotrauma (J. Neurotrauma), vol. 25, pages 1087-1098, 2008
Non-Patent Document 15: NeuroReport, vol. 16, pages 909-913, 2005
Non-Patent Document 16: Glia, vol. 50, pages 427-434, 2005
Non-Patent Document 17: Molecular Neurodegeneration (Mol. Neurodegeneration), vol. 4, pages 47-59, 2009
Non-Patent Document 18: Investigative Ophthalmology & Visual Science (Invest. Opthalmol. Vis. Sci.), vol. 50, pages 5712-5717, 2009
Non-Patent Document 19: Epilepsia, vol. 47, pages 867-872, 2006
Non-Patent Document 20: Epilepsia, vol. 52, Supplement 1, pages 39-46, 2011
Non-Patent Document 21: Journal of Neuroscience (J. Neurosci.), vol. 29, pages 3453-3462, 2012
Non-Patent Document 22: Journal of Neurology (J. Neurol.), vol. 65, pages 652-663, 2006
Non-Patent Document 23: Journal of Neurology Neurosurgery Psychiatry (J. Neurol. Neurosurg. Psychiatry), vol. 48, pages 459-468, 1985
Non-Patent Document 24: Journal of Psychiatry Neuroscience (J. Psychiatry Neurosci.), vol. 36, pages 47-55, 2011
Non-Patent Document 25: Psychoneuroendocrinology, vol. 28, pages 83-96, 2003

SUMMARY OF THE INVENTION

Problems to be Solved by the Invention

An object of the present invention is to provide a compound having a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

Means of Solving the Problems

The present inventors have conducted intensive studies in an attempt to solve the above-mentioned problem and found that compound (I) represented by the following formula has a superior CH24H inhibitory action, which resulted in the completion of the present invention.

Accordingly, the present invention provides the following.

[1] A compound represented by the formula (I):

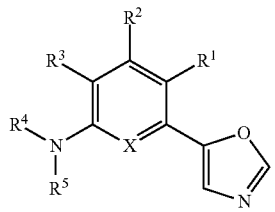

wherein
X is a nitrogen atom or $CR^6$;
$R^1$ is a hydrogen atom or a substituent;
$R^2$ is a halogen atom, a cyano group, an optionally substituted $C_{1-6}$ alkyl group or an optionally substituted carbocyclic group; or
$R^1$ and $R^2$ in combination optionally form an optionally further substituted ring;
$R^3$ is a hydrogen atom or a chain substituent;
$R^4$ is a substituent;
$R^5$ is a hydrogen atom or a substituent; and
$R^6$ is a hydrogen atom or a substituent; or
$R^4$ and $R^5$ in combination optionally form an optionally further substituted nitrogen-containing non-aromatic heterocycle; or
$R^5$ and $R^6$ in combination optionally form an optionally further substituted nitrogen-containing non-aromatic heterocycle, provided that 4-methyl-N-(3-methyl-5-(1,3-oxazol-5-yl)phenyl)benzenesulfonamide, and 4-methoxy-N-(3-methyl-5-(1,3-oxazol-5-yl)phenyl)benzenesulfonamide are excluded, or a salt thereof (hereinafter to be referred to as compound (I)).

[A] The compound or salt of the above-mentioned [1], wherein
X is a nitrogen atom or $CR^6$;
$R^1$ is a hydrogen atom;
$R^2$ is a halogen atom, a cyano group, an optionally substituted $C_{1-6}$ alkyl group or an optionally substituted carbocyclic group; or
$R^1$ and $R^2$ in combination optionally form an optionally further substituted ring;
$R^3$ is a hydrogen atom;
$R^4$ is a substituent;
$R^5$ is a hydrogen atom; and
$R^6$ is a hydrogen atom; or
$R^4$ and $R^5$ in combination optionally form an optionally further substituted nitrogen-containing non-aromatic heterocycle; or
$R^5$ and $R^6$ in combination optionally form an optionally further substituted nitrogen-containing non-aromatic heterocycle, provided that 4-methyl-N-(3-methyl-5-(1,3-oxazol-5-yl)phenyl)benzenesulfonamide, and 4-methoxy-N-(3-methyl-5-(1,3-oxazol-5-yl)phenyl)benzenesulfonamide are excluded.

[B] The compound or salt of the above-mentioned [1], wherein
X is a nitrogen atom or $CR^6$;
$R^1$ is a hydrogen atom;
$R^2$ is a halogen atom, a cyano group, a substituted methyl group, an optionally substituted $C_{2-6}$ alkyl group or an optionally substituted carbocyclic group; or
$R^1$ and $R^2$ in combination optionally form an optionally further substituted ring;
$R^3$ is a hydrogen atom;
$R^4$ is a substituent;
$R^5$ is a hydrogen atom; and
$R^6$ is a hydrogen atom; or
$R^4$ and $R^5$ in combination optionally form an optionally further substituted nitrogen-containing non-aromatic heterocycle; or
$R^5$ and $R^6$ in combination optionally form an optionally further substituted nitrogen-containing non-aromatic heterocycle.

[C] The compound or salt of the above-mentioned [1], wherein
X is a nitrogen atom or $CR^6$;
$R^1$ is a hydrogen atom;
$R^2$ is
(1) a halogen atom,
(2) a cyano group,
(3) a $C_{1-6}$ alkyl group optionally substituted by 1 to 3 halogen atoms, or
(4) a $C_{3-8}$ cycloalkyl group; or
$R^1$ and $R^2$ in combination optionally form a 5-membered heterocycle optionally further substituted by $C_{1-6}$ alkyl group(s);
$R^3$ is a hydrogen atom;
$R^4$ is
(1) a $C_{1-6}$ alkyl group optionally substituted by 1 to 3 substituents selected from
    (a) a $C_{3-8}$ cycloalkyl group, and
    (b) a heterocyclic group,
(2) a $C_{1-6}$ alkyl-carbonyl group optionally substituted by 1 to 3 substituents selected from
    (a) a halogen atom,
    (b) a $C_{3-8}$ cycloalkyl group,
    (c) a $C_{1-6}$ alkoxy group,
    (d) a $C_{6-14}$ aryl group optionally substituted by 1 to 3 halogen atoms, and
    (e) a heterocyclic group optionally substituted by 1 to 3 $C_{1-6}$ alkyl groups,
(3) a $C_{1-6}$ alkoxy-carbonyl group,
(4) a $C_{3-8}$ cycloalkyl-carbonyl group optionally substituted by 1 to 3 substituents selected from
    (a) a hydroxy group,
    (b) a halogen atom,
    (c) a cyano group, and
    (d) a $C_{1-6}$ alkyl group,
(5) a $C_{6-14}$ aryl-carbonyl group optionally substituted by 1 to 3 substituents selected from
    (a) a halogen atom, and
    (b) a $C_{1-6}$ alkoxy group,
(6) a heterocyclylcarbonyl group optionally substituted by 1 to 3 substituents selected from
    (a) a halogen atom,
    (b) a $C_{1-6}$ alkyl group optionally substituted by 1 to 3 $C_{6-14}$ aryl groups, and
    (c) an oxo group,
(7) a $C_{3-8}$ cycloalkylsulfonyl group, (8) a $C_{6-14}$ arylsulfonyl group optionally substituted by 1 to 3 halogen atoms, or
(9) a carbamoyl group optionally mono- or di-substituted by $C_{1-6}$ alkyl group(s);
$R^5$ is a hydrogen atom; and
$R^6$ is a hydrogen atom; or
$R^4$ and $R^5$ in combination optionally form a nitrogen-containing non-aromatic heterocycle optionally substituted by 1 to 3 substituents selected from
   (1) a hydroxy group,
   (2) a halogen atom,
   (3) a $C_{1-6}$ alkyl group optionally substituted by $C_{6-14}$ aryl group(s) optionally substituted by 1 to 3 $C_{1-6}$ alkoxy groups,
   (4) a $C_{1-6}$ alkoxy group optionally substituted by 1 to 3 $C_{6-14}$ aryl groups,
   (5) a $C_{1-6}$ alkyl-carbonyl group,
   (6) a $C_{1-6}$ alkoxy-carbonyl group,
   (7) a $C_{1-6}$ alkylsulfonyl group,
   (8) an amino group optionally mono- or di-substituted by substituent(s) selected from
     (a) a $C_{1-6}$ alkyl-carbonyl group, and
     (b) a $C_{1-6}$ alkylsulfonyl group,
   (9) an azido group, and
   (10) an oxo group; or
$R^5$ and $R^6$ in combination optionally form a nitrogen-containing non-aromatic heterocycle optionally substituted by one oxo group.

[2] The compound or salt of the above-mentioned [1], wherein
X is a nitrogen atom or $CR^6$;
$R^1$ is a hydrogen atom;
$R^2$ is
(1) a halogen atom,
(2) a cyano group,
(3) a $C_{1-6}$ alkyl group optionally substituted by 1 to 3 halogen atoms, or
(4) a $C_{3-8}$ cycloalkyl group; or
$R^1$ and $R^2$ in combination optionally form a dihydrofuran ring or a pyrazole ring, each optionally further substituted by $C_{1-6}$ alkyl group(s);
$R^3$ is a hydrogen atom;
$R^4$ is
(1) a $C_{1-6}$ alkyl group optionally substituted by 1 to 3 substituents selected from
   (a) a $C_{3-8}$ cycloalkyl group, and
   (b) a pyridyl group,
(2) a $C_{1-6}$ alkyl-carbonyl group optionally substituted by 1 to 3 substituents selected from
   (a) a halogen atom,
   (b) a $C_{3-8}$ cycloalkyl group,
   (c) a $C_{1-6}$ alkoxy group,
   (d) a $C_{6-14}$ aryl group optionally substituted by 1 to 3 halogen atoms, and
   (e) an imidazolyl group, a pyrazolyl group and a furyl group, each optionally substituted by 1 to 3 $C_{1-6}$ alkyl groups,
(3) a $C_{1-6}$ alkoxy-carbonyl group,
(4) a $C_{3-8}$ cycloalkyl-carbonyl group optionally substituted by 1 to 3 substituents selected from
   (a) a hydroxy group,
   (b) a halogen atom,
   (c) a cyano group, and
   (d) a $C_{1-6}$ alkyl group,
(5) a $C_{6-14}$ aryl-carbonyl group optionally substituted by 1 to 3 substituents selected from
   (a) a halogen atom, and
   (b) a $C_{1-6}$ alkoxy group,
(6) an azetidinylcarbonyl group, an oxetanylcarbonyl group, a pyrrolidinylcarbonyl group, a thienylcarbonyl group, a furylcarbonyl group, a piperidylcarbonyl group, a pyridylcarbonyl group, a morpholinylcarbonyl group, a tetrahydropyranylcarbonyl group, a 2-oxa-5-azabicyclo[2.2.1]heptylcarbonyl group, a 3-oxa-6-azabicyclo[3.1.1]heptylcarbonyl group or a 3-oxa-8-azabicyclo[3.2.1]octylcarbonyl group, each optionally substituted by 1 to 3 substituents selected from
   (a) a halogen atom,
   (b) a $C_{1-6}$ alkyl group optionally substituted by 1 to 3 $C_{6-14}$ aryl groups, and
   (c) an oxo group,
(7) a $C_{3-8}$ cycloalkylsulfonyl group,
(8) a $C_{6-14}$ arylsulfonyl group optionally substituted by 1 to 3 halogen atoms, or
(9) a carbamoyl group optionally mono- or di-substituted by $C_{1-6}$ alkyl group(s);
$R^5$ is a hydrogen atom; and
$R^6$ is a hydrogen atom; or
$R^4$ and $R^5$ in combination optionally form a pyrrolidine ring, an imidazolidine ring, a dihydropyridine ring, a piperidine ring, a piperazine ring, a morpholine ring or a 2-oxa-5-azabicyclo[2.2.1]heptane ring, each optionally substituted by 1 to 3 substituents selected from
   (1) a hydroxy group,
   (2) a halogen atom,
   (3) a $C_{1-6}$ alkyl group optionally substituted by $C_{6-14}$ aryl group(s) optionally substituted by 1 to 3 $C_{1-6}$ alkoxy groups,
   (4) a $C_{1-6}$ alkoxy group optionally substituted by 1 to 3 $C_{6-14}$ aryl groups,
   (5) a $C_{1-6}$ alkyl-carbonyl group,
   (6) a $C_{1-6}$ alkoxy-carbonyl group,
   (7) a $C_{1-6}$ alkylsulfonyl group,
   (8) an amino group optionally mono- or di-substituted by substituent(s) selected from
     (a) a $C_{1-6}$ alkyl-carbonyl group, and
     (b) a $C_{1-6}$ alkylsulfonyl group,
   (9) an azido group, and (10) an oxo group; or
$R^5$ and $R^6$ in combination optionally form a dihydropyrrole ring, a dihydrooxazine ring or a tetrahydrooxazepine ring, each optionally substituted by one oxo group.

[3] The compound or salt of the above-mentioned [1], wherein
X is a nitrogen atom or $CR^6$;
$R^1$ is a hydrogen atom;
$R^2$ is
(1) a halogen atom,
(2) a cyano group,
(3) a $C_{1-6}$ alkyl group optionally substituted by 1 to 3 halogen atoms, or
(4) a cyclopropyl group; or
$R^1$ and $R^2$ in combination optionally form a dihydrofuran ring or a pyrazole ring, each optionally further substituted by $C_{1-6}$ alkyl group(s);
$R^3$ is a hydrogen atom;
$R^4$ is
(1) a $C_{1-6}$ alkyl group optionally substituted by 1 to 3 substituents selected from
   (a) a cyclopropyl group, and
   (b) a pyridyl group,
(2) a $C_{1-6}$ alkyl-carbonyl group optionally substituted by 1 to 3 substituents selected from
   (a) a halogen atom,
   (b) a cyclopropyl group, (c) a $C_{1-6}$ alkoxy group,
(d) a phenyl group optionally substituted by 1 to 3 halogen atoms, and
(e) an imidazolyl group, a pyrazolyl group and a furyl group, each optionally substituted by 1 to 3 alkyl groups,
(3) a $C_{1-6}$ alkoxy-carbonyl group,
(4) a cyclopropylcarbonyl group, a cyclobutylcarbonyl group, a cyclopentylcarbonyl group or a cyclohexylcarbonyl group, each optionally substituted by 1 to 3 substituents selected from
(a) a hydroxy group,
(b) a halogen atom,
(c) a cyano group, and
(d) a $C_{1-6}$ alkyl group,
(5) a benzoyl group optionally substituted by 1 to 3 substituents selected from
(a) a halogen atom, and
(b) a $C_{1-6}$ alkoxy group,
(6) an azetidinylcarbonyl group, an oxetanylcarbonyl group, a pyrrolidinylcarbonyl group, a thienylcarbonyl group, a furylcarbonyl group, a piperidylcarbonyl group, a pyridylcarbonyl group, a morpholinylcarbonyl group, a tetrahydropyranylcarbonyl group, a 2-oxa-5-azabicyclo[2.2.1]heptylcarbonyl group, a 3-oxa-6-azabicyclo[3.1.1]heptylcarbonyl group or a 3-oxa-8-azabicyclo[3.2.1]octylcarbonyl group, each optionally substituted by 1 to 3 substituents selected from
(a) a halogen atom,
(b) a $C_{1-6}$ alkyl group optionally substituted by 1 to 3 phenyl groups, and
(c) an oxo group,
(7) a cyclopropylsulfonyl group,
(8) a phenylsulfonyl group optionally substituted by 1 to 3 halogen atoms, or
(9) a carbamoyl group optionally mono- or di-substituted by $C_{1-6}$ alkyl group(s);
$R^5$ is a hydrogen atom; and
$R^6$ is a hydrogen atom; or
$R^4$ and $R^5$ in combination optionally form a pyrrolidine ring, an imidazolidine ring, a dihydropyridine ring, a piperidine ring, a piperazine ring, a morpholine ring or a 2-oxa-5-azabicyclo[2.2.1]heptane ring, each optionally substituted by 1 to 3 substituents selected from
(1) a hydroxy group,
(2) a halogen atom,
(3) a $C_{1-6}$ alkyl group optionally substituted by phenyl group(s) optionally substituted by 1 to 3 $C_{1-6}$ alkoxy groups,
(4) a $C_{1-6}$ alkoxy group optionally substituted by 1 to 3 phenyl groups,
(5) a $C_{1-6}$ alkyl-carbonyl group,
(6) a $C_{1-6}$ alkoxy-carbonyl group,
(7) a $C_{1-6}$ alkylsulfonyl group,
(8) an amino group optionally mono- or di-substituted by substituent(s) selected from
(a) a $C_{1-6}$ alkyl-carbonyl group, and
(b) a $C_{1-6}$ alkylsulfonyl group,
(9) an azido group, and
(10) an oxo group; or
$R^5$ and $R^6$ in combination optionally form a dihydropyrrole ring, a dihydrooxazine ring or a tetrahydrooxazepine ring, each optionally substituted by one oxo group.
[4] The compound or salt of the above-mentioned [1], wherein
X is a nitrogen atom or $CR^6$;
$R^1$ is a hydrogen atom;
$R^2$ is a $C_{1-6}$ alkyl group substituted by 1 to 3 halogen atoms;
$R^3$ is a hydrogen atom;
$R^4$ is
(1) a cyclopropylcarbonyl group, or
(2) a tetrahydropyranylcarbonyl group or a morpholinylcarbonyl group;
$R^5$ is a hydrogen atom; and
$R^6$ is a hydrogen atom; or
$R^5$ and $R^6$ in combination optionally form a dihydropyrrole ring.
[D] cyclopropyl(4-(1,3-oxazol-5-yl)-6-(trifluoromethyl)-2,3-dihydro-1H-indol-1-yl)methanone or a salt thereof,
N-(6-(1,3-oxazol-5-yl)-4-(trifluoromethyl)pyridin-2-yl)cyclopropanecarboxamide or a salt thereof, or
(4-(1,3-oxazol-5-yl)-6-(trifluoromethyl)-2,3-dihydro-1H-indol-1-yl) (tetrahydro-2H-pyran-4-yl)methanone or a salt thereof.
[5] Cyclopropyl(4-(1,3-oxazol-5-yl)-6-(trifluoromethyl)-2,3-dihydro-1H-indol-1-yl)methanone or a salt thereof.
[6] N-(6-(1,3-Ooxazol-5-yl)-4-(trifluoromethyl)pyridin-2-yl)cyclopropanecarboxamide or a salt thereof.
[7] (4-(1,3-Oxazol-5-yl)-6-(trifluoromethyl)-2,3-dihydro-1H-indol-1-yl) (tetrahydro-2H-pyran-4-yl)methanone or a salt thereof.
[8] A medicament comprising the compound or salt of any of the above-mentioned [1] to [7] and [A] to [D].
[9] The medicament of the above-mentioned [8], which is a cholesterol 24 hydroxylase inhibitor.
[10] The medicament of the above-mentioned [8], which is an agent for the prophylaxis or treatment of epilepsy or neurodegenerative disease.
[11] The medicament of the above-mentioned [10], wherein the neurodegenerative disease is Alzheimer's disease, mild cognitive disorder, Huntington's disease, Parkinson's disease or multiple sclerosis.
[12] The compound or salt of any of the above-mentioned [1] to [7] and [A] to [D] for use in the prophylaxis or treatment of epilepsy or neurodegenerative disease.
[13] The compound or salt of the above-mentioned [12], wherein the neurodegenerative disease is Alzheimer's disease, mild cognitive disorder, Huntington's disease, Parkinson's disease or multiple sclerosis.
[14] A method of inhibiting cholesterol 24-hydroxylase in a mammal, which comprises administering an effective amount of the compound or salt of any of the above-mentioned [1] to [7] and [A] to [D] to the mammal.
[15] A method for the prophylaxis or treatment of epilepsy or neurodegenerative disease in a mammal, which comprises administering an effective amount of the compound or salt of any of the above-mentioned [1] to [7] and [A] to [D] to the mammal.
[16] The method of the above-mentioned [15], wherein the neurodegenerative disease is Alzheimer's disease, mild cognitive disorder, Huntington's disease, Parkinson's disease or multiple sclerosis.
[17] Use of the compound or salt of any of the above-mentioned [1] to [7] and [A] to [D] for the production of an agent for the prophylaxis or treatment of epilepsy or neurodegenerative disease.
[18] The use of the above-mentioned [17], wherein the neurodegenerative disease is Alzheimer's disease, mild cognitive disorder, Huntington's disease, Parkinson's disease or multiple sclerosis.

Effect of the Invention

Compound (I) has a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

DETAILED DESCRIPTION OF THE INVENTION

In the present specification, the "halogen atom" means a fluorine atom, a chlorine atom, a bromine atom or an iodine atom.

In the present specification, the "$C_{1-6}$ alkyl (group)" means, for example, methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkyl (group)" means, for example, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{3-10}$ alkenyl (group)" means, for example, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl or the like.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{3-10}$ alkynyl (group)" means, for example, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl or the like.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "mono-$C_{1-6}$ alkylamino (group)" means, for example, methylamino, ethylamino, propylamino, isopropylamino, butylamino, isobutylamino, tert-butylamino or the like.

In the present specification, the "di-$C_{1-6}$ alkylamino (group)" means, for example, dimethylamino, diethylamino, dipropylamino, diisopropylamino, dibutylamino, diisobutylamino, ditert-butylamino or the like.

In the present specification, the "$C_{3-8}$ cycloalkyl (group)" means, for example, cyclopropyl, cyclobutyl, cyclopentyl, cyclohexyl, cycloheptyl, cyclooctyl or the like.

In the present specification, the "$C_{3-6}$ cycloalkyl (group)" means, for example, one having 3 to 6 carbon atoms, from among the above-mentioned $C_{3-8}$ cycloalkyl (group).

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "$C_{3-6}$ cycloalkyloxy (group)" means, for example, cyclopropyloxy, cyclobutyloxy, cyclopentyloxy, cyclohexyloxy or the like.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{4-6}$ cycloalkadienyl group" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl or the like.

The above-mentioned $C_{3-8}$ cycloalkyl group, $C_{3-8}$ cycloalkenyl group and $C_{4-6}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-8}$ cycloalkyl group, $C_{3-8}$ cycloalkenyl group and $C_{4-6}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

The above-mentioned $C_{3-8}$ cycloalkyl group, $C_{3-8}$ cycloalkenyl group and $C_{4-6}$ cycloalkadienyl group each optionally form a spiro ring group with a $C_{3-8}$ cycloalkane, a cycloalkene or a $C_{4-6}$ cycloalkadiene. Examples of the $C_{3-8}$ cycloalkane, cycloalkene and $C_{4-6}$ cycloalkadiene include rings corresponding to the above-mentioned $C_{3-8}$ cycloalkyl group, $C_{3-8}$ cycloalkenyl group and $C_{4-6}$ cycloalkadienyl group. Examples of the spiro ring group include spiro[4.5]decan-8-yl and the like.

In the present specification, the "$C_{6-14}$ aryloxy (group)" means, for example, phenoxy, 1-naphthyloxy, 2-naphthyloxy or the like.

In the present specification, the "$C_{7-14}$ aralkyloxy (group)" means, for example, benzyloxy, phenethyloxy or the like.

Each symbol of the formula (I) is explained below.

In the formula (I), X is a nitrogen atom or $CR^6$. X is preferably $CR^6$.

In the formula (I), $R^6$ is a hydrogen atom or a substituent.

Examples of the "substituent" represented by $R^6$ include an "optionally substituted hydrocarbon group", an "optionally substituted heterocyclic group", an "optionally substituted hydroxy group", an "optionally substituted amino group", an "optionally substituted sulfanyl group", an "acyl group", a "halogen atom", a "cyano group", a "nitro group" and the like.

Examples of the "hydrocarbon group" of the "optionally substituted hydrocarbon group" include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Among them, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl and the like. Among them, a $C_{2-6}$ alkenyl group is preferable.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl and the like. Among them, a $C_{2-6}$ alkynyl group is preferable.

Examples of the $C_{3-10}$ cycloalkyl group include cyclopropyl, cyclobutyl, cyclopentyl, cyclohexyl, cycloheptyl, cyclooctyl and the like. Among them, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Among them, a $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Among them, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

The above-mentioned $C_{3-10}$ cycloalkyl group, $C_{3-10}$ cycloalkenyl group and $C_{4-10}$ cycloalkadienyl group each optionally form a spiro ring group with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

Examples of the $C_{6-14}$ aryl group include phenyl, naphthyl, anthryl, phenanthryl, acenaphthylenyl, biphenylyl and the like. Among them, a $C_{6-12}$ aryl group is preferable.

Examples of the $C_{7-14}$ aralkyl group include benzyl, phenethyl, naphthyl methyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the above-mentioned "hydrocarbon group", optionally have 1 to 7 (preferably 1 to 3) substituents at substitutable position(s).

Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
 (a) a halogen atom,
 (b) a cyano group,
 (c) a $C_{1-6}$ alkyl group optionally substituted by 1 to 3 halogen atoms, and
 (d) a $C_{1-6}$ alkoxy group optionally substituted by 1 to 3 halogen atoms;
(6) a $C_{6-14}$ aryl group optionally substituted by 1 to 3 Substituents selected from
 (a) a halogen atom,
 (b) a cyano group,
 (c) a $C_{1-6}$ alkyl group optionally substituted by 1 to 3 halogen atoms, and
 (d) a $C_{1-6}$ alkoxy group optionally substituted by 1 to 3 halogen atoms;
(7) a $C_{1-6}$ alkoxy group optionally substituted by 1 to 3 substituents selected from
 (a) a halogen atom,
 (b) a cyano group,
 (c) a $C_{3-8}$ cycloalkyl group optionally having 1 to 3 halogen atoms,
 (d) a $C_{3-8}$ cycloalkenyl group optionally having 1 to 3 halogen atoms,
 (e) a $C_{6-14}$ aryl group optionally having 1 to 3 halogen atoms, and
 (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;

(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
   (a) a $C_{1-6}$ alkyl group,
   (b) a $C_{3-6}$ cycloalkyl group,
   (c) a $C_{6-14}$ aryl group,
   (d) a $C_{1-6}$ alkoxy group,
   (e) a 5- or 6-membered monocyclic aromatic heterocyclic group,
   (f) an 8- to 12-membered fused aromatic heterocyclic group,
   (g) a 3- to 8-membered monocyclic non-aromatic heterocyclic group, and
   (h) an 8- to 12-membered fused non-aromatic heterocyclic group;
(15) a sulfamoyl group optionally mono- or di-substituted by substituent(s) selected from
   (a) a $C_{1-6}$ alkyl group,
   (b) a $C_{3-6}$ cycloalkyl group,
   (c) a $C_{6-14}$ aryl group,
   (d) a $C_{1-6}$ alkoxy group,
   (e) a 5- or 6-membered monocyclic aromatic heterocyclic group,
   (f) an 8- to 12-membered fused aromatic heterocyclic group,
   (g) a 3- to 8-membered monocyclic non-aromatic heterocyclic group, and
   (h) an 8- to 12-membered fused non-aromatic heterocyclic group;
(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) an 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) an 8- to 12-membered fused non-aromatic heterocyclylcarbonyl group (e.g., dihydrobenzofuranylcarbonyl);
(30) an amino group optionally mono- or di-substituted by substituent(s) selected from
   (a) a $C_{1-6}$ alkyl group optionally having 1 to 3 halogen atoms,
   (b) a $C_{1-6}$ alkyl-carbonyl group optionally having 1 to 3 halogen atoms,
   (c) a $C_{3-8}$ cycloalkyl-carbonyl group,
   (d) a $C_{6-14}$ aryl-carbonyl group optionally having 1 to 3 halogen atoms,
   (e) a 5- or 6-membered monocyclic aromatic heterocyclylcarbonyl group,
   (f) an 8- to 12-membered fused aromatic heterocyclylcarbonyl group,
   (g) a 3- to 8-membered monocyclic non-aromatic heterocyclylcarbonyl group, and
   (h) an 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{1-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfinyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);

(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) an 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) an 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl) optionally substituted by 1 to 3 substituents selected from
　　(a) a halogen atom,
　　(b) a $C_{1-6}$ alkyl group optionally substituted by 1 to 3 halogen atoms, and
　　(c) a $C_{1-6}$ alkoxy group optionally substituted by 1 to 3 halogen atoms;
(62) an 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
　　(a) a halogen atom,
　　(b) a $C_{1-6}$ alkyl group optionally substituted by 1 to 3 halogen atoms, and
　　(c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
　　(a) a halogen atom,
　　(b) a $C_{1-6}$ alkyl group optionally substituted by 1 to 3 halogen atoms,
　　(c) a $C_{1-6}$ alkoxy group optionally substituted by 1 to 3 halogen atoms, and
　　(d) an oxo group;
(64) an 8- to 12-membered fused non-aromatic heterocyclic group (e.g., dihydrobenzofuranyl) optionally substituted by 1 to 3 substituents selected from
　　(a) a halogen atom,
　　(b) a $C_{1-6}$ alkyl group optionally substituted by 1 to 3 halogen atoms,
　　(c) a $C_{1-6}$ alkoxy group optionally substituted by 1 to 3 halogen atoms, and
　　(d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) an 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) an 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkylthio-carbamoyl group (e.g., methylthiocarbamoyl, ethylthiocarbamoyl, propylthiocarbamoyl);
(80) a di-$C_{1-6}$ alkylthio-carbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

The $C_{3-10}$ cycloalkyl group, $C_{3-10}$ cycloalkenyl group, $C_{4-10}$ cycloalkadienyl group, $C_{6-14}$ aryl group, $C_{7-14}$ aralkyl group and $C_{8-13}$ arylalkenyl group, which are exemplified as the above-mentioned "hydrocarbon group", optionally have 1 to 3 substituents at substitutable position(s).

Examples of the substituent include substituents selected from the following Substituent Group B.
Substituent Group B:
(1) Substituent Group A;
(2) a $C_{1-6}$ alkyl group optionally substituted by 1 to 3 substituents selected from
　　(a) a halogen atom,
　　(b) a cyano group,
　　(c) a hydroxy group,
　　(d) a $C_{3-8}$ cycloalkyl group optionally substituted by 1 to 3 substituents selected from
　　　　(i) a halogen atom,
　　　　(ii) a cyano group, and
　　　　(iii) a $C_{1-6}$ alkyl group optionally substituted by 1 to 3 halogen atoms;

(e) a $C_{6-14}$ aryl group optionally substituted by 1 to 3 substituents selected from
  (i) a halogen atom,
  (ii) a cyano group, and
  (iii) a alkyl group optionally substituted by 1 to 3 halogen atoms,
(f) a $C_{1-6}$ alkoxy group optionally substituted by 1 to 3 halogen atoms,
(g) an amino group optionally mono- or di-substituted by $C_{1-6}$ alkyl group(s),
(h) a 5- or 6-membered monocyclic aromatic heterocyclic group,
(i) an 8- to 12-membered fused aromatic heterocyclic group,
(j) a 3- to 8-membered monocyclic non-aromatic heterocyclic group,
(k) an 8- to 12-membered fused non-aromatic heterocyclic group,
(l) a carboxy group, and
(m) a $C_{1-6}$ alkoxy-carbonyl group optionally substituted by 1 to 3 halogen atoms;
(3) a $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono- or di-substituted by $C_{1-6}$ alkyl group(s),
  (e) a carboxy group, and
  (f) a $C_{1-6}$ alkoxy-carbonyl group; and
(4) a $C_{7-14}$ aralkyl group optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group optionally substituted by 1 to 3 halogen atoms;
and the like. When the number of the substituents is two or more, the respective substituents may be the same or different.

Examples of the "heterocyclic group" of the above-mentioned "optionally substituted heterocyclic group" include an aromatic heterocyclic group and a non-aromatic heterocyclic group.

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;
fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like;
and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially-saturated, and the like.

Preferable examples of the non-aromatic heterocyclic group include
monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like;
and the like.

The above-mentioned "monocyclic non-aromatic heterocyclic group" and "fused non-aromatic heterocyclic group" may be bridged, and examples thereof include 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl and the like.

The "heterocyclic group" of the above-mentioned "optionally substituted heterocyclic group" optionally has 1 to 3 substituents at substitutable position(s). Examples of the substituent include those similar to the above-mentioned Substituent Group B. When the heterocyclic group is a "non-aromatic heterocyclic group", the substituent further includes an oxo group. When the number of the substituents is two or more, the respective substituents may be the same or different.

Examples of the above-mentioned "optionally substituted hydroxy group" include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include an "aromatic heterocyclic group" and a "non-aromatic heterocyclic group", which are exemplified as the "heterocyclic group" of the above-mentioned "optionally substituted heterocyclic group".

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group optionally have 1 to 3 substituents at substitutable position(s). When the number of the substituents is two or more, the respective substituents may be the same or different.

Examples of the substituent for the $C_{1-10}$ alkyl group, $C_{2-10}$ alkenyl group and $C_{1-6}$ alkyl-carbonyl group include those similar to the above-mentioned Substituent Group A.

Examples of the substituent for the $C_{3-10}$ cycloalkyl group, $C_{3-10}$ cycloalkenyl group, $C_{6-14}$ aryl group, $C_{7-14}$ aralkyl group and $C_{8-13}$ arylalkenyl group include those similar to the above-mentioned Substituent Group B. Examples of the substituent for the heterocyclic group include those similar to the substituent that the "heterocyclic group" of the above-mentioned "optionally substituted heterocyclic group" optionally has.

Examples of the "optionally substituted sulfanyl group" include a sulfanyl group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each optionally substituted.

Examples of the substituent include those exemplified as the substituents of the above-mentioned "optionally substituted hydroxy group".

Examples of the above-mentioned "optionally substituted amino group" include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include an "aromatic heterocyclic group" and a "non-aromatic heterocyclic group", which are exemplified as the "heterocyclic group" of the above-mentioned "optionally substituted heterocyclic group". Among them, a 5- to 7-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable position(s). When the number of the substituents is two or more, the respective substituents may be the same or different.

Examples of the substituent for the $C_{1-10}$ alkyl group and $C_{2-10}$ alkenyl group include those similar to the above-mentioned Substituent Group A.

Examples of the substituent for the $C_{3-10}$ cycloalkyl group, $C_{3-10}$ cycloalkenyl group, $C_{6-14}$ aryl group, $C_{7-14}$ aralkyl group and $C_{8-13}$ arylalkenyl group include those similar to the above-mentioned Substituent Group B. Examples of the substituent for the heterocyclic group include those similar to the substituent that the "heterocyclic group" of the above-mentioned "optionally substituted heterocyclic group" optionally has.

Examples of the "acyl group" exemplified as the substituent for the "optionally substituted amino group" include those similar to the "acyl group" below, which is exemplified as the below-mentioned "substituent" represented by $R^6$.

Examples of the "acyl group" exemplified as the "substituent" represented by $R^6$ include a group represented by the formula: —$COR^A$, —CO—$OR^A$, —$SO_3R^A$, —$S(O)_2R^A$, —$SOR^A$, —CO—$NR^AR^{B'}$, —CS—$NR^AR^{B'}$ or —S(O)$_2$NR$^{A'}$R$^{B'}$ wherein R$^A$ is a hydrogen atom, an optionally substituted hydrocarbon group or an optionally substituted heterocyclic group, R$^{A'}$ and R$^{B'}$ are the same or different and each is a hydrogen atom, an optionally substituted hydrocarbon group or an optionally substituted heterocyclic group, or R$^{A'}$ and R$^{B'}$ in combination optionally form, together with the adjacent nitrogen atom, an optionally substituted nitrogen-containing heterocycle, and the like.

Examples of the "optionally substituted hydrocarbon group" and "optionally substituted heterocyclic group" represented by R$^A$, R$^{A'}$ or R$^{B'}$ include those similar to the "optionally substituted hydrocarbon group" and "optionally substituted heterocyclic group", which are exemplified as the "substituent" represented by R$^6$.

Examples of the "nitrogen-containing heterocycle" of the "optionally substituted nitrogen-containing heterocycle" formed by R$^{A'}$ and R$^{B'}$ in combination together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable position(s). Examples of the substituent include those similar to the substituent that the "heterocyclic group" of the "optionally substituted heterocyclic group", which is exemplified as the "substituent" represented by R$^6$, optionally has. When the number of the substituents is two or more, the respective substituents may be the same or different.

Preferable examples of the "acyl group" include
(1) a formyl group;
(2) a carboxy group;
(3) a C$_{1-6}$ alkyl-carbonyl group (e.g., acetyl) optionally substituted by 1 to 3 halogen atoms;
(4) a C$_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a C$_{3-10}$ cycloalkyl-carbonyl group (e.g., cyclopropylcarbonyl, cyclopentylcarbonyl, cyclohexylcarbonyl);
(6) a C$_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
    (a) a C$_{1-6}$ alkyl group optionally substituted by 1 to 3 substituents selected from a halogen atom, a C$_{1-6}$ alkoxy group, a C$_{1-6}$ alkoxy-carbonyl group and a carboxy group, and
    (b) an amino group optionally mono- or di-substituted by C$_{1-6}$ alkoxy-carbonyl group(s);
(8) a C$_{1-6}$ alkylsulfonyl group (e.g., methylsulfonyl, ethylsulfonyl, isopropylsulfonyl) optionally substituted by 1 to 3 halogen atoms;
(9) a C$_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a C$_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a C$_{1-6}$ alkyl group optionally substituted by 1 to 3 halogen atoms; and the like.

R$^6$ is preferably a hydrogen atom.

In one embodiment, X is preferably a nitrogen atom or CH, more preferably CH.

In the formula (I), R$^1$ is a hydrogen atom or a substituent.

Examples of the "substituent" represented by R$^1$ include those similar to the "substituent" represented by R$^6$ In the formula (I), R$^2$ is a halogen atom, a cyano group, an optionally substituted C$_{1-6}$ alkyl group or an optionally substituted carbocyclic group.

In another embodiment, In the formula (I), R$^2$ is a halogen atom, a cyano group, a substituted methyl group (preferably a methyl group substituted by 1 to 3 halogen atoms), an optionally substituted C$_{2-6}$ alkyl group or an optionally substituted carbocyclic group.

In the formula (I), R$^1$ and R$^2$ in combination optionally form an optionally further substituted ring.

The "C$_{1-6}$ alkyl group" and "C$_{2-6}$ alkyl group" of the "optionally substituted C$_{1-6}$ alkyl group" and "optionally substituted C$_{2-6}$ alkyl group" represented by R$^2$ optionally have 1 to 5 (preferably 1 to 3) substituents at substitutable position(s). Examples of the substituent include the above-mentioned Substituent Group A. When the number of the substituents is plural, the respective substituents may be the same or different.

Examples of the "carbocyclic group" of the "optionally substituted carbocyclic group" represented by R$^2$ include a C$_{3-10}$ cycloalkyl group, a C$_{3-10}$ cycloalkenyl group, a C$_{4-10}$ cycloalkadienyl group and a C$_{6-14}$ aryl group. Examples of the C$_{3-10}$ cycloalkyl group, C$_{3-10}$ cycloalkenyl group, C$_{4-10}$ cycloalkadienyl group and C$_{6-14}$ aryl group include those similar to the C$_{3-10}$ cycloalkyl group, C$_{3-10}$ cycloalkenyl group, C$_{4-10}$ cycloalkadienyl group and C$_{6-14}$ aryl group, which are exemplified as the "hydrocarbon group" of the "optionally substituted hydrocarbon group" exemplified as the substituent represented by R$^6$.

The carbocyclic group optionally has 1 to 5 (preferably 1 to 3) substituents at substitutable position(s). Examples of the substituent include those similar to the above-mentioned Substituent Group B. When the carbocyclic group is a saturated or partially-saturated carbocyclic group, the substituent further includes an oxo group. When the number of the substituents is plural, the respective substituents may be the same or different.

Examples of the "ring" of the "optionally further substituted ring" formed by R$^1$ and R$^2$ in combination include a C$_{3-10}$ cycloalkene ring, a C$_{4-10}$ cycloalkadiene ring, an aromatic hydrocarbon ring, an aromatic heterocycle, and a non-aromatic heterocycle containing at least one double bond. Examples of the C$_{3-10}$ cycloalkene ring, C$_{4-10}$ cycloalkadiene ring, aromatic hydrocarbon ring, aromatic heterocycle, and non-aromatic heterocycle containing at least one double bond include rings corresponding to the C$_{3-10}$ cycloalkenyl group, C$_{4-10}$ cycloalkadienyl group and C$_{6-14}$ aryl group, which are exemplified as the "hydrocarbon group" of the "optionally substituted hydrocarbon group" exemplified as the substituent represented by R$^6$, and rings corresponding to the aromatic heterocyclic group, and non-aromatic heterocyclic group containing at least one double bond, which are exemplified as the "heterocyclic group" of the "optionally substituted heterocyclic group" exemplified as the substituent represented by R$^6$, respectively. Examples of the ring include cyclobutadiene, cyclopentadiene, cyclohexadiene, benzene, naphthalene, furan, thiophene, pyridine, pyrimidine, pyridazine, pyrrole, imidazole, pyrazole, thiazole, oxazole, oxadiazole, thiadiazole, dihydrofuran, dihydrothiophene, dihydropyridine, dihydropyrimidine, dihydropyridazine, dihydropyrrole, dihydroimidazole, dihydropyrazole and the like.

The ring optionally has 1 to 5 (preferably 1 to 3) substituents at substitutable position(s). Examples of the substituent include those similar to the above-mentioned Substituent Group B. When the carbocycle is a partially-saturated carbocycle, and when the heterocycle is a heterocycle derived from partial-saturation of the aromatic heterocyclic group, the substituent further includes an oxo group. When the number of the substituents is plural, the respective substituents may be the same or different.

$R^1$ is preferably a hydrogen atom.

$R^2$ is preferably
(1) a halogen atom (e.g., a chlorine atom),
(2) a cyano group,
(3) a $C_{1-6}$ alkyl group (e.g., methyl, isopropyl) optionally substituted (preferably substituted) by 1 to 3 halogen atoms (e.g., a fluorine atom), or
(4) a $C_{3-8}$ cycloalkyl group (e.g., cyclopropyl).

$R^2$ is more preferably
(1) a $C_{1-6}$ alkyl group (e.g., methyl, isopropyl) optionally substituted (preferably substituted) by 1 to 3 halogen atoms (e.g., a fluorine atom), or
(2) a $C_{3-8}$ cycloalkyl group (e.g., cyclopropyl).

$R^2$ is further more preferably a $C_{1-6}$ alkyl group (e.g., methyl) optionally substituted (preferably substituted) by 1 to 3 halogen atoms (e.g., a fluorine atom).

Preferably, $R^1$ and $R^2$ in combination optionally form a 5-membered heterocycle (e.g., dihydrofuran, pyrazole) optionally further substituted by $C_{1-6}$ alkyl group(s) (e.g., methyl).

More preferably, $R^1$ and $R^2$ in combination optionally form a 5-membered heterocycle (e.g., dihydrofuran).

Further more preferably, $R^1$ and $R^2$ in combination do not form a ring.

In the formula (I), $R^3$ is a hydrogen atom or a chain substituent.

Examples of the "chain substituent" represented by $R^3$ include an optionally substituted $C_{1-10}$ alkyl group, an optionally substituted $C_{2-10}$ alkenyl group and an optionally substituted $C_{2-10}$ alkynyl group. Examples of the "$C_{1-10}$ alkyl group", "$C_{2-10}$ alkenyl group" and "$C_{2-10}$ alkynyl group" of the optionally substituted $C_{1-10}$ alkyl group, optionally substituted $C_{2-10}$ alkenyl group and optionally substituted $C_{2-10}$ alkynyl group include those similar to the $C_{1-10}$ alkyl group, $C_{2-10}$ alkenyl group and $C_{2-10}$ alkynyl group, which are exemplified as the "hydrocarbon group" of the "optionally substituted hydrocarbon group" exemplified as the substituent represented by $R^6$, respectively.

The "$C_{1-10}$ alkyl group", "$C_{2-10}$ alkenyl group" and "$C_{2-10}$ alkynyl group" optionally have 1 to 5 (preferably 1 to 3) substituents at substitutable position(s). Examples of the substituent include the above-mentioned Substituent Group A. When the number of the substituents is plural, the respective substituents may be the same or different.

$R^3$ is preferably a hydrogen atom.

In the formula (I), $R^4$ is a substituent.

In the formula (I), $R^5$ is a hydrogen atom or a substituent.

Alternatively, In the formula (I), $R^4$ and $R^5$ in combination optionally form an optionally further substituted nitrogen-containing non-aromatic heterocycle.

Alternatively, in the formula (I), $R^5$ and $R^6$ in combination optionally form an optionally further substituted nitrogen-containing non-aromatic heterocycle.

Specifically, as shown in the formula (I-1), when X is $CR^6$, then $R^5$ and $R^6$ in combination optionally form, together with the nitrogen atom that $R^5$ is bonded to and the carbon atom that $R^6$ is bonded to, an optionally further substituted nitrogen-containing non-aromatic heterocycle represented by $a^2$ wherein $a^1$ is a benzene ring.

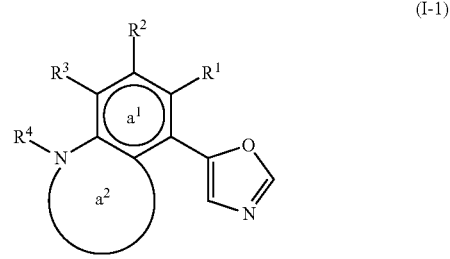

(I-1)

Examples of the "substituent" represented by $R^4$ include those similar to the "substituent" represented by $R^6$.

Examples of the "substituent" represented by $R^5$ include those similar to the "substituent" represented by $R^6$.

Examples of the "nitrogen-containing non-aromatic heterocycle" of the "optionally substituted nitrogen-containing non-aromatic heterocycle" formed by $R^4$ and $R^5$ in combination include a non-aromatic heterocycle containing at least one nitrogen atom as a ring-constituting atom. Examples of the non-aromatic heterocycle containing at least one nitrogen atom as a ring-constituting atom include rings corresponding to the non-aromatic heterocyclic group containing at least one nitrogen atom as a ring-constituting atom, form among the "non-aromatic heterocyclic group" in the "heterocyclic group" of the "optionally substituted heterocyclic group" exemplified as the substituent represented by $R^6$. Examples of the nitrogen-containing non-aromatic heterocycle include azetidine, pyrrolidine, dihydropyrrole, piperidine, morpholine, thiomorpholine, piperazine, hexamethylenimine, oxazolidine, thiazolidine, imidazolidine, oxazoline, thiazoline, dioxolane, dihydrooxadiazole, pyrazolidine, pyrazoline, tetrahydropyrimidine, dihydrotriazole, tetrahydrotriazole, 2-oxa-5-azabicyclo[2.2.1]heptane, dihydrooxazine, dihydrooxazepine, tetrahydrooxazepine and the like.

The nitrogen-containing non-aromatic heterocycle optionally has 1 to 5 (preferably 1 to 3) substituents at substitutable position(s). Examples of the substituent include those similar to the substituents that the "non-aromatic heterocyclic group" in the "heterocyclic group" of the "optionally substituted heterocyclic group" exemplified as the substituent represented by $R^6$ optionally has. When the number of the substituents is two or more, the respective substituents may be the same or different.

Examples of the "nitrogen-containing non-aromatic heterocycle" of the "optionally substituted nitrogen-containing non-aromatic heterocycle" formed by $R^5$ and $R^6$ in combination include a non-aromatic heterocycle containing at least one nitrogen atom as a ring-constituting atom and at least one double bond. Examples of the non-aromatic heterocycle containing at least one nitrogen atom as a ring-constituting atom and at least one double bond include rings corresponding to the non-aromatic heterocyclic group containing at least one nitrogen atom as a ring-constituting atom and at least one double bond, from among the "non-aromatic heterocyclic group" in the "heterocyclic group" of the "optionally substituted heterocyclic group" exemplified as the substituent represented by $R^6$ Examples of the nitrogen-containing non-aromatic heterocycle include dihydropyrrole, oxazoline, thiazoline, dihydrooxadiazole, pyrazoline, tetrahydropyrimidine, dihydrotriazole, tetrahydrotriazole, dihydrooxazine, dihydrooxazepine, tetrahydrooxazepine and the like.

The nitrogen-containing non-aromatic heterocycle optionally has 1 to 5 (preferably 1 to 3) substituents at substitutable position(s). Examples of the substituent include those similar to the substituents that the "non-aromatic heterocyclic group" in the "heterocyclic group" of the "optionally substituted heterocyclic group" exemplified as the substituent represented by $R^6$ optionally has. When the number of the substituents is two or more, the respective substituents may be the same or different.

$R^4$ is preferably
(1) a $C_{1-6}$ alkyl group (e.g., methyl) optionally substituted by 1 to 3 substituents selected from
   (a) a $C_{3-8}$ cycloalkyl group (e.g., cyclopropyl), and
   (b) a heterocyclic group (e.g., pyridyl),
(2) a $C_{1-6}$ alkyl-carbonyl group (e.g., acetyl, propionyl, butyryl, isobutyryl, 3-methylbutyryl, 3,3-dimethylbutyryl) optionally substituted by 1 to 3 substituents selected from
   (a) a halogen atom (e.g., a fluorine atom),
   (b) a $C_{3-8}$ cycloalkyl group (e.g., cyclopropyl),
   (c) a $C_{1-6}$ alkoxy group (e.g., methoxy),
   (d) a $C_{6-14}$ aryl group (e.g., phenyl) optionally substituted by 1 to 3 halogen atoms (e.g., a fluorine atom), and
   (e) a heterocyclic group (e.g., imidazolyl, pyrazolyl, furyl) optionally substituted by 1 to 3 $C_{1-6}$ alkyl groups (e.g., methyl),
(3) a $C_{1-6}$ alkoxy-carbonyl group (e.g., tert-butoxycarbonyl),
(4) a $C_{3-8}$ cycloalkyl-carbonyl group (e.g., cyclopropylcarbonyl, cyclobutylcarbonyl, cyclopentylcarbonyl, cyclohexylcarbonyl) optionally substituted by 1 to 3 substituents selected from
   (a) a hydroxy group,
   (b) a halogen atom (e.g., a fluorine atom),
   (c) a cyano group, and
   (d) a $C_{1-6}$ alkyl group (e.g., methyl),
(5) a $C_{6-14}$ aryl-carbonyl group (e.g., benzoyl) optionally substituted by 1 to 3 substituents selected from
   (a) a halogen atom (e.g., a chlorine atom), and
   (b) a $C_{1-6}$ alkoxy group (e.g., methoxy),
(6) a heterocyclylcarbonyl group (e.g., azetidinylcarbonyl, oxetanylcarbonyl, pyrrolidinylcarbonyl, thienylcarbonyl, furylcarbonyl, piperidylcarbonyl, pyridylcarbonyl, morpholinylcarbonyl, tetrahydropyranylcarbonyl, 2-oxa-5-azabicyclo[2.2.1]heptylcarbonyl, 3-oxa-6-azabicyclo[3.1.1]heptylcarbonyl, 3-oxa-8-azabicyclo[3.2.1]octylcarbonyl) optionally substituted by 1 to 3 substituents selected from
   (a) a halogen atom (e.g., a fluorine atom),
   (b) a $C_{1-6}$ alkyl group (e.g., methyl) optionally substituted by 1 to 3 $C_{6-14}$ aryl groups (e.g., phenyl), and
   (c) an oxo group,
(7) a $C_{3-8}$ cycloalkylsulfonyl group (e.g., cyclopropylsulfonyl),
(8) a $C_{6-14}$ arylsulfonyl group (e.g., phenylsulfonyl) optionally substituted by 1 to 3 halogen atoms (e.g., a chlorine atom), or
(9) a carbamoyl group optionally mono- or di-substituted by $C_{1-6}$ alkyl group(s) (e.g., ethyl).

$R^4$ is more preferably
(1) a $C_{1-6}$ alkyl group (e.g., methyl) optionally substituted by 1 to 3 heterocyclic groups (e.g., pyridyl),
(2) a $C_{1-6}$ alkyl-carbonyl group (e.g., acetyl, isobutyryl) optionally substituted by 1 to 3 heterocyclic groups (e.g., imidazolyl),
(3) a $C_{3-8}$ cycloalkyl-carbonyl group (e.g., cyclopropylcarbonyl),
(4) a $C_{6-14}$ aryl-carbonyl group (e.g., benzoyl) optionally substituted by 1 to 3 halogen atoms (e.g., a chlorine atom),
(5) a heterocyclylcarbonyl group (e.g., morpholinylcarbonyl, tetrahydropyranylcarbonyl, 2-oxa-5-azabicyclo[2.2.1]heptylcarbonyl), or
(6) a $C_{6-14}$ arylsulfonyl group (e.g., phenylsulfonyl) optionally substituted by 1 to 3 halogen atoms (e.g., a chlorine atom).

$R^4$ is further more preferably
(1) a $C_{3-8}$ cycloalkyl-carbonyl group (e.g., cyclopropylcarbonyl), or
(2) a heterocyclylcarbonyl group (e.g., tetrahydropyranylcarbonyl, morpholinylcarbonyl, preferably tetrahydropyranylcarbonyl).

$R^5$ is preferably a hydrogen atom.

Preferably, $R^4$ and $R^5$ in combination optionally form a nitrogen-containing non-aromatic heterocycle (e.g., pyrrolidine, imidazolidine, dihydropyridine, piperidine, piperazine, morpholine, 2-oxa-5-azabicyclo[2.2.1]heptane) optionally substituted by 1 to 3 substituents selected from
(1) a hydroxy group,
(2) a halogen atom (e.g., a fluorine atom),
(3) a $C_{1-6}$ alkyl group (e.g., methyl, ethyl) optionally substituted by $C_{6-14}$ aryl group(s) (e.g., phenyl) optionally substituted by 1 to 3 $C_{1-6}$ alkoxy groups (e.g., methoxy),
(4) a $C_{1-6}$ alkoxy group (e.g., methoxy) optionally substituted by 1 to 3 $C_{6-14}$ aryl groups (e.g., phenyl),
(5) a $C_{1-6}$ alkyl-carbonyl group (e.g., acetyl),
(6) a $C_{1-6}$ alkoxy-carbonyl group (e.g., tert-butoxycarbonyl),
(7) a $C_{1-6}$ alkylsulfonyl group (e.g., methylsulfonyl),
(8) an amino group optionally mono- or di-substituted by substituent(s) selected from
   (a) a $C_{1-6}$ alkyl-carbonyl group (e.g., acetyl), and
   (b) a $C_{1-6}$ alkylsulfonyl group (e.g., methylsulfonyl),
(9) an azido group, and
(10) an oxo group.

More preferably, $R^4$ and $R^5$ in combination optionally form a nitrogen-containing non-aromatic heterocycle (e.g., pyrrolidine, piperidine, piperazine) optionally substituted by 1 to 3 substituents selected from
(1) a hydroxy group,
(2) a halogen atom (e.g., a fluorine atom),
(3) a $C_{1-6}$ alkyl group (e.g., methyl) optionally substituted by $C_{6-14}$ aryl group(s) (e.g., phenyl),
(4) a $C_{1-6}$ alkyl-carbonyl group (e.g., acetyl),
(5) a $C_{1-6}$ alkylsulfonyl group (e.g., methylsulfonyl), and
(6) an oxo group.

Further more preferably, $R^4$ and $R^5$ in combination optionally form a nitrogen-containing non-aromatic heterocycle (e.g., pyrrolidine) optionally substituted by 1 to 3 hydroxy groups.

Particularly preferably, $R^4$ and $R^5$ in combination do not form a ring.

Preferably, $R^5$ and $R^6$ in combination optionally form a nitrogen-containing non-aromatic heterocycle (e.g., dihydropyrrole, dihydrooxazine, tetrahydrooxazepine) optionally substituted by one oxo group.

More preferably, $R^5$ and $R^6$ in combination optionally form a nitrogen-containing non-aromatic heterocycle (e.g., dihydropyrrole, dihydrooxazine, tetrahydrooxazepine).

Further more preferably, $R^5$ and $R^6$ in combination optionally form a 5-membered nitrogen-containing non-aromatic heterocycle (e.g., dihydropyrrole).

Preferable examples of compound (I) include the following compounds.

[Compound A-1]
Compound (I) wherein
X is a nitrogen atom or $CR^6$;
$R^1$ is a hydrogen atom;
$R^2$ is a halogen atom, a cyano group, an optionally substituted $C_{1-6}$ alkyl group or an optionally substituted carbocyclic group; or
$R^1$ and $R^2$ in combination optionally form an optionally further substituted ring;
$R^3$ is a hydrogen atom;
$R^4$ is a substituent;
$R^5$ is a hydrogen atom; and
$R^6$ is a hydrogen atom; or
$R^4$ and $R^5$ in combination optionally form an optionally further substituted nitrogen-containing non-aromatic heterocycle; or
$R^5$ and $R^6$ in combination optionally form an optionally further substituted nitrogen-containing non-aromatic heterocycle, provided that 4-methyl-N-(3-methyl-5-(1,3-oxazol-5-yl)phenyl)benzenesulfonamide, and 4-methoxy-N-(3-methyl-5-(1,3-oxazol-5-yl)phenyl)benzenesulfonamide are excluded.

[Compound A-2]
Compound (I) wherein
X is a nitrogen atom or $CR^6$;
$R^1$ is a hydrogen atom;
$R^2$ is a halogen atom, a cyano group, a substituted methyl group, an optionally substituted $C_{2-6}$ alkyl group or an optionally substituted carbocyclic group; or
$R^1$ and $R^2$ in combination optionally form an optionally further substituted ring;
$R^3$ is a hydrogen atom;
$R^4$ is a substituent;
$R^5$ is a hydrogen atom; and
$R^6$ is a hydrogen atom; or
$R^4$ and $R^5$ in combination optionally form an optionally further substituted nitrogen-containing non-aromatic heterocycle; or
$R^5$ and $R^6$ in combination optionally form an optionally further substituted nitrogen-containing non-aromatic heterocycle.

[Compound B-1]
Compound (I) wherein
X is a nitrogen atom or $CR^6$;
$R^1$ is a hydrogen atom;
$R^2$ is
(1) a halogen atom (e.g., a chlorine atom),
(2) a cyano group,
(3) a $C_{1-6}$ alkyl group (e.g., methyl, isopropyl) optionally substituted by 1 to 3 halogen atoms (e.g., a fluorine atom), or
(4) a $C_{3-8}$ cycloalkyl group (e.g., cyclopropyl); or
$R^1$ and $R^2$ in combination optionally form a 5-membered heterocycle (e.g., dihydrofuran, pyrazole) optionally further substituted by $C_{1-6}$ alkyl group(s) (e.g., methyl);
$R^3$ is a hydrogen atom;
$R^4$ is
(1) a $C_{1-6}$ alkyl group (e.g., methyl) optionally substituted by 1 to 3 substituents selected from
  (a) a $C_{3-8}$ cycloalkyl group (e.g., cyclopropyl), and
  (b) a heterocyclic group (e.g., pyridyl),
(2) a $C_{1-6}$ alkyl-carbonyl group (e.g., acetyl, propionyl, butyryl, isobutyryl, 3-methylbutyryl, 3,3-dimethylbutyryl) optionally substituted by 1 to 3 substituents selected from
  (a) a halogen atom (e.g., a fluorine atom),
  (b) a $C_{3-8}$ cycloalkyl group (e.g., cyclopropyl),
  (c) a alkoxy group (e.g., methoxy),
  (d) a $C_{6-14}$ aryl group (e.g., phenyl) optionally substituted by 1 to 3 halogen atoms (e.g., a fluorine atom), and
  (e) a heterocyclic group (e.g., imidazolyl, pyrazolyl, furyl) optionally substituted by 1 to 3 $C_{1-6}$ alkyl groups (e.g., methyl),
(3) a $C_{1-6}$ alkoxy-carbonyl group (e.g., tert-butoxycarbonyl),
(4) a $C_{3-8}$ cycloalkyl-carbonyl group (e.g., cyclopropylcarbonyl, cyclobutylcarbonyl, cyclopentylcarbonyl, cyclohexylcarbonyl) optionally substituted by 1 to 3 substituents selected from
  (a) a hydroxy group,
  (b) a halogen atom (e.g., a fluorine atom),
  (c) a cyano group, and
  (d) a $C_{1-6}$ alkyl group (e.g., methyl),
(5) a $C_{6-14}$ aryl-carbonyl group (e.g., benzoyl) optionally substituted by 1 to 3 substituents selected from
  (a) a halogen atom (e.g., a chlorine atom), and
  (b) a $C_{1-6}$ alkoxy group (e.g., methoxy),
(6) a heterocyclylcarbonyl group (e.g., azetidinylcarbonyl, oxetanylcarbonyl, pyrrolidinylcarbonyl, thienylcarbonyl, furylcarbonyl, piperidylcarbonyl, pyridylcarbonyl, morpholinylcarbonyl, tetrahydropyranylcarbonyl, 2-oxa-5-azabicyclo[2.2.1]heptylcarbonyl, 3-oxa-6-azabicyclo[3.1.1]heptylcarbonyl, 3-oxa-8-azabicyclo[3.2.1]octylcarbonyl) optionally substituted by 1 to 3 substituents selected from
  (a) a halogen atom (e.g., a fluorine atom),
  (b) a $C_{1-6}$ alkyl group (e.g., methyl) optionally substituted by 1 to 3 $C_{6-14}$ aryl groups (e.g., phenyl), and
  (c) an oxo group,
(7) a $C_{3-8}$ cycloalkylsulfonyl group (e.g., cyclopropylsulfonyl),
(8) a $C_{6-14}$ arylsulfonyl group (e.g., phenylsulfonyl) optionally substituted by 1 to 3 halogen atoms (e.g., a chlorine atom), or
(9) a carbamoyl group optionally mono- or di-substituted by $C_{1-6}$ alkyl group(s) (e.g., ethyl);
$R^5$ is a hydrogen atom; and
$R^6$ is a hydrogen atom; or
$R^4$ and $R^5$ in combination optionally forma nitrogen-containing non-aromatic heterocycle (e.g., pyrrolidine, imidazolidine, dihydropyridine, piperidine, piperazine, morpholine, 2-oxa-5-azabicyclo[2.2.1]heptane) optionally substituted by 1 to 3 substituents selected from
  (1) a hydroxy group,
  (2) a halogen atom (e.g., a fluorine atom),
  (3) a $C_{1-6}$ alkyl group (e.g., methyl, ethyl) optionally substituted by $C_{6-14}$ aryl group(s) (e.g., phenyl) optionally substituted by 1 to 3 $C_{1-6}$ alkoxy groups (e.g., methoxy),
  (4) a $C_{1-6}$ alkoxy group (e.g., methoxy) optionally substituted by 1 to 3 $C_{6-14}$ aryl groups (e.g., phenyl),
  (5) a $C_{1-6}$ alkyl-carbonyl group (e.g., acetyl),
  (6) a $C_{1-6}$ alkoxy-carbonyl group (e.g., tert-butoxycarbonyl),
  (7) a $C_{1-6}$ alkylsulfonyl group (e.g., methylsulfonyl),
  (8) an amino group optionally mono- or di-substituted by substituent(s) selected from
    (a) a $C_{1-6}$ alkyl-carbonyl group (e.g., acetyl), and
    (b) a $C_{1-6}$ alkylsulfonyl group (e.g., methylsulfonyl),
  (9) an azido group, and
  (10) an oxo group; or
$R^5$ and $R^6$ in combination optionally form a nitrogen-containing non-aromatic heterocycle (e.g., dihydropyrrole, dihydrooxazine, tetrahydrooxazepine) optionally substituted by one oxo group.

[Compound B-2]
Compound (I) wherein
X is a nitrogen atom or $CR^6$;
$R^1$ is a hydrogen atom;
$R^2$ is
(1) a halogen atom (e.g., a chlorine atom),
(2) a cyano group,
(3) a $C_{1-6}$ alkyl group (e.g., methyl, isopropyl) optionally substituted by 1 to 3 halogen atoms (e.g., a fluorine atom), or
(4) a $C_{3-8}$ cycloalkyl group (e.g., cyclopropyl); or
$R^1$ and $R^2$ in combination optionally form a dihydrofuran ring or a pyrazole ring, each optionally further substituted by $C_{1-6}$ alkyl group(s) (e.g., methyl);
$R^3$ is a hydrogen atom;
$R^4$ is
(1) a $C_{1-6}$ alkyl group (e.g., methyl) optionally substituted by 1 to 3 substituents selected from
    (a) a $C_{1-8}$ cycloalkyl group (e.g., cyclopropyl), and
    (b) a pyridyl group,
(2) a $C_{1-6}$ alkyl-carbonyl group (e.g., acetyl, propionyl, butyryl, isobutyryl, 3-methylbutyryl, 3,3-dimethylbutyryl) optionally substituted by 1 to 3 substituents selected from
    (a) a halogen atom (e.g., a fluorine atom),
    (b) a $C_{3-8}$ cycloalkyl group (e.g., cyclopropyl),
    (c) a $C_{1-6}$ alkoxy group (e.g., methoxy),
    (d) a $C_{6-14}$ aryl group (e.g., phenyl) optionally substituted by 1 to 3 halogen atoms (e.g., a fluorine atom), and
    (e) an imidazolyl group, a pyrazolyl group and a furyl group, each optionally substituted by 1 to 3 $C_{1-6}$ alkyl groups (e.g., methyl),
(3) a $C_{1-6}$ alkoxy-carbonyl group (e.g., tert-butoxycarbonyl),
(4) a $C_{3-8}$ cycloalkyl-carbonyl group (e.g., cyclopropylcarbonyl, cyclobutylcarbonyl, cyclopentylcarbonyl, cyclohexylcarbonyl) optionally substituted by 1 to 3 substituents selected from
    (a) a hydroxy group,
    (b) a halogen atom (e.g., a fluorine atom),
    (c) a cyano group, and
    (d) a $C_{1-6}$ alkyl group (e.g., methyl),
(5) a $C_{6-14}$ aryl-carbonyl group (e.g., benzoyl) optionally substituted by 1 to 3 substituents selected from
    (a) a halogen atom (e.g., a chlorine atom), and
    (b) a $C_{1-6}$ alkoxy group (e.g., methoxy),
(6) an azetidinylcarbonyl group, an oxetanylcarbonyl group, a pyrrolidinylcarbonyl group, a thienylcarbonyl group, a furylcarbonyl group, a piperidylcarbonyl group, a pyridylcarbonyl group, a morpholinylcarbonyl group, a tetrahydropyranylcarbonyl group, a 2-oxa-5-azabicyclo[2.2.1]heptylcarbonyl group, a 3-oxa-6-azabicyclo[3.1.1]heptylcarbonyl group or a 3-oxa-8-azabicyclo[3.2.1]octylcarbonyl group, each optionally substituted by 1 to 3 substituents selected from
    (a) a halogen atom (e.g., a fluorine atom),
    (b) a $C_{1-6}$ alkyl group (e.g., methyl) optionally substituted by 1 to 3 $C_{6-14}$ aryl groups (e.g., phenyl), and
    (c) an oxo group,
(7) a $C_{3-8}$ cycloalkylsulfonyl group (e.g., cyclopropylsulfonyl),
(8) a $C_{6-14}$ arylsulfonyl group (e.g., phenylsulfonyl) optionally substituted by 1 to 3 halogen atoms (e.g., a chlorine atom), or
(9) a carbamoyl group optionally mono- or di-substituted by $C_{1-6}$ alkyl group(s) (e.g., ethyl);
$R^5$ is a hydrogen atom; and
$R^6$ is a hydrogen atom; or
$R^4$ and $R^5$ in combination optionally form a pyrrolidine ring, an imidazolidine ring, a dihydropyridine ring, a piperidine ring, a piperazine ring, a morpholine ring or a 2-oxa-5-azabicyclo[2.2.1]heptane ring, each optionally substituted by 1 to 3 substituents selected from
    (1) a hydroxy group,
    (2) a halogen atom (e.g., a fluorine atom),
    (3) a $C_{1-6}$ alkyl group (e.g., methyl, ethyl) optionally substituted by $C_{5-14}$ aryl group(s) (e.g., phenyl) optionally substituted by 1 to 3 $C_{1-6}$ alkoxy groups (e.g., methoxy),
    (4) a $C_{1-6}$ alkoxy group (e.g., methoxy) optionally substituted by 1 to 3 $C_{6-14}$ aryl groups (e.g., phenyl),
    (5) a $C_{1-6}$ alkyl-carbonyl group (e.g., acetyl),
    (6) a $C_{1-6}$ alkoxy-carbonyl group (e.g., tert-butoxycarbonyl),
    (7) a $C_{1-6}$ alkylsulfonyl group (e.g., methylsulfonyl),
    (8) an amino group optionally mono- or di-substituted by substituent(s) selected from
        (a) a $C_{1-6}$ alkyl-carbonyl group (e.g., acetyl), and
        (b) a $C_{1-6}$ alkylsulfonyl group (e.g., methylsulfonyl),
    (9) an azido group, and
    (10) an oxo group; or
$R^5$ and $R^6$ in combination optionally form a dihydropyrrole ring, a dihydrooxazine ring or a tetrahydrooxazepine ring, each optionally substituted by one oxo group.
[Compound B-3]
Compound (I) wherein
X is a nitrogen atom or $CR^6$;
$R^1$ is a hydrogen atom;
$R^2$ is
(1) a halogen atom (e.g., a chlorine atom),
(2) a cyano group,
(3) a $C_{1-6}$ alkyl group (e.g., methyl, isopropyl) optionally substituted by 1 to 3 halogen atoms (e.g., a fluorine atom), or
(4) a cyclopropyl group; or
$R^1$ and $R^2$ in combination optionally form a dihydrofuran ring or a pyrazole ring, each optionally further substituted by $C_{1-6}$ alkyl group(s) (e.g., methyl);
$R^3$ is a hydrogen atom;
$R^4$ is
(1) a $C_{1-6}$ alkyl group (e.g., methyl) optionally substituted by 1 to 3 substituents selected from
    (a) a cyclopropyl group, and
    (b) a pyridyl group,
(2) a $C_{1-6}$ alkyl-carbonyl group (e.g., acetyl, propionyl, butyryl, isobutyryl, 3-methylbutyryl, 3,3-dimethylbutyryl) optionally substituted by 1 to 3 substituents selected from
    (a) a halogen atom (e.g., a fluorine atom),
    (b) a cyclopropyl group,
    (c) a $C_{1-6}$ alkoxy group (e.g., methoxy),
    (d) a phenyl group optionally substituted by 1 to 3 halogen atoms (e.g., a fluorine atom), and
    (e) an imidazolyl group, a pyrazolyl group and a furyl group, each optionally substituted by 1 to 3 $C_{1-6}$ alkyl groups (e.g., methyl),
(3) a $C_{1-6}$ alkoxy-carbonyl group (e.g., tert-butoxycarbonyl),
(4) a cyclopropylcarbonyl group, a cyclobutylcarbonyl group, a cyclopentylcarbonyl group or a cyclohexylcarbonyl group, each optionally substituted by 1 to 3 substituents selected from
    (a) a hydroxy group,
    (b) a halogen atom (e.g., a fluorine atom),
    (c) a cyano group, and
    (d) a $C_{1-6}$ alkyl group (e.g., methyl), (5) a benzoyl group optionally substituted by 1 to 3 substituents selected from
  (a) a halogen atom (e.g., a chlorine atom), and
  (b) a $C_{1-6}$ alkoxy group (e.g., methoxy),
(6) an azetidinylcarbonyl group, an oxetanylcarbonyl group, a pyrrolidinylcarbonyl group, a thienylcarbonyl group, a furylcarbonyl group, a piperidylcarbonyl group, a pyridylcarbonyl group, a morpholinylcarbonyl group, a tetrahydropyranylcarbonyl group, a 2-oxa-5-azabicyclo[2.2.1]heptylcarbonyl group, a 3-oxa-6-azabicyclo[3.1.1]heptylcarbonyl group or a 3-oxa-8-azabicyclo[3.2.1]octylcarbonyl group, each optionally substituted by 1 to 3 substituents selected from
  (a) a halogen atom (e.g., a fluorine atom),
  (b) a $C_{1-6}$ alkyl group optionally substituted by 1 to 3 phenyl groups (e.g., methyl), and
  (c) an oxo group,
(7) a cyclopropylsulfonyl group,
(8) a phenylsulfonyl group optionally substituted by 1 to 3 halogen atoms (e.g., a chlorine atom), or
(9) a carbamoyl group optionally mono- or di-substituted by $C_{1-6}$ alkyl group(s) (e.g., ethyl);
$R^5$ is a hydrogen atom; and
$R^6$ is a hydrogen atom; or
$R^4$ and $R^5$ in combination optionally form a pyrrolidine ring, an imidazolidine ring, a dihydropyridine ring, a piperidine ring, a piperazine ring, a morpholine ring or a 2-oxa-5-azabicyclo[2.2.1]heptane ring, each optionally substituted by 1 to 3 substituents selected from
  (1) a hydroxy group,
  (2) a halogen atom (e.g., a fluorine atom),
  (3) a $C_{1-6}$ alkyl group (e.g., methyl, ethyl) optionally substituted by phenyl group(s) optionally substituted by 1 to 3 $C_{1-6}$ alkoxy groups (e.g., methoxy),
  (4) a $C_{1-6}$ alkoxy group optionally substituted by 1 to 3 phenyl groups (e.g., methoxy),
  (5) a $C_{1-6}$ alkyl-carbonyl group (e.g., acetyl),
  (6) a $C_{1-6}$ alkoxy-carbonyl group (e.g., tert-butoxycarbonyl),
  (7) a $C_{1-6}$ alkylsulfonyl group (e.g., methylsulfonyl),
  (8) an amino group optionally mono- or di-substituted by substituent(s) selected from
    (a) a $C_{1-6}$ alkyl-carbonyl group (e.g., acetyl), and
    (b) a $C_{1-6}$ alkylsulfonyl group (e.g., methylsulfonyl),
  (9) an azido group, and
  (10) an oxo group; or
$R^5$ and $R^6$ in combination optionally form a dihydropyrrole ring, a dihydrooxazine ring or a tetrahydrooxazepine ring, each optionally substituted by one oxo group.
[Compound C-1]
Compound (I) wherein
X is a nitrogen atom or $CR^6$;
$R^1$ is a hydrogen atom;
$R^2$ is
(1) a $C_{1-6}$ alkyl group (e.g., methyl, isopropyl) optionally substituted by 1 to 3 halogen atoms (e.g., a fluorine atom), or
(2) a $C_{3-8}$ cycloalkyl group (e.g., cyclopropyl); or
$R^1$ and $R^2$ in combination optionally form a 5-membered heterocycle (e.g., dihydrofuran);
$R^3$ is a hydrogen atom;
$R^4$ is
(1) a $C_{1-6}$ alkyl group (e.g., methyl) optionally substituted by 1 to 3 heterocyclic groups (e.g., pyridyl),
(2) a $C_{1-6}$ alkyl-carbonyl group (e.g., acetyl, isobutyryl) optionally substituted by 1 to 3 heterocyclic groups (e.g., imidazolyl),
(3) a $C_{3-8}$ cycloalkyl-carbonyl group (e.g., cyclopropylcarbonyl),
(4) a $C_{6-14}$ aryl-carbonyl group (e.g., benzoyl) optionally substituted by 1 to 3 halogen atoms (e.g., a chlorine atom),
(5) a heterocyclylcarbonyl group (e.g., morpholinylcarbonyl, tetrahydropyranylcarbonyl, 2-oxa-5-azabicyclo[2.2.1]heptylcarbonyl), or
(6) a $C_{6-14}$ arylsulfonyl group (e.g., phenylsulfonyl) optionally substituted by 1 to 3 halogen atoms (e.g., a chlorine atom);
$R^5$ is a hydrogen atom; and
$R^6$ is a hydrogen atom; or
$R^4$ and $R^5$ in combination optionally form a nitrogen-containing non-aromatic heterocycle (e.g., pyrrolidine, piperidine, piperazine) optionally substituted by 1 to 3 substituents selected from
  (1) a hydroxy group,
  (2) a halogen atom (e.g., a fluorine atom),
  (3) a $C_{1-6}$ alkyl group (e.g., methyl) optionally substituted by $C_{6-14}$ aryl group (s) (e.g., phenyl),
  (4) a $C_{1-6}$ alkyl-carbonyl group (e.g., acetyl),
  (5) an amino group optionally mono- or di-substituted by $C_{1-6}$ alkylsulfonyl group(s) (e.g., methylsulfonyl), and
  (6) an oxo group; or
$R^5$ and $R^6$ in combination optionally form a nitrogen-containing non-aromatic heterocycle (e.g., dihydropyrrole, dihydrooxazine, tetrahydrooxazepine).
[Compound C-2]
Compound (I) wherein
X is a nitrogen atom or $CR^6$;
$R^1$ is a hydrogen atom;
$R^2$ is
(1) a $C_{1-6}$ alkyl group (e.g., methyl, isopropyl) optionally substituted by 1 to 3 halogen atoms (e.g., a fluorine atom), or
(2) a cyclopropyl group; or
$R^1$ and $R^2$ in combination optionally form a dihydrofuran ring;
$R^3$ is a hydrogen atom;
$R^4$ is
(1) a $C_{1-6}$ alkyl group (e.g., methyl) optionally substituted by 1 to 3 pyridyl groups,
(2) a $C_{1-6}$ alkyl-carbonyl group (e.g., acetyl, isobutyryl) optionally substituted by 1 to 3 imidazolyl groups,
(3) a cyclopropylcarbonyl group,
(4) a benzoyl group optionally substituted by 1 to 3 halogen atoms (e.g., a chlorine atom),
(5) a morpholinylcarbonyl group, a tetrahydropyranylcarbonyl group or a 2-oxa-5-azabicyclo[2.2.1]heptylcarbonyl group, or
(6) a phenylsulfonyl group optionally substituted by 1 to 3 halogen atoms (e.g., a chlorine atom);
$R^5$ is a hydrogen atom; and
$R^6$ is a hydrogen atom; or
$R^4$ and $R^5$ in combination optionally form a pyrrolidine ring, a piperidine ring or a piperazine ring, each optionally substituted by 1 to 3 substituents selected from
  (1) a hydroxy group,
  (2) a halogen atom (e.g., a fluorine atom),
  (3) a $C_{1-6}$ alkyl group (e.g., methyl) optionally substituted by phenyl group(s),
  (4) a $C_{1-6}$ alkyl-carbonyl group (e.g., acetyl),
  (5) an amino group optionally mono- or di-substituted by $C_{1-6}$ alkylsulfonyl group(s) (e.g., methylsulfonyl), and
  (6) an oxo group; or
$R^5$ and $R^6$ in combination optionally form a dihydropyrrole ring, a dihydrooxazine ring or a tetrahydrooxazepine ring.

[Compound D-1]
Compound (I) wherein
X is $CR^6$;
$R^1$ is a hydrogen atom;
$R^2$ is a $C_{1-6}$ alkyl group (e.g., methyl) optionally substituted by 1 to 3 halogen atoms (e.g., a fluorine atom);
$R^3$ is a hydrogen atom;
$R^4$ is
(1) a $C_{3-8}$ cycloalkyl-carbonyl group (e.g., cyclopropylcarbonyl), or
(2) a heterocyclylcarbonyl group (e.g., tetrahydropyranylcarbonyl);
$R^5$ is a hydrogen atom; and
$R^6$ is a hydrogen atom; or
$R^4$ and $R^5$ in combination optionally form a nitrogen-containing non-aromatic heterocycle (e.g., pyrrolidine) optionally substituted by 1 to 3 hydroxy groups; or
$R^5$ and $R^6$ in combination optionally form a 5-membered nitrogen-containing non-aromatic heterocycle (e.g., dihydropyrrole).

[Compound D-2]
Compound (I) wherein
X is $CR^6$;
$R^1$ is a hydrogen atom;
$R^2$ is a $C_{1-6}$ alkyl group (e.g., methyl) optionally substituted by 1 to 3 halogen atoms (e.g., a fluorine atom);
$R^3$ is a hydrogen atom;
$R^4$ is
(1) a cyclopropylcarbonyl group, or
(2) a tetrahydropyranylcarbonyl group;
$R^5$ is a hydrogen atom; and
$R^6$ is a hydrogen atom; or
$R^4$ and $R^5$ in combination optionally form a pyrrolidine ring optionally substituted by 1 to 3 hydroxy groups; or
$R^5$ and $R^6$ in combination optionally form a dihydropyrrole ring.

[Compound E-1]
Compound (I) wherein
X is a nitrogen atom or $CR^6$;
$R^1$ is a hydrogen atom;
$R^2$ is a $C_{1-6}$ alkyl group (e.g., methyl) optionally substituted by 1 to 3 halogen atoms (e.g., a fluorine atom);
$R^3$ is a hydrogen atom;
$R^4$ is
(1) a $C_{3-6}$ cycloalkyl-carbonyl group (e.g., cyclopropylcarbonyl), or
(2) a heterocyclylcarbonyl group (e.g., tetrahydropyranylcarbonyl, morpholinylcarbonyl, preferably tetrahydropyranylcarbonyl);
$R^5$ is a hydrogen atom; and
$R^6$ is a hydrogen atom; or
$R^5$ and $R^6$ in combination optionally form a 5-membered nitrogen-containing non-aromatic heterocycle (e.g., dihydropyrrole).

[Compound E-2]
Compound (I) wherein
X is a nitrogen atom or $CR^6$;
$R^1$ is a hydrogen atom;
$R^2$ is a $C_{1-6}$ alkyl group (e.g., methyl) optionally substituted by 1 to 3 halogen atoms (e.g., a fluorine atom);
$R^3$ is a hydrogen atom;
$R^4$ is
(1) a cyclopropylcarbonyl group, or
(2) a tetrahydropyranylcarbonyl group or a morpholinylcarbonyl group;
$R^5$ is a hydrogen atom; and
$R^6$ is a hydrogen atom; or
$R^5$ and $R^6$ in combination optionally form a dihydropyrrole ring.

[Compound E-3]
Compound (I) wherein
X is a nitrogen atom or $CR^6$;
$R^1$ is a hydrogen atom;
$R^2$ is a $C_{1-6}$ alkyl group (e.g., methyl) substituted by 1 to 3 halogen atoms (e.g., a fluorine atom);
$R^3$ is a hydrogen atom;
$R^4$ is
(1) a cyclopropylcarbonyl group, or
(2) a tetrahydropyranylcarbonyl group or a morpholinylcarbonyl group;
$R^5$ is a hydrogen atom; and
$R^6$ is a hydrogen atom; or
$R^5$ and $R^6$ in combination optionally form a dihydropyrrole ring.

[Compound F-1]
Compound (I) wherein
X is a nitrogen atom or $CR^6$;
$R^1$ is a hydrogen atom;
$R^2$ is a $C_{1-6}$ alkyl group (e.g., methyl) optionally substituted by 1 to 3 halogen atoms (e.g., a fluorine atom);
$R^3$ is a hydrogen atom;
$R^4$ is
(1) a cyclopropylcarbonyl group, or
(2) a tetrahydropyranylcarbonyl group;
$R^5$ is a hydrogen atom; and
$R^6$ is a hydrogen atom; or
$R^5$ and $R^6$ in combination optionally form a dihydropyrrole ring.

[Compound F-2]
Compound (I) wherein
X is a nitrogen atom or $CR^6$;
$R^1$ is a hydrogen atom;
$R^2$ is a $C_{1-6}$ alkyl group (e.g., methyl) substituted by 1 to 3 halogen atoms (e.g., a fluorine atom);
$R^3$ is a hydrogen atom;
$R^4$ is
(1) a cyclopropylcarbonyl group, or
(2) a tetrahydropyranylcarbonyl group;
$R^5$ is a hydrogen atom; and
$R^6$ is a hydrogen atom; or
$R^5$ and $R^6$ in combination optionally form a dihydropyrrole ring.

[Compound G-1]
cyclopropyl(4-(1,3-oxazol-5-yl)-6-(trifluoromethyl)-2,3-dihydro-1H-indol-1-yl)methanone or a salt thereof,
N-(6-(1,3-oxazol-5-yl)-4-(trifluoromethyl)pyridin-2-yl)cyclopropanecarboxamide or a salt thereof, or
(4-(1,3-oxazol-5-yl)-6-(trifluoromethyl)-2,3-dihydro-1H-indol-1-yl) (tetrahydro-2H-pyran-4-yl)methanone or a salt thereof.

[Compound G-2]
cyclopropyl(4-(1,3-oxazol-5-yl)-6-(trifluoromethyl)-2,3-dihydro-1H-indol-1-yl)methanone or a salt thereof.

[Compound G-3]
N-(6-(1,3-oxazol-5-yl)-4-(trifluoromethyl)pyridin-2-yl)cyclopropanecarboxamide or a salt thereof.

[Compound G-4]
(4-(1,3-oxazol-5-yl)-6-(trifluoromethyl)-2,3-dihydro-1H-indol-1-yl) (tetrahydro-2H-pyran-4-yl)methanone or a salt thereof.

When compound (I) is in a form of a salt, examples thereof include metal salts, an ammonium salt, salts with organic base, salts with inorganic acid, salts with organic acid, salts with basic or acidic amino acid, and the like.

Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The compound of the present invention and the raw material compounds can be produced by a method known per se, for example, by method shown in the following scheme and the like. In the following, the "room temperature" generally means 0-40° C. and, unless otherwise specified, each symbol in the chemical formulas described in the schemes is as defined above. In the schemes, each compound includes salts, and examples of such salt include those similar to the salts of the compound of the present invention, and the like. The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the scheme is commercially available, a commercially available product can also be used directly. When each ring in the formula (I) has a substituent, the corresponding precursor also has a similar substituent.

When the raw material compound has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). Preferable examples of the protecting group include a tert-butylcarbamate group, a benzylcarbamate group, a benzyl group, a methyl group, an ethyl group, a tert-butyl group, a trimethylsilyl group, a triethylsilyl group, a tert-butyldimethylsilyl group, a tert-butyldiphenylsilyl group, a triisopropylsilyl group and the like.

The following each step can be performed without solvent, or by dissolving or suspending raw material compound in a suitable solvent prior to the reaction. In this case, solvent may be used alone, or two or more kinds of these solvents may be mixed in an appropriate ratio and used. Specific examples of the solvent used for the production method of the compound of the present invention include the followings.

alcohols: methanol, ethanol, 1-propanol, 2-propanol, tert-butyl alcohol, tert-amyl alcohol, 2-methoxyethanol etc.
ethers: diethyl ether, diisopropyl ether, diphenyl ether, tetrahydrofuran, 1,4-dioxane, 1,2-dimethoxyethane etc.
aromatic hydrocarbons: benzene, chlorobenzene, toluene, xylene etc.
saturated hydrocarbons: cyclohexane, hexane etc. amides: N,N-dimethylformamide, N,N-dimethylacetamide, hexamethylphosphoric triamide, N-methylpyrrolidone etc.
halogenated hydrocarbons: dichloromethane, chloroform, carbon tetrachloride, 1,2-dichloroethane etc.
nitriles: acetonitrile, propionitrile etc.
sulfoxides: dimethylsulfoxide etc.
organic bases: triethylamine, pyridine, 2,6-lutidine etc.
acid anhydrides: acetic anhydride etc.
organic acids: formic acid, acetic acid, propionic acid, trifluoroacetic acid, methanesulfonic acid etc.
inorganic acids: hydrochloric acid, sulfuric acid etc.
esters: methyl acetate, ethyl acetate, butyl acetate etc.
ketones: acetone, methyl ethyl ketone etc.
water Specific examples of the base or acid scavenger used for the production method of the compound of the present invention include the followings.

inorganic bases: sodium hydroxide, potassium hydroxide, magnesium hydroxide etc.
basic salts: sodium carbonate, potassium carbonate, cesium carbonate, calcium carbonate, sodium hydrogen carbonate etc.
organic bases: triethylamine, diisopropylethylamine, tributylamine, cyclohexyldimethylamine, pyridine, 2,6-lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole etc.
metal alkoxides: sodium methoxide, sodium ethoxide, potassium tert-butoxide etc.
alkali metal hydrides: sodium hydride, potassium hydride etc.
metal amides: sodium amide, lithiumdiisopropylamide, lithiumhexamethyldisilazide etc.
organic lithium reagents: methyllithium, n-butyllithium, sec-butyllithium, tert-butyllithium etc.

Specific examples of the acid or acid catalyst used for the production method of the compound of the present invention include the followings.

inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acid: boron trifluoride ether complex, zinc iodide, anhydrous aluminum chloride, anhydrous zinc chloride, anhydrous iron chloride etc.

Compound (I) of the present invention can be produced according to the production method A explained below.

Unless otherwise specified, each symbol in the general formulas in the schemes is as defined above. In the formulas, $LG^1$-$LG^5$ are each a leaving group, $PG^1$ is a protecting group for the 2-position of 1,3-oxazole, $R^a$ is a hydrogen atom or an optionally substituted $C_{1-6}$ alkyl group, in the latter, two $R^a$ in combination optionally form a ring such as 4,4,5,5-tetramethyl-1,3,2-dioxaborolane and the like. In the formulas, —CH($R^7$)($R^8$) is a group corresponding to the optionally substituted $C_{1-10}$ alkyl group, optionally substituted $C_{3-10}$ alkenyl group or optionally substituted $C_{3-10}$ alkynyl group, from among the substituent represented by $R^4$, provided that the carbon atom at the 1-position is saturated, and $R^9$ is a hydrogen atom, an optionally substituted hydrocarbon group or an optionally substituted heterocyclic group.

The "$C_{1-6}$ alkyl group" of the "optionally substituted $C_{1-6}$ alkyl group" represented by $R^a$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Examples of the "$C_{1-10}$ alkyl group" of the "group corresponding to the optionally substituted $C_{1-10}$ alkyl group, optionally substituted $C_{3-10}$ alkenyl group or optionally substituted $C_{3-10}$ alkynyl group" represented by the —CH($R^7$)($R^8$) include those similar to the "$C_{1-10}$ alkyl group" exemplified as the "substituent" represented by $R^6$.

The $C_{1-10}$ alkyl group optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

The "$C_{3-10}$ alkenyl group" and the "$C_{3-10}$ alkynyl group" of the "group corresponding to the optionally substituted $C_{1-10}$ alkyl group, optionally substituted $C_{3-10}$ alkenyl group or optionally substituted $C_{3-10}$ alkynyl group" represented by —CH($R^7$)($R^8$) each optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

Examples of the "optionally substituted hydrocarbon group" and the "optionally substituted heterocyclic group" represented by $R^9$ include those similar to the "optionally substituted hydrocarbon group" and the "optionally substituted heterocyclic group", which are exemplified as the "substituent" represented by $R^6$, respectively.

Examples of the protecting group represented by $PG^1$ include a hydrogen atom, a trimethylsilyl group, a triethylsilyl group, a tert-butyldimethylsilyl group, a tert-butyldiphenylsilyl group, a triisopropylsilyl group and the like.

Examples of the "leaving group" represented by $LG^1$-$LG^5$ include a halogen atom (e.g., a fluorine atom, a chlorine atom, a bromine atom, an iodine atom, etc.), a $C_{1-6}$ alkylsulfonyloxy group (e.g., methanesulfonyloxy, ethanesulfonyloxy, trifluoromethanesulfonyloxy, etc.), a $C_{1-6}$ alkylsulfonyl group (e.g., methanesulfonyl, ethanesulfonyl, etc.) and the like. In addition, $LG^1$-$LG^5$ contain substituents convertible to a leaving group, and they are converted to a leaving group in desire step according to a method known per se. For example, when $LG^1$-$LG^5$ are each a methylthio group, it is converted to a methanesulfonyl group by oxidation reaction.

[Production Method A]

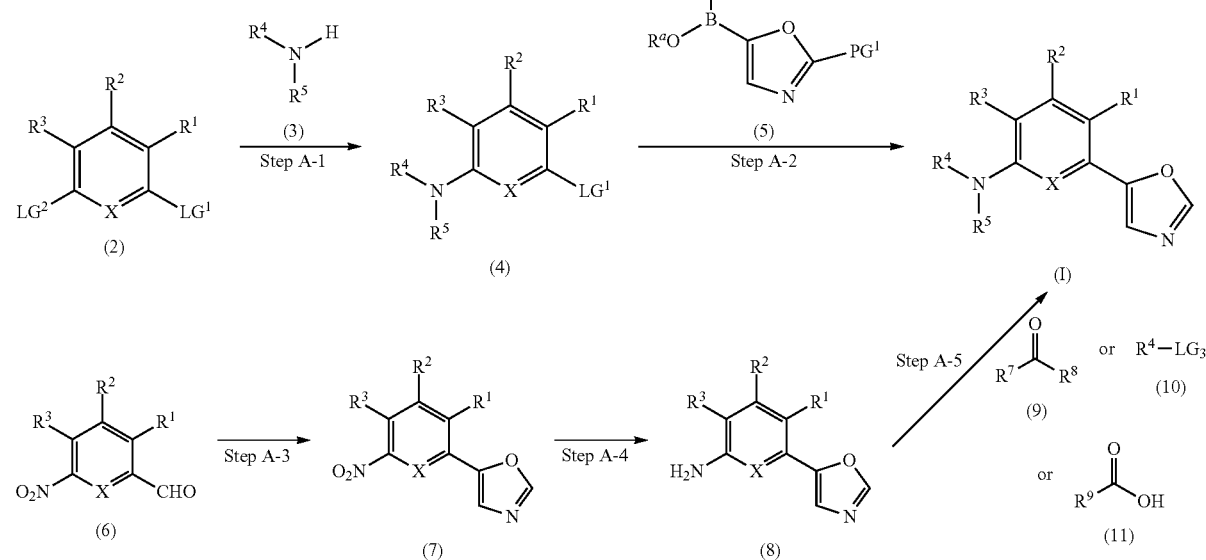

Compound (I) of the present invention can be produced by a sequence of steps from Step A-1 to Step A-2, or a sequence of steps from Step A-3 to Step A-5.

(Step A-1)

Compound (4) can be produced by condensing compound (2) with compound (3). The reaction is carried out in the presence of an acid catalyst, a base or a metal catalyst, if necessary. Examples of the acid catalyst include organic acids and the like. The acid catalyst is used in an amount of about 0.05 to 2 mol per 1 mol of compound (2). Examples of the base include basic salts, organic bases, alkali metal hydrides, organic lithium reagents and the like. The base is used in an amount of about 1 to 20 mol per 1 mol of compound (2). Preferable examples of the metal catalyst include palladium compounds [e.g., palladium(II) acetate, tetrakis(triphenylphosphine)palladium(0), dichlorobis(triphenylphosphine)palladium(II), tris(dibenzylideneacetone)dipalladium(0), [1,1-bis(diphenylphosphino)ferrocene]dichloropalladium(II) and the like] and copper compounds [e.g., copper(I) iodide, copper(I) bromide and the like]. The metal catalyst is used in an amount of about 0.000001 to 10 mol per 1 mol of compound (2). The metal catalyst can be used together with a phosphine ligand [e.g., triphenylphosphine, 4,5-bis(diphenylphosphino)-9,9-dimethylxanthene, tri-tert-butylphosphine and the like] or an amine ligand [e.g., 2-methylquinolin-8-ol, 1,10-phenanthroline, 1,2-diaminocyclohexane, N,N'-dimethyl-1,2-ethanediamine and the like]. When the phosphine ligand or amine ligand is used, it is used in an amount of about 0.01 to 5 mol per 1 mol of compound (2). Compound (3) is used in an amount of about 0.8 to 20 mol per 1 mol of compound (2). When the metal catalyst unstable to oxygen is used in this reaction, for example, the reaction is preferably carried out under an inert gas such as argon gas, nitrogen gas and the like. This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-200 hr. The reaction temperature is preferably 0 to 200° C. In addition, microwave may be irradiated to promote the reaction. Compound (2) and (3) may be a commercially available product, or can also be produced according to a method known per se or a method analogous thereto.

(Step A-2)

Compound (I) of the present invention can be produced by condensing compound (4) with compound (5), and then removing the protecting group represented by PG', if necessary. The reaction is carried out in the presence of a base or a metal catalyst, if necessary. Examples of the base include basic salts, organic bases, alkali metal hydrides, organic lithium reagents and the like. The base is used in an amount of about 1 to 20 mol per 1 mol of compound (4). Preferable examples of the metal catalyst include palladium compounds [e.g., palladium(II) acetate, tetrakis(triphenylphosphine)palladium(0), dichlorobis(triphenylphosphine)palladium(II), tris(dibenzylideneacetone)dipalladium(0), [1,1-bis(diphenylphosphino)ferrocene]dichloropalladium (II) and the like] and copper compounds [e.g., copper(I) iodide, copper(I) bromide and the like]. The metal catalyst is used in an amount of about 0.000001 to 10 mol per 1 mol of compound (4). The metal catalyst can be used together with a phosphine ligand [e.g., triphenylphosphine, 4,5-bis(diphenylphosphino)-9,9-dimethylxanthene, tri-tert-butylphosphine and the like] or an amine ligand [e.g., 2-methylquinolin-8-ol, 1,10-phenanthroline, 1,2-diaminocyclohexane, N,N'-dimethyl-1,2-ethanediamine and the like]. When the phosphine ligand or amine ligand is used, it is used in an amount of about 0.01 to 5 mol per 1 mol of compound (4). Compound (5) is used in an amount of about 0.8 to 10 mol per 1 mol of compound (4). When the metal catalyst unstable to oxygen is used in this reaction, for example, the reaction is preferably carried out under an inert gas such as argon gas, nitrogen gas and the like. This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-200 hr. The reaction temperature is preferably 0 to 200° C. In addition, microwave may be irradiated to promote the reaction. Compound (5) may be a commercially available product, or can also be produced according to a method known per se or a method analogous thereto.

(Step A-3)

Compound (7) can be produced by reacting compound (6) with p-toluenesulfonylmethyl isocyanide. The reaction is carried out in the presence of a base. Examples of the base include basic salts, organic bases, alkali metal hydrides, organic lithium reagents and the like. The base is used in an amount of about 1 to 20 mol per 1 mol of compound (6). This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-200 hr. The reaction temperature is preferably 0 to 200° C. In addition, microwave may be irradiated to promote the reaction. Compound (6) may be a commercially available product, or can also be produced according to a method known per se or a method analogous thereto.

(Step A-4)

Compound (8) can be produced by subjecting compound (7) to reduction. Examples of the reduction method include a method employing a catalytic hydrogen reduction using a transition metal catalyst such as palladium, platinum and the like, a method using a metal hydride reagent such as lithium aluminium hydride and the like, a method using a metal such as iron, tin and the like in an acidic solution, and the like. This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-200 hr. The reaction temperature is preferably 0 to 200° C. In addition, microwave may be irradiated to promote the reaction.

(Step A-5)

Compound (I) of the present invention wherein $R^4$ is —CH($R^7$)($R^8$) and $R^5$ is a hydrogen atom can be produced by subjecting compound (8) to a reductive amination reaction with compound (9). Compound (I) of the present invention wherein $R^4$ is a substituent and $R^5$ is a hydrogen atom or the same substituent as $R^4$ can be produced by condensing compound (8) with compound (10). Compound (I) of the present invention wherein $R^4$ is —C(O)$R^9$ and $R^5$ is a hydrogen atom can be produced by condensing compound (8) with compound (11).

When compound (8) is condensed with compound (9), the reaction is carried out in the presence of a reducing agent. Compound (9) is used in an amount of about 1 mol to large excess, preferably about 1 to 10 mol, per 1 mol of compound (8). Examples of the reducing agent include metal hydrogen complex compounds such as sodium borohydride, sodium cyanoborohydride, lithium aluminium hydride and the like, diborane and the like. The reducing agent is used in an amount of about 0.3 mol to large excess, preferably about 1 to 10 mol, per 1 mol of compound (8). Alternatively, instead of use of the reducing agent, the reaction can also be carried out by employing a catalytic reduction in the presence of a catalyst such as palladium, Raney nickel and the like, an electrolytic reduction using lead or platinum as a cathode, and the like. An acid (e.g., mineral acid such as hydrochloric acid, phosphoric acid, sulfuric acid and the like, organic acid such as toluenesulfonic acid, methanesulfonic acid, acetic acid and the like) may be added to the reaction system. The acid is used in an amount of about 0.1 to 2 mol per 1 mol of compound (8). The solvent is not particularly limited as long as the reaction proceeds. Preferable examples thereof include, alcohols, carboxylic acids, ethers, aromatic hydrocarbons, saturated hydrocarbons, amides, halogenated hydrocarbons, nitriles, esters, sulfoxides, water, mixed solvent thereof and the like. The reaction time is generally about 0.5-about 72 hr, preferably about 1-about 24 hr. The reaction temperature is generally about −30° C.-about 200° C., preferably about 0° C.-about 100° C.

When compound (8) is condensed with compound (10), the reaction is carried out in the presence of a base. Examples of the base include potassium carbonate, sodium carbonate, sodium hydride, potassium hydride and the like. The base is used in an amount of about 1 to 20 mol per 1 mol of compound (8). Compound (10) is used in an amount of about 1 to 20 mol per 1 mol of compound (8). This reaction is advantageously carried out in a solvent inert to the reaction. The solvent is not particularly limited as long as the reaction proceeds. Preferable examples thereof include, alcohols, ethers, aromatic hydrocarbons, saturated hydrocarbons, amides, halogenated hydrocarbons, nitriles, esters, sulfoxides, water, mixed solvent thereof and the like. While the reaction time varies depending on the kind of the reagent and solvent to be used, it is generally 1 min-100 hr. The reaction temperature is preferably 0 to 100° C. In addition, microwave may be irradiated to promote the reaction.

Compound (I) of the present invention wherein $R^4$ is —C(O)$R^9$ and $R^5$ is a hydrogen atom can be produced by condensing compound (8) with carboxylic acid (11) or a reactive derivative thereof. Examples of the reactive derivative include acid halides such as acid chloride, acid bromide and the like; acid amides with pyrazole, imidazole, benzotriazole and the like; mixed anhydrides with acetic acid, propionic acid, butyric acid and the like; acid azides; activated esters such as diethoxyphosphorate ester, diphenoxyphosphorate ester, p-nitrophenyl ester, 2,4-dinitrophenyl ester, an ester with 1-hydroxybenzotriazole, and the like; activated thio esters such as 2-pyridylthio ester, 2-benzothiazolylthio ester and the like, and the like. Alternatively, instead of use of the reactive derivative, compound (8) may be directly reacted with carboxylic acid (11) in the presence of a suitable condensing agent. Examples of the condensing agent include N,N'-di-substituted carbodiimides such as N,N'-dicyclohexylcarbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxyacethylenes and the like; 2-halogeno pyridinium salts such as 2-chloromethylpyridinium iodide, 2-fluoro-1-methylpyridinium iodide and the like; phosphorylcyanides such as diethylphosphorylcyanide and the like; 2-(7-azabenzotriazol-1-yl)-1,1,3,3-tetramethyluronium hexafluorophosphate (HATU), 0-(7-azabenzotriazol-1-yl)-N,N,N',N'-tetramethyluronium tetrafluoroborate (TATU) and the like. The reaction is considered to proceed via a reactive derivative of carboxylic acid (11) by using a condensing agent. Carboxylic acid (11) or a reactive derivative thereof is generally used in an amount of about 0.8 to 5 mol per 1 mol of compound (8). This reaction is advantageously carried out in a solvent inert to the reaction. The solvent is not particularly limited as long as the reaction proceeds. Preferable examples thereof include, ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, basic salts, organic bases and the like can also be used to promote the reaction. While the reaction time varies depending on the kind of the reagent and solvent to be used, it is generally 1 min-72 hr. The reaction temperature is preferably 0 to 100° C. Compound (8) can also be produced according to the method described in the above-mentioned (Step A-4), or a method known per se or method analogous thereto, or may be a commercially available product. Compound (9), (10) and (11) may be a commercially available product, or can also be produced according to a method known per se or a method analogous thereto.

Alternatively, compound (I) of the present invention can also be produced by subjecting compound (8) to Step-A-5, and then subjecting the resulting compound to Step A-5. For example, compound (I) of the present invention can be produced by condensing compound (8) with compound (11), and then condensing the resulting compound with compound (10).

Of compound (4), compound (4a) and a compound represented by (4b) can be produced according to following Production Method B.

[Production Method B]

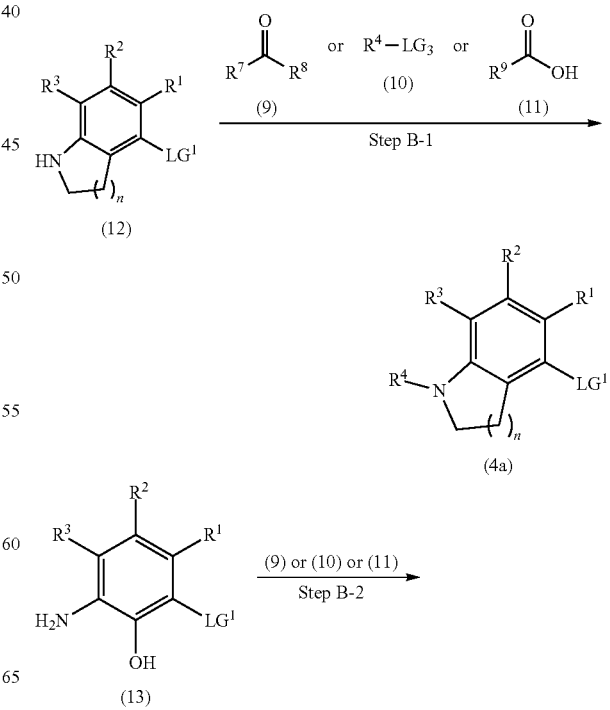

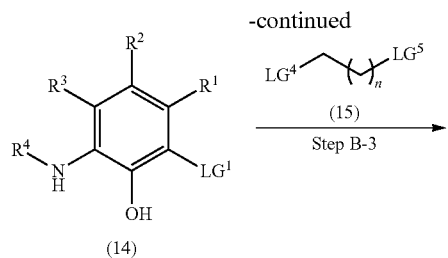

(14)

$n = 1$ or $2$

Compound (4a) can be produced according to Step B-1, and compound (4b) can be produced according to a sequence of steps from Step B-2 to Step B-3.

(Step B-1)

Compound (4a) can be produced by condensing compound (12) with compound (10). Compound (4a) wherein $R^4$ is $-CH(R^7)(R^8)$ can also be produced by subjecting compound (12) to a reductive amination reaction with compound (9), and compound (4a) wherein $R^4$ is $-C(O)R^9$ can also be produced by condensing compound (12) with compound (11). The reaction can be carried out in the same manner as in the method of Step A-5. Compound (9), (10), (11) and (12) may be a commercially available product, or can also be produced according to a method known per se or a method analogous thereto.

(Step B-2)

Compound (14) can be produced by condensing compound (13) with compound (10). Compound (14) wherein $R^4$ is $-CH(R^7)(R^8)$ can also be produced by subjecting compound (13) to a reductive amination reaction with compound (9), and compound (14) wherein $R^4$ is $-C(O)R^9$ can also be produced by condensing compound (13) with compound (11). The reaction can be carried out in the same manner as in the method of Step A-5. Compound (9), (10), (11) and (13) may be a commercially available product, or can also be produced according to a method known per se or a method analogous thereto.

(Step B-3)

Compound (4b) can be produced by condensing compound (14) with compound (15). The reaction can be carried out in the same manner as in the condensation of compound (8) with compound (10) in Step A-5. Compound (15) may be a commercially available product, or can also be produced according to a method known per se or a method analogous thereto.

The raw material compound and/or the production intermediate for compound (I) may form a salt. While the salt is not particularly limited as long as the reaction can be performed, examples thereof include those similar to the salts optionally formed by compound (I) and the like, and the like.

As for the configuration isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can be obtained by isomerizing a double bond using heating, an acid catalyst, a transition metal complex, a metal catalyst, a radical catalyst, light irradiation or a strong base catalyst and the like, according to the method described in Shin-Jikken Kagaku Kouza 14 (The Chemical Society of Japan ed.), pages 251 to 253; 4th Edition Jikken Kagaku Kouza 19 (The Chemical Society of Japan ed.), pages 273 to 274 or a method analogous thereto.

Compound (I) contains a stereoisomer depending to the kind of a substituent, and each stereoisomer and a mixture thereof are encompassed in the present invention.

When desired, compound (I) can be synthesized by performing deprotection reaction, acylation reaction, alkylation reaction, hydrogenation reaction, oxidation reaction, reduction reaction, reaction of carbon chain extension, substituent exchange reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is recemic, d-form and l-form can be isolated according to a conventional optical resolution.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include (1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation or acetylation, cyclopropylcarbonylation, and the like);

(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);

(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

When compound (I) has isomers such as optical isomer, stereoisomer, positional isomer, rotamer and the like, such isomers and a mixture thereof are also encompassed in compound (I). For example, when compound (I) has optical isomers, an optical isomer resolved from this compound is also encompassed in compound (I). These isomers can be obtained as a single product according to synthesis methods or separation methods known per se (e.g., concentration, solvent extraction, column chromatography, recrystallization, etc.).

Compound (I) may be a crystal, and a single crystal form and a mixture of crystal forms are both encompassed in compound (I). The crystal can be produced by crystallizing according to a crystallization method known per se.

Compound (I) may be a hydrate, a non-hydrate, a solvate or a non-solvate.

Compound (I) may be labeled with an isotope (e.g., $^3$H, $^{11}$C, $^{14}$C, $^{18}$F, $^{35}$S, $^{125}$I etc.) and the like.

Compound (I) also encompasses a deuterium conversion form wherein $^1$H is converted to $^2$H(D).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET (Positron Emission Tomography) tracer.

The compound of the present invention has low toxicity, and can be used as it is or in the form of a pharmaceutical composition by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous water-soluble food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the above-mentioned water-soluble food tar color) and natural dyes (e.g., β-carotene, chlorophyll, ferric oxide red).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior CH24H inhibitory action and can suppress nerve cell death, Aβ increase, intracerebral inflammation and the like.

Accordingly, the compound of the present invention is useful for the prophylaxis, improvement of symptoms, suppression of progression or treatment of diseases involving enhanced function of CH24H, for example, neurodegenerative disease.

In the present specification, the "neurodegenerative disease" means a disease associated with denaturation of neural tissues.

Specific examples of the neurodegenerative disease include Alzheimer's disease, mild cognitive disorder, Huntington's disease, Parkinson's disease, multiple sclerosis, amyotrophic lateral sclerosis, disorder or complication associated with brain injury (e.g., traumatic brain injury), post-concussional syndrome, shaken baby syndrome, cerebral infarction, glaucoma, neurodegenerative neurodegeneration deafness, frontotemporal dementia, spinal cord injury, dementia with Lewy bodies and the like.

In addition, the compound of the present invention is useful for the prophylaxis, improvement of symptoms, suppression of progression or treatment of diseases involving enhanced function of CH24H, for example, epilepsy, schizophrenia, convulsion, migraine, hepatic encephalopathy, age-related macular degeneration, pain (e.g., neuropathic pain, inflammatory pain), obsessive compulsive disorder, anxiety disorder, posttraumatic stress disorder, substance use disorder, schizophrenia, opsoclonus myoclonus syndrome, phantom limb pain, autism, opioid dependence, systemic lupus erythematosus and the like.

In addition, the compound of the present invention is useful for the prophylaxis, improvement of symptoms, suppression of progression or treatment of diseases involving CH24H-related inflammation, for example, AIDS-related dementia syndrome, major depression, radiation-induced somnolence syndrome, Down syndrome, and the like.

In addition, all compounds having a CH24H inhibitory action, which are described in the specifications of WO 2013/054822 filed on Oct. 3, 2012, PCT/JP2013/078008 filed on Oct. 15, 2013, and PCT/JP2013/083140 filed on Dec. 10, 2013, are also useful for the prophylaxis, improvement of symptoms, suppression of progression or treatment of the above-mentioned neurodegenerative disease, diseases involving enhanced function of CH24H, diseases involving CH24H-related inflammation, and the like.

The dose of the compound of the present invention varies depending on the administration subject, route of administration, target disease, symptoms, etc. For example, when it is administered orally to an adult patient (body weight 60 kg), its dose is about 0.01 to 100 mg/kg body weight per dose, preferably 0.05 to 30 mg/kg body weight per dose, more preferably 0.1 to 10 mg/kg body weight per dose and this amount is desirably administered in 1 to 3 portions daily.

When the compound of the present invention is applied to each of the above-mentioned diseases, it can be used in an appropriate combination with a medicament or a treatment method generally employed for the disease.

Examples of the medicament (hereinafter to be abbreviated as "concomitant drug") to be used in combination with the compound of the present invention include acetylcholine esterase inhibitors (e.g., donepezil, rivastigmine, galanthamine, zanapezil etc.), antidementia agents (e.g., memantine), inhibitors of β amyloid protein production, secretion, accumulation, coagulation and/or deposition, β secretase inhibitors (e.g., 6-(4-biphenyl)methoxy-2-[2-(N,N-dimethylamino)ethyl]tetralin, 6-(4-biphenyl)methoxy-2-(N,N-dimethylamino)methyltetralin, 6-(4-biphenyl)methoxy-2-(N,N-dipropylamino)methyltetralin, 2-(N,N-dimethylamino) methyl-6-(4'-methoxybiphenyl-4-yl)methoxytetralin, 6-(4-biphenyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid protein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline), other therapeutic drug for Parkinson's disease [(e.g., dopamine receptor agonists (e.g., L-DOPA, bromocriptine, pergolide, talipexole, pramipexole, cabergoline, amantadine), a monoamine oxidase (MAO) inhibitors (e.g., deprenyl, Selgiline (selegiline), remacemide, riluzole), anticholinergic agents (e.g., trihexyphenidyl, biperiden), COMT inhibitors (e.g., entacapone)], therapeutic drug for amyotropic lateral sclerosis (e.g., riluzole etc., neurotrophic factor), therapeutic drug for abnormal behavior wandering and the like due to the progress of dementia (e.g., sedative drug, antianxiety drug), apoptosis inhibitors (e.g., CPI-1189, IDN-6556, CEP-1347), neuronal differentiation or regeneration promoters (e.g., leteprinim, xaliproden (SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates thereof), antidepressants (e.g., desipramine, amitriptyline, imipramine, tramadol), antiepilepsy drug (e.g., lamotrigine), antianxiety drugs (e.g., benzodiazepine), non-steroidal anti-inflammatory drugs (e.g., meloxicam, tenoxicam, indomethacin, ibuprofen, celecoxib, rofecoxib, aspirin), disease-modifying anti-rheumatic drugs (DMARDs), anti-cytokine drugs (e.g., TNF inhibitor MAP kinase inhibitor), steroidal drugs (e.g., dexamethasone, hexestrol, cortisone acetate), therapeutic agents for incontinence or frequent urination (e.g., flavoxate hydrochloride, oxybutynin hydrochloride, propiverine hydrochloride), phosphodiesterase inhibitors (e.g., sildenafil (citrate)), dopamine agonists (e.g., apomorphine etc.), antiarrhythmics (e.g., mexiletine), sex hormones or derivatives thereof (e.g., progesterone, estradiol, estradiol benzoate), therapeutic agents for osteoporosis (e.g., alfacalcidol, calcitriol, elcatonin, calcitonin salmon, estriol, ipriflavone, disodium pamidronate, sodium alendronate hydrate, disodium incadronate), parathyroid hormone (PTH), calcium receptor antagonists, therapeutic drugs for insomnia (e.g., benzodiazepine medicament, non-benzodiazepine medicament, melatonin agonist), therapeutic drugs for schizophrenia (e.g., typical antipsychotic agents such as haloperidol and the like; atypical antipsychotic agents such as clozapine, olanzapine, risperidone, aripiprazole and the like; medicament acted on metabotropic glutamate receptor or ionic channel-conjugated glutamate receptor;phosphodiesterase inhibitor) and the like.

In addition, a combined use with a transplantation method of neural stem cell or neural precursor cell prepared from embryonic stem cell or nervous tissue, or fetal neural tissue, and a combined use with a pharmaceutical agent such as an immunosuppressant after the transplantation and the like.

Furthermore, the compound of the present invention may be used in combination with the following concomitant drugs.

(1) Therapeutic Agent for Diabetes

For example, insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose-dependent insulin secretagogue (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof)], dipeptidyl peptidase IV inhibitor (e.g., Alogliptin, Vildagliptin, Sitagliptin, Saxagliptin, T-6666, TS-021), 13 agonist (e.g., AJ-9677), GPR40 agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

(2) Therapeutic Agents for Diabetic Complications

For example, aldose reductase inhibitors (e.g., tolrestat, epalrestat, zenarestat, zopolrestat, minalrestat, fidarestat, CT-112), neurotrophic factor and an increasing agent thereof (e.g., NGF, NT-3, BDNF, neurotrophic factors and increasing drugs described in WO01/14372 (e.g., 4-(4-chlorophenyl)-2-(2-methyl-1-imidazolyl)-5-[3-(2-methylphenoxy) propyl]oxazole)), nerve regeneration promoting agent (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1 (ASK-1) inhibitor and the like can be mentioned.

(3) Therapeutic Agent for Hyperlipidemia

For example, statin compound (e.g., pravastatin, simvastatin, lovastatin, atorvastatin, fluvastatin, rosuvastatin, pitavastatin, or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol) and the like.

(4) Antihypertensive Agent

For example, angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, Azilsartan, Azilsartan medoxomil), calcium antagonist (e.g., manidipine, nifedipine, amlodipine, efonidipine, nicardipine), potassium channel opener (e.g., levcromakalim, L-27152, AL 0671, NIP-121), clonidine and the like.

(5) Antiobesity Agent

For example, central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), anorexigenic agent (e.g., P-57) and the like.

(6) Diuretic

For example, xanthine derivative (e.g., theobromine sodium salicylate, theobromine calcium salicylate), thiazide preparation (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone preparation (e.g., spironolactone, triamterene), carbonic anhydrase inhibitors (e.g., acetazolamide), chlorobenzenesulfonamide agent (e.g., chlortalidone, mefruside, indapamide), azosemide, isosorbide, ethacrynic acid, piretanide, bumetanide, furosemide and the like.

(7) Chemotherapeutic Agent

For example, alkylating agents (e.g., cyclophosphamide, Ifosfamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon and Neo-Furtulon, which are 5-fluorouracil derivatives, and the like are preferable.

(8) Immunotherapeutic Agent

For example, microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor erythropoietin) and the like, with preference given to interleukins such as IL-1, IL-2, IL-12 and the like.

(9) Antithrombotic Agent

For example, heparin (e.g., heparin sodium, heparin calcium, dalteparin sodium), warfarin (e.g., warfarin potassium), anti-thrombin drug (e.g., argatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like.

(10) Cachexia Improving Medicament

For example, cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentaenoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like.

Two or more kinds of the above-mentioned concomitant drugs may be used in combination at an appropriate ratio.

It is also possible to apply compound of the present invention to each of the above-mentioned diseases in combination with a biologic (e.g., antibody, vaccine preparation etc.), or as a combination therapy in combination with gene therapy method and the like.

Examples of the antibody and vaccine preparation include vaccine preparation to angiotensin II, vaccine preparation to CETP, CETP antibody, TNFα antibody and antibody to other cytokine, amyloid β vaccine preparation, type 1 diabetes vaccine (e.g., DIAPEP-277 manufactured by Peptor Ltd.), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like.

In addition, a combined use with a biological preparation involved in a growth factor such as GH, IGF and the like is possible.

Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NFκB decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid), a treatment method using a gene relating to an enzyme or protein involved in angiogenesis therapy targeting obstruction of peripheral vessel and the like (e.g., growth factors such as HGF, VEGF etc.), a treatment method using a gene relating to a protein involved in saccharometabolism or insulin resistance, an antisense to cytokine such as TNF and the like, and the like.

In addition, it is possible to use in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell) or an artificial organ utilizing tissue engineering (e.g., artificial blood vessel and cardiac muscle cell sheet).

The time of administration of the compound of the present invention and that of the concomitant drug are not limited, and they may be administered simultaneously or in a staggered manner to the administration subject. Furthermore, the compound of the present invention and the concomitant drug may be administered as two kinds of preparations containing each active ingredient, or a single preparation containing both active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of the compound of the present invention.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The abbreviations used in the specification mean the following.
THF: tetrahydrofuran
DME: 1,2-dimethoxyethane
DMF: N,N-dimethylformamide
DMA: N,N-dimethylacetamide
DMSO: dimethyl sulfoxide
ESI: Electron Spray Ionization
APCI: atmospheric pressure chemical ionization
M: mol concentration
IPE: diisopropyl ether
WSC: 1-[3-(dimethylamino)propyl]-3-ethylcarbodiimide
HOBt: 1-hydroxybenzotriazole
HPLC: high-performance liquid chromatography
$Pd_2(dba)_3$: tris(dibenzylideneacetone)dipalladium(0)
$Pd(PPh_3)_4$: tetrakis(triphenylphosphine)palladium(0)
Xantphos: 4,5-bis(diphenylphosphino)-9,9-dimethylxanthene
IPA: isopropyl alcohol $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As API (Atmospheric Pressure Ionization), ESI (Electro Spray Ionization) method, or APCI (Atmospheric Pressure Chemical Ionization) method was used. The data indicates those found. Generally, a molecular ion peak ([M]+, [M+H]$^+$, [M−H]$^-$, etc.) is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of $H_2O$ may be observed as a fragment ion. In the case of a salt, a molecular ion peak or fragment ion peak of free form is generally observed.

The elemental analysis value (Anal.) shows Calculated value (Calcd) and Found value (Found).

Example 1

3-chloro-N-(3-(1,3-oxazol-5-yl)-5-(trifluoromethyl)phenyl)benzamide

A) N-methoxy-N-methyl-3-nitro-5-(trifluoromethyl)benzamide

To a solution of 3-nitro-5-(trifluoromethyl)benzoic acid (10 g) in DMF (100 mL) were added N,O-dimethylhydroxylamine hydrochloride (4.56 g), HOBt (6.90 g), WSC hydrochloride (9.78 g) and triethylamine (6.50 mL) at 0° C. The mixture was stirred overnight at room temperature, water was added thereto, and the mixture was extracted with ethyl acetate. The organic layer was washed with water, saturated aqueous sodium hydrogencarbonate solution and saturated brine, and dried over anhydrous magnesium sulfate, and the solvent was evaporated under reduced pressure. The residue was purified by silica gel column chromatography (ethyl acetate/hexane) to give the title compound (11.73 g).
$^1$H NMR (300 MHz, DMSO-$d_6$) δ 3.34-3.40 (3H, m), 3.58 (3H, d, J=4.2 Hz), 8.40 (1H, d, J=4.2 Hz), 8.66 (2H, s).

B) 3-nitro-5-(trifluoromethyl)benzaldehyde

To a solution of N-methoxy-N-methyl-3-nitro-5-(trifluoromethyl)benzamide (11.73 g) in THF (300 mL) was added diisobutylaluminum hydride toluene solution (36.5 mL, 54.82 mmol) at 0° C. The reaction mixture was stirred at 0° C. for 2.5 hr, 1M hydrochloric acid was added thereto, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (7.68 g).
$^1$H NMR (300 MHz, DMSO-$d_6$) δ 8.69 (1H, s), 8.78 (1H, s), 8.92 (1H, s), 10.20 (1H, s).

C) 5-(3-nitro-5-(trifluoromethyl)phenyl)-1,3-oxazole

To a solution of 3-nitro-5-(trifluoromethyl)benzaldehyde (1.77 g) and p-toluenesulfonylmethyl isocyanide (1.735 g) in methanol (50 mL) was added potassium carbonate (2.233 g) at room temperature, and the mixture was heated with reflux for 2 hr. The solvent was evaporated under reduced pressure, to the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (1.86 g).
MS (API+): [M+H]$^+$ 258.9

D) 3-(1,3-oxazol-5-yl)-5-(trifluoromethyl)aniline 5-(3-nitro-5-(trifluoromethyl)phenyl)-1,3-oxazole (800 mg) was dissolved in THF (20 mL) and ethanol (10 mL), and 10% palladium on carbon (80 mg) was added thereto. The mixture was stirred at room temperature for 16 hr under hydrogen atmosphere. The insoluble substance was removed by filtration, and the filtrate was concentrated under reduced pressure. The residue was purified by silica gel column chromatography (ethyl acetate/hexane) to give the title compound (675 mg).
$^1$H NMR (300 MHz, CDCl$_3$) δ 3.98 (2H, brs), 6.86 (1H, s), 7.09 (1H, s), 7.24-7.29 (1H, m), 7.38 (1H, s), 7.92 (1H, s).

E) 3-chloro-N-(3-(1,3-oxazol-5-yl)-5-(trifluoromethyl)phenyl)benzamide

To a solution of 3-(1,3-oxazol-5-yl)-5-(trifluoromethyl)aniline (300 mg) and 3-chlorobenzoyl chloride (202 μL) in THF (15 mL) was added triethylamine (275 μL) at room temperature. The mixture was stirred at room temperature for 2 hr, to the reaction mixture was added water, and the mixture was extracted with ethyl acetate. The organic layer was washed with water and saturated brine, and dried over anhydrous magnesium sulfate, and the solvent was evaporated under reduced pressure. The residue was crystallized from ethyl acetate/hexane to give the title compound (409 mg).
$^1$H NMR (300 MHz, DMSO-d$_6$) δ 7.58-7.65 (1H, m), 7.69-7.74 (1H, m), 7.87 (1H, dd, J=1.7, 0.9 Hz), 7.92 (1H, s), 7.96 (1H, dq, J=7.5, 0.9 Hz), 8.06-8.09 (1H, m), 8.20-8.24 (1H, m), 8.43-8.48 (1H, m), 8.56 (1H, s), 10.76 (1H, brs).

Example 4

3-chloro-N-(3-isopropyl-5-(1,3-oxazol-5-yl)phenyl)benzenesulfonamide

A) 5-(3-bromo-5-nitrophenyl)-1,3-oxazole

To a solution of 3-bromo-5-nitrobenzaldehyde (1.90 g) and p-toluenesulfonylmethyl isocyanide (1.774 g) in methanol (30 mL) was added potassium carbonate (2.283 g) at room temperature, and the mixture was stirred at 60° C. for 2 hr. The solvent was evaporated under reduced pressure, to the reaction mixture was added water, and the mixture was extracted with ethyl acetate. The organic layer was washed with water and saturated brine, and dried over anhydrous magnesium sulfate, and the solvent was evaporated under reduced pressure. The residue was crystallized from ethyl acetate/hexane to give the title compound (2.200 g).
MS (API+): [M+H]$^+$ 270.0

3) 5-(3-nitro-5-(prop-1-en-2-yl)phenyl)-1,3-oxazole

To a solution of 5-(3-bromo-5-nitrophenyl)-1,3-oxazole (673 mg), 4,4,5,5-tetramethyl-2-(prop-1-en-2-yl)-1,3,2-dioxaborolane (564 μL) and bis(triphenylphosphine)palladium(II) chloride (176 mg) in DME (15 mL)-water (5 mL) was added potassium carbonate (691 mg) at room temperature. The reaction mixture was stirred at 90° C. for 3.5 hr under nitrogen atmosphere, and extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (529 mg).
$^1$H NMR (300 MHz, CDCl$_3$) δ 2.24 (3H, s), 5.33 (1H, brs), 5.56 (1H, s), 7.53 (1H, s), 7.96-8.05 (2H, m), 8.26 (1H, t, J=1.9 Hz), 8.39 (1H, t, J=1.7 Hz).

C) 3-isopropyl-5-(1,3-oxazol-5-yl)aniline 5-(3-Nitro-5-(prop-1-en-2-yl)phenyl)-1,3-oxazole (525 mg) was dissolved in ethanol (25 mL), and 10% palladium on carbon (50 mg) was added thereto. The mixture was stirred at room temperature for 24 hr under hydrogen atmosphere. The insoluble substance was removed by filtration, and the filtrate was concentrated under reduced pressure. The residue was purified by silica gel column chromatography (ethyl acetate/hexane) to give the title compound (418 mg).
MS (API+): [M+H]$^+$ 203.1

D) 3-chloro-N-(3-isopropyl-5-(1,3-oxazol-5-yl)phenyl)benzenesulfonamide

A solution of 3-isopropyl-5-(1,3-oxazol-5-yl)aniline (218 mg) and 3-chlorobenzene-1-sulfonyl chloride (159 μL) in pyridine (10 mL) was stirred at room temperature for 16 hr. The reaction mixture was concentrated under reduced pressure, 1M hydrochloric acid was added to the residue, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane), and crystallized from ethyl acetate/hexane to give the title compound (356 mg).
$^1$H NMR (300 MHz, CDCl$_3$ δ 1.21 (6H, d, J=6.8 Hz), 2.79-2.95 (1H, m), 6.75 (1H, s), 6.88 (1H, t, J=1.7 Hz), 7.19-7.44 (4H, m), 7.48-7.56 (1H, m), 7.62-7.69 (1H, m), 7.79 (1H, t, J=1.7 Hz), 7.91 (1H, s).

Example 9

3-chloro-N-(7-(1,3-oxazol-5-yl)-2,3-dihydro-1-benzofuran-5-yl)benzamide

A) 5-(5-bromo-2,3-dihydrobenzofuran-7-yl)-1,3-oxazole

To a solution of 5-bromo-2,3-dihydrobenzofuran-7-carbaldehyde (580 mg) and p-toluenesulfonylmethyl isocyanide (549 mg) in methanol (20 mL) was added potassium carbonate (706 mg) at room temperature, and the mixture was heated with reflux for 2 hr. The solvent was evaporated under reduced pressure, to the reaction mixture was added water, and the mixture was extracted with ethyl acetate. The organic layer was washed with water and saturated brine, and dried over anhydrous magnesium sulfate, and the solvent was evaporated under reduced pressure. The residue was crystallized from ethyl acetate/hexane to give the title compound (616 mg).
MS (API+): [M+H]$^+$ 267.9

B) N-(diphenylmethylene)-7-(1,3-oxazol-5-yl)-2,3-dihydrobenzofuran-5-amine

A mixture of 5-(5-bromo-2,3-dihydrobenzofuran-7-yl)-1,3-oxazole (605 mg), diphenylmethanimine (459 μL), Pd$_2$(dba)$_3$ (104 mg), 2,2'-bis(diphenylphosphino)-1,1'-binaphthyl (142 mg), sodium tert-butoxide (328 mg) and toluene (25 mL) was stirred at 85° C. for 16 hr under argon gas atmosphere. To the reaction mixture was added water, the mixture was filtered through Celite, and the filtrate was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (392 mg).

$^1$H NMR (300 MHz, CDCl$_3$) δ 3.11 (2H, t, J=8.7 Hz), 4.65 (2H, t, J=8.9 Hz), 6.53-6.56 (1H, m), 6.93-6.96 (1H, m), 7.12-7.20 (2H, m), 7.27-7.32 (3H, m), 7.36-7.51 (4H, m), 7.71-7.77 (2H, m), 7.82 (1H, s).

C) 7-(1,3-oxazol-5-yl)-2,3-dihydrobenzofuran-5-amine

A mixture of N-(diphenylmethylene)-7-(1,3-oxazol-5-yl)-2,3-dihydrobenzofuran-5-amine (390 mg), hydroxylamine hydrochloride (111 mg), sodium acetate (175 mg) and methanol (20 mL) was stirred at room temperature for 45 min. The reaction mixture was concentrated under reduced pressure, water was added to the residue, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (167 mg).
MS (API+): [M+H]$^+$ 203.0

D) 3-chloro-N-(7-(1,3-oxazol-5-yl)-2,3-dihydro-1-benzofuran-5-yl)benzamide

To a solution of 7-(1,3-oxazol-5-yl)-2,3-dihydrobenzofuran-5-amine (80 mg) and 3-chlorobenzoyl chloride (55.7 µL) in THF (10 mL) was added triethylamine (66.2 µL) at room temperature. The mixture was stirred at room temperature for 30 min, to the reaction mixture was added water, and the mixture was extracted with ethyl acetate. The organic layer was washed with water and saturated brine, and dried over anhydrous magnesium sulfate, and the solvent was evaporated under reduced pressure. The residue was crystallized from ethyl acetate/hexane to give the title compound (130 mg).
$^1$H NMR (300 MHz, DMSO-d$_6$) δ 3.24-3.34 (2H, m), 4.73 (2H, t, J=8.7 Hz), 7.44 (1H, s), 7.53-7.61 (1H, m), 7.63-7.72 (2H, m), 7.89-7.96 (2H, m), 8.02 (1H, t, J=1.9 Hz), 8.47 (1H, s), 10.31 (1H, brs).

Example 17

N-(3-(1,3-oxazol-5-yl)-5-(trifluoromethyl)phenyl)cyclopropanecarboxamide

To a solution of 3-(1,3-oxazol-5-yl)-5-(trifluoromethyl)aniline (200 mg) and cyclopropanecarbonyl chloride (95 µL) in THF (20 mL) was added triethylamine (159 µL) at room temperature. The mixture was stirred at room temperature for 1 hr, to the reaction mixture was added water, and the mixture was extracted with ethyl acetate. The organic layer was washed with water and saturated brine, and dried over anhydrous magnesium sulfate, and the solvent was evaporated under reduced pressure. The residue was crystallized from ethyl acetate/hexane to give the title compound (246 mg).
$^1$H NMR (300 MHz, CDCl$_3$) δ 0.88-0.96 (2H, m), 1.11-1.18 (2H, m), 1.48-1.57 (1H, m), 7.45 (1H, s), 7.59-7.63 (2H, m), 7.70-7.73 (1H, m), 7.94 (1H, s), 8.13-8.17 (1H, m).

Example 22

N-(3-(1,3-oxazol-5-yl)-5-(trifluoromethyl)phenyl)cyclopentanecarboxamide

To a solution of 3-(1,3-oxazol-5-yl)-5-(trifluoromethyl)aniline (50 mg) in THF (1 mL) were added cyclopentanecarbonyl chloride (40 µL) and pyridine (26 µL) at 0° C. The mixture was stirred at room temperature for 1 hr, to the reaction mixture was added 1M hydrochloric acid, and the mixture was extracted with ethyl acetate. The organic layer was washed with 1M hydrochloric acid and saturated brine, and dried over anhydrous sodium sulfate, and the solvent was evaporated under reduced pressure. The residue was purified by silica gel column chromatography (ethyl acetate/hexane) to give the title compound (13.4 mg).
$^1$H NMR (300 MHz, CDCl$_3$) δ 1.61-2.07 (8H, m), 2.72 (1H, quin, J=7.9 Hz), 7.33 (1H, brs), 7.46 (1H, s), 7.62 (1H, s), 7.72 (1H, s), 7.95 (1H, s), 8.17 (1H, s).

Example 36 cyclopropyl(4-(1,3-oxazol-5-yl)-6-(trifluoromethyl)-2,3-dihydro-1H-indol-1-yl)methanone A) 3-bromo-2-iodo-5-(trifluoromethyl)aniline To a solution of 3-bromo-5-(trifluoromethyl)aniline (15.0 g) in acetic acid (120 mL) was added 1-iodopyrrolidine-2,5-dione (14.76 g) at 0° C. The reaction mixture was stirred at 0° C. for 1 hr, and then overnight at room temperature. To the reaction mixture was added saturated aqueous sodium thiosulfate solution (10 mL), and the mixture was stirred for 10 min. The insoluble substance was removed by filtration, and the filtrate was concentrated under reduced pressure. The residue was added to water, and the mixture was extracted with ethyl acetate. The organic layer was washed with saturated aqueous sodium hydrogencarbonate solution, water and saturated brine, and dried over anhydrous sodium sulfate, and the solvent was evaporated under reduced pressure. The residue was purified by silica gel column chromatography (ethyl acetate/hexane) to give the title compound (20.30 g).
$^1$H NMR (300 MHz, CDCl$_3$) δ 4.58 (2H, brs), 6.84 (1H, d, J=1.3 Hz), 7.23 (1H, d, J=1.3 Hz).

B) 3-bromo-5-(trifluoromethyl)-2-((trimethylsilyl)ethynyl)aniline

To a solution of 3-bromo-2-iodo-5-(trifluoromethyl)aniline (20.3 g) in triethylamine (160 mL) were added ethynyltrimethylsilane (8.62 mL), bis(triphenylphosphine)palladium(II) dichloride (1.947 g), and copper(I) iodide (0.528 g). The reaction mixture was stirred overnight at 80° C. under nitrogen gas atmosphere, the insoluble substance was removed by filtration, and the filtrate was concentrated under reduced pressure. The residue was diluted with ethyl acetate, and the mixture was added to saturated aqueous ammonium chloride solution, and extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (15.46 g).
$^1$H NMR (300 MHz, CDCl$_3$) δ 0.30 (9H, s), 4.56 (2H, brs), 6.84 (1H, s), 7.14 (1H, s).

C) 3-bromo-2-ethynyl-5-(trifluoromethyl)aniline

To a solution of 3-bromo-5-(trifluoromethyl)-2-((trimethylsilyl)ethynyl)aniline (15.4 g) in methanol (230 mL) was added potassium carbonate (6.33 g) at room temperature. The reaction mixture was stirred at room temperature for 1 hr, and the pH was adjusted to 7-8 with saturated aqueous ammonium chloride solution. The insoluble substance was removed by filtration, and the filtrate was concentrated under reduced pressure. The residue was diluted with ethyl acetate, and the mixture was added to saturated aqueous ammonium chloride solution, and extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (10.30 g).

$^1$H NMR (300 MHz, CDCl$_3$) δ 3.78 (1H, s), 4.59 (2H, brs), 6.86 (1H, s), 7.16 (1H, s).

D) 4-bromo-6-(trifluoromethyl)-1H-indole

A solution of 3-bromo-2-ethynyl-5-(trifluoromethyl)aniline (10.3 g) in N-methyl-2-pyrrolidone (30 mL) was added to a mixture of potassium tert-butoxide (10.2 g) and N-methyl-2-pyrrolidone (180 mL) at 0° C. The mixture was stirred overnight at room temperature, diluted with ethyl acetate, washed with saturated aqueous ammonium chloride solution, water and saturated brine, and dried over anhydrous sodium sulfate, and the solvent was evaporated under reduced pressure. The residue was purified by basic silica gel column chromatography (ethyl acetate/hexane) to give the title compound (8.28 g).

$^1$H NMR (300 MHz, CDCl$_3$) δ 6.68 (1H, t, J=2.2 Hz), 7.41 (1H, t, J=2.8 Hz), 7.55 (1H, s), 7.64 (1H, s), 8.55 (1H, brs).

E) 4-bromo-6-(trifluoromethyl)indoline

To a solution of 4-bromo-6-(trifluoromethyl)-1H-indole (4.00 g) in trifluoroacetic acid (30 mL) was added triethylsilane (7.26 mL) at 0° C. The reaction mixture was stirred at room temperature for 3 hr, and concentrated under reduced pressure. The residue was diluted with ethyl acetate, and the mixture was added to saturated aqueous sodium hydrogencarbonate solution, and extracted with ethyl acetate. The organic layer was washed with water and saturated brine, and dried over anhydrous sodium sulfate, and the solvent was evaporated under reduced pressure. The residue was purified by basic silica gel column chromatography (ethyl acetate/hexane) to give the title compound (3.47 g).

$^1$H NMR (300 MHz, CDCl$_3$) δ 3.02-3.13 (2H, m), 3.67 (2H, td, J=8.6, 1.8 Hz), 4.05 (1H, brs), 6.68 (1H, s), 7.05 (1H, s).

F) (4-bromo-6-(trifluoromethyl)indolin-1-yl) (cyclopropyl)methanone

To a solution of 4-bromo-6-(trifluoromethyl)indoline (1.50 g) in THF (30 mL) were added cyclopropanecarbonyl chloride (0.614 mL) and pyridine (0.59 mL) at 0° C. The mixture was stirred at room temperature for 3 hr, the reaction mixture was added to water, and the mixture was extracted with ethyl acetate. The organic layer was washed with 0.1M hydrochloric acid, water and saturated brine, and dried over anhydrous sodium sulfate, and the solvent was evaporated under reduced pressure. The residue was crystallized from IPE to give the title compound (1.47 g).

$^1$H NMR (300 MHz, CDCl$_3$) δ 0.94 (2H, dq, J=7.5, 3.7 Hz), 1.16 (2H, quin, J=3.7 Hz), 1.75 (1H, brs), 3.25 (2H, t, J=8.6 Hz), 4.37 (2H, t, J=8.7 Hz), 7.41 (1H, s), 8.41 (1H, brs).

G) 2-(triisopropylsilyl)-1,3-oxazole

To a solution of 1,3-oxazole (2 g) in THF (90 mL) was added dropwise n-butyllithium hexane solution (1.6M, 19.7 mL) at −78° C. The reaction mixture was stirred at 0° C. for 10 min under nitrogen atmosphere, and triisopropylsilyl triflate (8.5 mL) was added thereto. The reaction mixture was stirred at room temperature for 2 hr, and the solvent was evaporated under reduced pressure. To the residue was added ethyl acetate, and the mixture was washed with water and saturated brine, and the solvent was evaporated under reduced pressure to give the title compound (6.7 g).

MS (APCI+): [M+H]$^+$ 226.3.

H) 5-(4,4,5,5-tetramethyl-1,3,2-dioxaborolan-2-yl)-2-(triisopropylsilyl)-1,3-oxazole To a solution of 2-(triisopropylsilyl)-1,3-oxazole (6.7 g) in THF (200 mL) was added dropwise n-butyllithium hexane solution (1.6M, 22.3 mL) at −78° C. The reaction mixture was stirred at −78° C. for 1 hr under nitrogen atmosphere, triisopropyl borate (8.2 mL) was added thereto, and the mixture was stirred at −78° C. for 2 hr. The mixture was allowed to be warmed to room temperature, and stirred overnight. To the reaction mixture were added a solution of 2,3-dimethylbutane-2,3-diol (3.51 g) in THF (20 mL), and acetic acid (2.3 mL), and the mixture was stirred at room temperature for 2 hr. The solvent was evaporated under reduced pressure, water was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (8.8 g).

$^1$H NMR (300 MHz, CDCl$_3$) δ 1.14 (18H, d, J=7.2 Hz), 1.35 (12H, s), 1.44 (3H, dq, J=14.8, 7.5 Hz), 7.73 (1H, s).

I) cyclopropyl(4-(1,3-oxazol-5-yl)-6-(trifluoromethyl)-2,3-dihydro-1H-indol-1-yl)methanone A mixture of (4-bromo-6-(trifluoromethyl)indolin-1-yl)(cyclopropyl)methanone (700 mg), 5-(4,4,5,5-tetramethyl-1,3,2-dioxaborolan-2-yl)-2-(triisopropylsilyl)-1,3-oxazole (883 mg), potassium carbonate (579 mg), Pd(PPh$_3$)$_4$ (242 mg), DME (7 mL) and water (1.4 mL) was irradiated with microwave at 120° C. for 30 min under nitrogen gas atmosphere. The mixture was allowed to be cooled to room temperature, saturated brine was added thereto, and the mixture was extracted with ethyl acetate/DMF (2/1). The organic layer was washed with saturated brine, and dried over anhydrous sodium sulfate, and the solvent was evaporated under reduced pressure. The residue was DMF/ethyl acetate crystallized from to give the title compound (320 mg).

$^1$H NMR (300 MHz, DMSO-d$_6$) δ 0.87-0.97 (4H, m), 2.01 (1H, dt, J=12.2, 6.3 Hz), 3.46 (2H, t, J=8.5 Hz), 4.46 (2H, t, J=8.6 Hz), 7.66 (1H, s), 7.74 (1H, s), 8.35 (1H, s), 8.57 (1H, s).

Example 53 cyclopropyl(9-(1,3-oxazol-5-yl)-7-(trifluoromethyl)-3,4-dihydro-1,5-benzoxazepin-5(2H)-yl)methanone

A) 2-nitro-4-(trifluoromethyl)phenol

To a solution of 1-chloro-2-nitro-4-(trifluoromethyl)benzene (20 g) in DNS® (100 mL) was added powder sodium hydroxide (8.87 g), and the mixture was stirred overnight at room temperature. The reaction mixture was added to ice water, the pH of the mixture was adjusted to 1 with 6M hydrochloric acid, and the mixture was extracted with ethyl acetate. The organic layer was washed with water and saturated brine, and dried over anhydrous magnesium sulfate, and the solvent was evaporated under reduced pressure. The same procedures were performed using 1-chloro-2-nitro-4-(trifluoromethyl)benzene (1 g), DMSO (5 mL) and sodium hydroxide (0.45 g). The two lots were combined, and the following procedure was performed. The obtained residue was purified by silica gel column chromatography (ethyl acetate/hexane) to give the title compound (17.47 g).

$^1$H NMR (300 MHz, DMSO-$d_6$) δ 7.17-7.52 (1H, m), 7.80-7.98 (1H, m), 8.22 (1H, d, J=2.5 Hz).

B) 2-bromo-6-nitro-4-(trifluoromethyl)phenol

To a mixture of 2-nitro-4-(trifluoromethyl)phenol (4 g), iron(III) chloride (0.313 g) and acetic acid (24 mL) was added dropwise a solution of bromine (1.286 mL) in acetic acid (8 mL) at 0° C. The reaction mixture was stirred at 40° C. for 2 hr, and then at room temperature for 5 hr. The reaction mixture was filtered through Celite, and the filtrate was diluted with ethyl acetate. The mixture was washed with water and saturated brine, and dried over anhydrous magnesium sulfate, and the solvent was evaporated under reduced pressure. The residue was purified by silica gel column chromatography (ethyl acetate/hexane) to give the title compound (5.37 g).

$^1$H NMR (300 MHz, DMSO-$d_6$) δ 8.26 (1H, dd, J=2.3, 0.8 Hz), 8.32 (1H, dd, J=2.3, 0.6 Hz). The 1H of phenolic hydroxyl group was not observed.

C) cyclopropyl(9-(1,3-oxazol-5-yl)-7-(trifluoromethyl)-3,4-dihydro-1,5-benzoxazepin-5(2H)-yl)methanone To a solution of 2-bromo-6-nitro-4-(trifluoromethyl)phenol (1.30 g) in ethanol (10 mL) was added dropwise a solution of sodium hyposulfite (3.17 g) in water (10 mL) at 60° C. After dropwise addition, the reaction mixture was allowed to be cooled to room temperature, the insoluble substance was removed by filtration, and the filtrate was concentrated under reduced pressure. The residue was diluted with ethyl acetate, the mixture was washed with saturated brine, and dried over anhydrous sodium sulfate, and the solvent was evaporated under reduced pressure to give crude 2-amino-6-bromo-4-(trifluoromethyl)phenol.

To a solution of the obtained crude 2-amino-6-bromo-4-(trifluoromethyl)phenol in DMA (30 mL) was added cyclopropanecarbonyl chloride (0.454 mL) at 0° C. The mixture was stirred at 0° C. for 3 hr, the reaction mixture was added to water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give N-(3-bromo-2-hydroxy-5-(trifluoromethyl)phenyl)cyclopropanecarboxamide.

To a solution of the obtained N-(3-bromo-2-hydroxy-5-(trifluoromethyl)phenyl)cyclopropanecarboxamide and 1-bromo-3-chloropropane (0.342 mL) in DMF (31.5 mL) was added potassium carbonate (1.088 g) at room temperature. The reaction mixture was stirred at room temperature for 1 hr, and then at 120° C. overnight, under nitrogen gas atmosphere. The reaction mixture was allowed to be cooled to room temperature, and added to water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) and basic silica gel column chromatography (ethyl acetate/hexane) to give (9-bromo-7-(trifluoromethyl)-3,4-dihydrobenzo[b][1,4]oxazepin-5(2H)-yl)(cyclopropyl)methanone.

A mixture of the obtained (9-bromo-7-(trifluoromethyl)-3,4-dihydrobenzo[b][1,4]oxazepin-5(2H)-yl)(cyclopropyl)methanone, 5-(4,4,5,5-tetramethyl-1,3,2-dioxaborolan-2-yl)-2-(triisopropylsilyl)-1,3-oxazole (643 mg), potassium carbonate (421 mg), Pd(PPh$_3$)$_4$ (176 mg), DME (12 mL) and water (2 mL) was stirred overnight at 90° C. under nitrogen gas atmosphere. The reaction mixture was allowed to be cooled to room temperature, saturated aqueous ammonium chloride solution was added thereto, and the mixture was extracted with ethyl acetate. The organic layer was washed with water and saturated brine, and dried over anhydrous magnesium sulfate, and the solvent was evaporated under reduced pressure. The residue was dissolved in THF (5 mL), 1M hydrochloric acid (5 mL) was added thereto, and the mixture was stirred at room temperature for 1 hr. The reaction solution was added to water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane), and crystallized from ethyl acetate/hexane to give the title compound (58.8 mg).

$^1$H NMR (300 MHz, CDCl$_3$) δ 0.74 (2H, brs), 1.12 (2H, brs), 1.23-1.47 (1H, m), 1.85-2.48 (2H, m), 2.97 (1H, brs), 3.79-4.16 (1H, m), 4.63 (1H, brs), 4.90 (1H, brs), 7.55 (1H, d, J=1.9 Hz), 7.60-7.76 (1H, m), 7.93-8.08 (2H, m).

Example 54 cyclopropyl(8-(1,3-oxazol-5-yl)-6-(trifluoromethyl)-2,3-dihydro-4H-1,4-benzoxazin-4-yl)methanone A) (8-bromo-6-(trifluoromethyl)-2H-benzo[b][1,4]oxazin-4(3H)-yl)(cyclopropyl)methanone To a solution of 2-bromo-6-nitro-4-(trifluoromethyl)phenol (1.78 g) in ethanol (15 mL) was added dropwise a solution of sodium hyposulfite (4.33 g) in water (15 mL) at 60° C. After dropwise addition, the reaction mixture was allowed to be cooled to room temperature, the insoluble substance was removed by filtration, and the filtrate was concentrated under reduced pressure. The residue was diluted with ethyl acetate, and the mixture was washed with saturated brine, and dried over anhydrous sodium sulfate, and the solvent was evaporated under reduced pressure to give crude 2-amino-6-bromo-4-(trifluoromethyl)phenol. The residue was purified by silica gel column chromatography (ethyl acetate/hexane) to give 2-amino-6-bromo-4-(trifluoromethyl)phenol.

To a solution of the obtained 2-amino-6-bromo-4-(trifluoromethyl)phenol and 1,2-dibromoethane (0.516 mL) in DMF (39.8 mL) was added potassium carbonate (1.377 g) at room temperature. The reaction mixture was stirred at room temperature for 1 hr, and then at 120° C. overnight, under nitrogen gas atmosphere. The reaction mixture was allowed to be cooled to room temperature, and added to water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) and basic silica gel column chromatography (ethyl acetate/hexane) to give 8-bromo-6-(trifluoromethyl)-3,4-dihydro-2H-benzo[b][1,4]oxazine.

To a solution of the obtained 8-bromo-6-(trifluoromethyl)-3,4-dihydro-2H-benzo[b][1,4]oxazine in THF (11 mL) were added cyclopropanecarbonyl chloride (0.24 mL) and triethylamine (0.307 mL) at 0° C. The mixture was stirred overnight at room temperature, the reaction mixture was added to water, and the mixture was extracted with ethyl acetate. The organic layer was washed with saturated aqueous sodium hydrogencarbonate solution and saturated brine, and dried over anhydrous magnesium sulfate, and the solvent was evaporated under reduced pressure. The residue was purified by silica gel column chromatography (ethyl acetate/hexane) to give the title compound (0.373 g).

$^1$H NMR (300 MHz, CDCl$_3$) δ 0.95 (2H, dd, J=7.9, 3.0 Hz), 1.21 (2H, dd, J=4.5, 3.0 Hz), 1.92-2.03 (1H, m), 3.96-4.08 (2H, m), 4.43-4.56 (2H, m), 7.61 (1H, dd, J=2.1, 0.6 Hz), 7.70-7.82 (1H, m).

B) cyclopropyl(8-(1,3-oxazol-5-yl)-6-(trifluoromethyl)-2,3-dihydro-4H-1,4-benzoxazin-4-yl)methanone A mixture of (8-bromo-6-(trifluoromethyl)-2H-benzo[b][1,4]oxazin-4(3H)-yl)(cyclopropyl)methanone (372 mg), 5-(4,4,5,5-tetramethyl-1,3,2-dioxaborolan-2-yl)-2-(triisopropylsilyl)-1,3-oxazole (449 mg), potassium carbonate (353 mg), Pd(PPh$_3$)$_4$ (123 mg), DME (12 mL) and water (2 mL) was stirred overnight at 80° C. under argon gas atmosphere. The reaction mixture was allowed to be cooled to room temperature, saturated aqueous ammonium chloride solution was added thereto, and the mixture was extracted with ethyl acetate. The organic layer was washed with saturated aqueous sodium hydrogencarbonate solution and saturated brine, and dried over anhydrous magnesium sulfate, and the solvent was evaporated under reduced pressure. The residue was purified by silica gel column chromatography (ethyl acetate/hexane) and basic silica gel column chromatography (ethyl acetate/hexane), and crystallized from ethyl acetate/hexane to give the title compound (91 mg).

$^1$H NMR (300 MHz, DMSO-d$_6$) δ 0.86-0.94 (2H, m, J=7.8, 2.7, 2.7 Hz), 0.94-1.02 (2H, m, J=4.9, 2.6, 2.6 Hz), 2.07-2.18 (1H, m), 4.14 (2H, t, J=4.5 Hz), 4.56-4.62 (2H, m, J=5.1 Hz), 7.69 (1H, s), 7.72 (1H, d, J=1.7 Hz), 8.10 (1H, brs), 8.52 (1H, s).

Example 56

3-(1,3-oxazol-5-yl)-N-(pyridin-2-ylmethyl)-5-(trifluoromethyl)aniline

To a solution of 3-(1,3-oxazol-5-yl)-5-(trifluoromethyl)aniline (200 mg), 2-pyridinecarboxaldehyde (0.092 mL) and acetic acid (0.188 mL) in THF (8.7 mL) was added sodium triacetoxyborohydride (743 mg). The reaction mixture was stirred overnight at 50° C. The reaction mixture was neutralized with saturated aqueous sodium hydrogencarbonate solution at 0° C., and extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) and basic silica gel column chromatography (ethyl acetate/hexane), and crystallized from ethyl acetate/hexane to give the title compound (126 mg).

$^1$H NMR (300 MHz, DMSO-d$_6$) δ 4.49 (2H, d, J=6.0 Hz), 6.90 (1H, s), 7.05 (1H, t, J=6.0 Hz), 7.18 (2H, s), 7.27 (1H, ddd, J=7.4, 4.9, 1.1 Hz), 7.40 (1H, d, J=7.7 Hz), 7.70-7.81 (2H, m), 8.44 (1H, s), 8.53-8.58 (1H, m).

Example 61

N-(6-(1,3-oxazol-5-yl)-4-(trifluoromethyl)pyridin-2-yl)cyclopropanecarboxamide

A) 6-chloro-4-(trifluoromethyl)pyridin-2-amine

A mixture of 2,6-dichloro-4-(trifluoromethyl)pyridine (10 g) and 25% aqueous ammonium solution (20 mL) was heated at 180° C. for 3 hr in sealed tube. The reaction mixture was allowed to be cooled to room temperature, and the insoluble substance was removed by filtration, and washed with ethyl acetate and water. The filtrate was washed with water and saturated brine, and dried over anhydrous sodium sulfate, and the solvent was evaporated under reduced pressure. The residue was purified by silica gel column chromatography (ethyl acetate/hexane) to give the title compound (7.98 g).

$^1$H NMR (300 MHz, CDCl$_3$) δ 4.89 (2H, brs), 6.58 (1H, s), 6.85 (1H, s).

B) N-(6-chloro-4-(trifluoromethyl)pyridin-2-yl)cyclopropanecarboxamide

To a solution of 6-chloro-4-(trifluoromethyl)pyridin-2-amine (1.275 g) in THF (50 mL) were added cyclopropanecarbonyl chloride (0.647 mL) and triethylamine (0.904 mL) at 0° C. The reaction mixture was stirred at 60° C. for 5 hr, neutralized with saturated aqueous sodium hydrogencarbonate solution at 0° C., and extracted with ethyl acetate. The organic layer was washed with water and saturated brine, and dried over anhydrous magnesium sulfate, and the solvent was evaporated under reduced pressure. The residue was purified by basic silica gel column chromatography (ethyl acetate/hexane), and crystallized from ethyl acetate/hexane to give the title compound (847 mg).

MS (API+): 265.0 [M+H]$^+$

C) N-(6-(1,3-oxazol-5-yl)-4-(trifluoromethyl)pyridin-2-yl) cyclopropanecarboxamide A mixture of N-(6-chloro-4-(trifluoromethyl)pyridin-2-yl)cyclopropanecarboxamide (846 mg), 5-(4,4,5,5-tetramethyl-1,3,2-dioxaborolan-2-yl)-2-(triisopropylsilyl)-1,3-oxazole (1.348 g), 2M aqueous sodium carbonate solution (1.598 mL), Pd(PPh$_3$)$_4$ (369 mg) and DME (12 mL) was stirred overnight at 90° C. under argon gas atmosphere. The reaction mixture was allowed to be cooled to room temperature, and the insoluble substance was removed by filtration. The filtrate was diluted with ethyl acetate, the mixture was washed with saturated aqueous sodium hydrogencarbonate solution and saturated brine, and dried over anhydrous magnesium sulfate, and the solvent was evaporated under reduced pressure. The residue was dissolved in THF (5 mL), 1M hydrochloric acid (5 mL) was added thereto, and the mixture was stirred at room temperature for 3 hr. The reaction solution was added to water, and the mixture was extracted with ethyl acetate. The organic layer was washed with saturated aqueous sodium hydrogencarbonate solution and saturated brine, and dried over anhydrous magnesium sulfate, and the solvent was evaporated under reduced pressure. The residue was purified by basic silica gel column chromatography (ethyl acetate/hexane), and crystallized from ethyl acetate/hexane to give the title compound (614 mg).

$^1$H NMR (300 MHz, DMSO-$d_6$) δ 0.88 (4H, d, J=6.4 Hz), 2.03-2.22 (1H, m), 7.81 (1H, s), 7.97 (1H, s), 8.38 (1H, s), 8.63 (1H, s), 11.44 (1H, s).

Example 62 tert-butyl 8-(1,3-oxazol-5-yl)-6-(trifluoromethyl)-2,3-dihydro-4H-1,4-benzoxazine-4-carboxylate A) tert-butyl 8-bromo-6-(trifluoromethyl)-2H-benzo[b][1,4]oxazine-4(3H)-carboxylate To a solution of 2-bromo-6-nitro-4-(trifluoromethyl)phenol (1.78 g) in ethanol (15 mL) was added dropwise a solution of sodium hyposulfite (4.33 g) in water (15 mL) at 60° C. After dropwise addition, the reaction mixture was allowed to be cooled to room temperature, the insoluble substance was removed by filtration, and the filtrate was concentrated under reduced pressure. The residue was diluted with ethyl acetate, the mixture was washed with saturated brine, and dried over anhydrous sodium sulfate, and the solvent was evaporated under reduced pressure. The residue was purified by silica gel column chromatography (ethyl acetate/hexane) to give 2-amino-6-bromo-4-(trifluoromethyl)phenol.

To a solution of the obtained 2-amino-6-bromo-4-(trifluoromethyl)phenol and 1,2-dibromoethane (0.516 mL) in DMF (39.8 mL) was added potassium carbonate (1.377 g) at room temperature. The reaction mixture was stirred at room temperature for 1 hr, and then at 120° C. overnight, under nitrogen gas atmosphere. The reaction mixture was allowed to be cooled to room temperature, and added to water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) and basic silica gel column chromatography (ethyl acetate/hexane) to give 8-bromo-6-(trifluoromethyl)-3,4-dihydro-2H-benzo[b][1,4]oxazine.

To a solution of the obtained 8-bromo-6-(trifluoromethyl)-3,4-dihydro-2H-benzo[b][1,4]oxazine in THF were added di-tert-butyl dicarbonate (0.398 mL) and N,N-dimethyl-4-aminopyridine (210 mg) at 0° C. The mixture was stirred at room temperature for 3 days, and the reaction mixture was concentrated under reduced pressure. The residue was purified by silica gel column chromatography (ethyl acetate/hexane) to give the title compound (0.377 g).

$^1$H NMR (300 MHz, DMSO-$d_6$) δ 1.49 (9H, s), 3.87 (2H, s), 4.41 (2H, s), 7.66 (1H, d, J=1.9 Hz), 8.15 (1H, s).

B) tert-butyl 8-(1,3-oxazol-5-yl)-6-(trifluoromethyl)-2,3-dihydro-4H-1,4-benzoxazine-4-carboxylate A mixture of tert-butyl 8-bromo-6-(trifluoromethyl)-2H-benzo[b][1,4]oxazine-4(3H)-carboxylate (377 mg), 5-(4,4,5,5-tetramethyl-1,3,2-dioxaborolan-2-yl)-2-(triisopropylsilyl)-1,3-oxazole (416 mg), potassium carbonate (327 mg), Pd(PPh$_3$)$_4$ (114 mg), DME (6 mL) and water (1 mL) was stirred at 80° C. overnight under argon gas atmosphere. The reaction mixture was allowed to be cooled to room temperature, water was added thereto, and the mixture was extracted with ethyl acetate. The organic layer was washed with saturated aqueous sodium hydrogencarbonate solution and saturated brine, and dried over anhydrous magnesium sulfate, and the solvent was evaporated under reduced pressure. The residue was dissolved in THF (3 mL), 1M hydrochloric acid (3 mL) was added thereto, and the mixture was stirred at room temperature for 1 hr. The reaction solution was added to water, and the mixture was extracted with ethyl acetate. The organic layer was washed with saturated aqueous sodium hydrogencarbonate solution and saturated brine, and dried over anhydrous magnesium sulfate, and the solvent was evaporated under reduced pressure. The residue was purified by silica gel column chromatography (ethyl acetate/hexane), and crystallized from ethyl acetate/hexane to give the title compound (165 mg).

$^1$H NMR (300 MHz, DMSO-$d_6$) δ 1.51 (9H, s), 3.89-3.95 (2H, m, J=4.7 Hz), 4.48-4.55 (2H, m, J=4.3 Hz), 7.65-7.68 (2H, m), 8.15 (1H, brs), 8.51 (1H, s).

Example 80

2-methyl-1-(4-(1,3-oxazol-5-yl)-6-(trifluoromethyl)-2,3-dihydro-1H-indol-1-yl)propan-1-one A) 1-(4-bromo-6-(trifluoromethyl)indolin-1-yl)-2-methylpropan-1-one To a solution of 4-bromo-6-(trifluoromethyl)indoline (300 mg) in THF (6 mL) were added isobutyryl chloride (0.143 mL) and pyridine (0.118 mL) at 0° C. The mixture was stirred at room temperature for 30 min, the reaction mixture was added to water, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane), and crystallized from ethyl acetate/hexane to give the title compound (328 mg).

$^1$H NMR (300 MHz, CDCl$_3$) δ 1.24 (6H, d, J=6.4 Hz), 2.70-2.87 (1H, m), 3.17-3.30 (2H, m), 4.23 (2H, t, J=8.7 Hz), 7.43 (1H, s), 8.53 (1H, brs).

B) 2-methyl-1-(4-(1,3-oxazol-5-yl)-6-(trifluoromethyl)-2,3-dihydro-1H-indol-1-yl)propan-1-one A mixture of 1-(4-bromo-6-(trifluoromethyl)indolin-1-yl)-2-methylpropan-1-one (328 mg), 5-(4,4,5,5-tetramethyl-1,3,2-dioxaborolan-2-yl)-2-(triisopropylsilyl)-1,3-oxazole (411 mg), potassium carbonate (270 mg), Pd(PPh$_3$)$_4$ (113 mg), DME (3 mL) and water (0.6 mL) was irradiated with microwave at 120° C. for 30 min under nitrogen gas atmosphere. The mixture was allowed to be cooled to room temperature, water was added thereto, and the mixture was extracted with ethyl acetate. The organic layer was washed with water and saturated brine, and dried over anhydrous sodium sulfate, and the solvent was evaporated under reduced pressure. The residue was dissolved in THF (6 mL), 1M hydrochloric acid (1 mL) was added thereto, and the mixture was stirred at room temperature for 30 min. The reaction solution was added to water, and the mixture was extracted with ethyl acetate. The organic layer was washed with water and saturated brine, and dried over anhydrous sodium sulfate, and the solvent was evaporated under reduced pressure. The residue was crystallized from ethyl acetate/hexane to give the title compound (167 mg).

$^1$H NMR (300 MHz, CDCl$_3$) δ 1.26 (6H, d, J=6.8 Hz), 2.74-2.92 (1H, m), 3.42 (2H, t, J=8.5 Hz), 4.31 (2H, t, J=8.7 Hz), 7.33 (1H, s), 7.65 (1H, s), 8.00 (1H, s), 8.62 (1H, brs).

Example 83 morpholin-4-yl(4-(1,3-oxazol-5-yl)-6-(trifluoromethyl)-2,3-dihydro-1H-indol-1-yl)methanone A) (4-bromo-6-(trifluoromethyl)indolin-1-yl) (morpholino)methanone To a solution of 4-bromo-6-(trifluoromethyl)indoline (100 mg) in ethyl acetate (2 mL) were added triethylamine (0.063 mL) and bis(trichloromethyl)carbonate (134 mg) at 0° C. The reaction mixture was stirred at 0° C. for 20 min, saturated aqueous sodium hydrogencarbonate solution was added thereto, and the mixture was extracted with ethyl acetate. The organic layer was washed with saturated brine, and dried over anhydrous magnesium sulfate, and the solvent was evaporated under reduced pressure. The residue was dissolved in THF (2 mL), and triethylamine (0.063 mL) and morpholine (0.039 mL) were added thereto. The mixture was stirred at room temperature for 30 min, saturated aqueous sodium hydrogencarbonate solution was added thereto, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (110 mg).

$^1$H NMR (300 MHz, CDCl$_3$) δ 3.09 (2H, t, J=8.3 Hz), 3.35-3.44 (4H, m), 3.72-3.81 (4H, m), 4.03 (2H, t, J=8.5 Hz), 7.24 (1H, s), 7.32 (1H, s).

B) morpholin-4-yl(4-(1,3-oxazol-5-yl)-6-(trifluoromethyl)-2,3-dihydro-1H-indol-1-yl)methanone A mixture of (4-bromo-6-(trifluoromethyl)indolin-1-yl) (morpholino)methanone (110 mg), 5-(4,4,5,5-tetramethyl-1, 3,2-dioxaborolan-2-yl)-2-(triisopropylsilyl)-1,3-oxazole (122 mg), potassium carbonate (80 mg), Pd(PPh$_3$)$_4$ (33.5 mg), DME (1 mL) and water (0.2 mL) was irradiated with microwave at 120° C. for 30 min under nitrogen gas atmosphere. The mixture was allowed to be cooled to room temperature, water was added thereto, and the mixture was extracted with ethyl acetate/THF. The organic layer was washed with water and saturated brine, and dried over anhydrous sodium sulfate, and the solvent was evaporated under reduced pressure. The residue was purified by silica gel column chromatography (ethyl acetate/hexane) to give a white solid. The obtained white solid was dissolved in THF (4 mL), 1M hydrochloric acid (1 mL) was added thereto, and the mixture was stirred at room temperature for 30 min. The reaction solution was added to water, and the mixture was extracted with ethyl acetate. The organic layer was washed with water and saturated brine, and dried over anhydrous sodium sulfate, and the solvent was evaporated under reduced pressure. The residue was crystallized from ethyl acetate/hexane to give the title compound (46 mg).

$^1$H NMR (300 MHz, CDCl$_3$) δ 3.27 (2H, t, J=8.3 Hz), 3.39-3.46 (4H, m), 3.75-3.82 (4H, m), 4.09 (2H, t, J=8.5 Hz), 7.30-7.35 (2H, m), 7.54 (1H, s), 8.00 (1H, s).

Example 87

(4-(1,3-oxazol-5-yl)-6-(trifluoromethyl)-2,3-dihydro-1H-indol-1-yl)(tetrahydro-2H-pyran-4-yl)methanone A) (4-bromo-6-(trifluoromethyl)indolin-1-yl) (tetrahydro-2H-pyran-4-yl)methanone To a solution of tetrahydro-2H-pyran-4-carbonyl chloride (201 mg) in THF (6 mL) were added 4-bromo-6-(trifluoromethyl)indoline (300 mg) and pyridine (0.109 mL) at 0° C. The mixture was stirred at room temperature for 30 min, the reaction mixture was added to 1M hydrochloric acid, and the mixture was extracted with ethyl acetate. The organic layer was washed with 1M hydrochloric acid and saturated brine, and dried over anhydrous sodium sulfate, and the solvent was evaporated under reduced pressure. The residue was purified by silica gel column chromatography (ethyl acetate/hexane) to give the title compound (394 mg).

$^1$H NMR (300 MHz, CDCl$_3$) δ 1.73 (2H, d, J=13.2 Hz), 1.92-2.12 (2H, m), 2.73 (1H, t, J=11.3 Hz), 3.25 (2H, t, J=8.5 Hz), 3.49 (2H, t, J=11.9 Hz), 4.09 (2H, d, J=11.7 Hz), 4.25 (2H, t, J=8.5 Hz), 7.45 (1H, s), 8.52 (1H, brs).

B) (4-(1,3-oxazol-5-yl)-6-(trifluoromethyl)-2,3-dihydro-1H-indol-1-yl)(tetrahydro-2H-pyran-4-yl)methanone A mixture of (4-bromo-6-(trifluoromethyl)indolin-1-yl) (tetrahydro-2H-pyran-4-yl)methanone (394 mg), 5-(4,4,5,5-tetramethyl-1,3,2-dioxaborolan-2-yl)-2-(triisopropylsilyl)-1,3-oxazole (439 mg), 3M aqueous potassium carbonate solution (0.695 mL), Pd(PPh$_3$)$_4$ (120 mg) and DME (4 mL) was irradiated with microwave at 120° C. for 30 min under nitrogen gas atmosphere. The mixture was allowed to be cooled to room temperature, water was added thereto, and the mixture was extracted with ethyl acetate. The organic layer was washed with water and saturated brine, and dried over anhydrous sodium sulfate, and the solvent was evaporated under reduced pressure. The residue was dissolved in THF (3 mL), 1M hydrochloric acid (1 mL) was added thereto, and the mixture was stirred overnight at room temperature. The reaction solution was added to water, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane), and crystallized from ethyl acetate/hexane to give the title compound (180 mg).

$^1$H NMR (300 MHz, CDCl$_3$) δ 1.76 (2H, d, J=13.6 Hz), 1.93-2.13 (2H, m), 2.77 (1H, t, J=10.7 Hz), 3.36-3.58 (4H, m), 4.10 (2H, dd, J=11.7, 1.9 Hz), 4.32 (2H, t, J=8.7 Hz), 7.33 (1H, s), 7.66 (1H, s), 8.00 (1H, s), 8.61 (1H, brs).

Example 89

4,4-difluoro-1-(3-(1,3-oxazol-5-yl)-5-(trifluoromethyl)phenyl)piperidine

A) 1-(3-bromo-5-(trifluoromethyl)phenyl)-4,4-difluoropiperidine

To a solution of 3-bromo-5-fluorobenzotrifluoride (1.48 g) in DMSO (10 mL) were added 4,4-difluoropiperidine hydrochloride (1.15 g), triethylamine (887 mg) and cesium carbonate (2.86 g) at 20° C. The reaction mixture was stirred at 90° C. for 16 hr. In the same manner as in the above-mentioned procedure, the reaction mixture was obtained using 3-bromo-5-fluorobenzotrifluoride (1.48 g), DMSO (10 mL), 4,4-difluoropiperidine hydrochloride (1.15 g), triethylamine (887 mg) and cesium carbonate (2.86 g), and the two reaction mixtures were combined, and the following procedure was performed. The reaction mixture was diluted with ethyl acetate, and the mixture was washed with water and saturated brine, and dried over anhydrous sodium sulfate, and the solvent was evaporated under reduced pressure. The residue was purified by silica gel column chromatography (ethyl acetate/petroleum ether) to give the title compound (369 mg).

$^1$H NMR (400 MHz, CDCl$_3$) δ 2.03-2.15 (4H, m), 3.38-3.43 (4H, m), 7.03 (1H, s), 7.19 (1H, s), 7.21 (1H, d, J=0.8 Hz).

B) 4,4-difluoro-1-(3-(1,3-oxazol-5-yl)-5-(trifluoromethyl)phenyl)piperidine

A mixture of 1-(3-bromo-5-(trifluoromethyl)phenyl)-4,4-difluoropiperidine (150 mg), 5-(4,4,5,5-tetramethyl-1,3,2-dioxaborolan-2-yl)-2-(triisopropylsilyl)-1,3-oxazole (169 mg), potassium carbonate (179 mg), Pd(PPh$_3$)$_4$ (25 mg), 1,4-dioxane (9 mL) and water (3 mL) was stirred at 80° C. for 40 hr under nitrogen gas atmosphere. The reaction mixture was concentrated under reduced pressure, and the residue was allowed to be cooled to room temperature, and diluted with ethyl acetate. The organic layer was washed with water and saturated brine, and dried over anhydrous sodium sulfate, and the solvent was evaporated under reduced pressure. The residue was purified by preparative thin layer chromatography (ethyl acetate/petroleum ether) to give the title compound (80 mg).

$^1$H NMR (400 MHz, CDCl$_3$) δ 2.08-2.19 (4H, m), 3.45-3.48 (4H, m), 7.10 (1H, s), 7.34 (1H, s), 7.37 (1H, s), 7.42 (1H, d, J=2.4 Hz), 7.94 (1H, d, J=4.8 Hz).

Example 95

(3S)-1-(3-(1,3-oxazol-5-yl)-5-(trifluoromethyl)phenyl)pyrrolidin-3-ol

A) (S)-1-(3-bromo-5-(trifluoromethyl)phenyl)pyrrolidin-3-ol

A mixture of 3-bromo-5-fluorobenzotrifluoride (1.07 g), (S)-3-pyrrolidinol (0.391 mL), cesium carbonate (1.72 g) and DMSO (10 mL) was irradiated with microwave at 120° C. for 30 min. The mixture was allowed to be cooled to room temperature, saturated aqueous sodium bicarbonate solution was added thereto, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (1.05 g).

MS (API+): 310.0 [M+H]$^+$

B) (3S)-1-(3-(1,3-oxazol-5-yl)-5-(trifluoromethyl)phenyl)pyrrolidin-3-ol

A mixture of (S)-1-(3-bromo-5-(trifluoromethyl)phenyl)pyrrolidin-3-ol (1.05 g), 5-(4,4,5,5-tetramethyl-1,3,2-dioxaborolan-2-yl)-2-(triisopropylsilyl)-1,3-oxazole (1.312 g), 2M aqueous sodium carbonate solution (1.868 mL), Pd(PPh$_3$)$_4$ (392 mg) and DME (15 mL) was irradiated with microwave at 120° C. for 30 min. The mixture was allowed to be cooled to room temperature, saturated aqueous sodium bicarbonate solution was added thereto, and the mixture was extracted with ethyl acetate. The organic layer was washed with water and saturated brine, and dried over anhydrous magnesium sulfate, and the solvent was evaporated under reduced pressure. The residue was dissolved in THF (10 mL), 1M hydrochloric acid (10 mL) was added thereto, and the mixture was stirred at room temperature for 1 hr. The reaction solution was neutralized with saturated aqueous sodium hydrogencarbonate solution at 0° C., and extracted with ethyl acetate. The organic layer was washed with water and saturated brine, and dried over anhydrous sodium sulfate, and the solvent was evaporated under reduced pressure. The residue was purified by basic silica gel column chromatography (ethyl acetate/hexane), and crystallized from ethyl acetate/hexane to give the title compound (513 mg).

$^1$H NMR (300 MHz, DMSO-d$_6$) δ 1.73 (1H, d, J=4.5 Hz), 2.07-2.32 (2H, m), 3.36 (1H, d, J=10.5 Hz), 3.46 (1H, td, J=8.9, 3.4 Hz), 3.54-3.66 (2H, m), 4.68 (1H, s), 6.72 (1H, s), 6.94 (1H, s), 7.19 (1H, s), 7.39 (1H, s), 7.93 (1H, s).

Example 96

1-(6-(1,3-oxazol-5-yl)-4-(trifluoromethyl)pyridin-2-yl)pyrrolidin-3-ol

A) 1-(6-chloro-4-(trifluoromethyl)pyridin-2-yl)pyrrolidin-3-ol

A mixture of 2,6-dichloro-4-(trifluoromethyl)pyridine (1.00 g), (S)-3-pyrrolidinol (0.385 mL), N-ethyldiisopropylamine (0.801 mL) and N-methyl-2-pyrrolidone (10 mL) was irradiated with microwave at 120° C. for 1 hr. The mixture was allowed to be cooled to room temperature, water was added thereto, and the mixture was extracted with ethyl acetate. The organic layer was washed with water and saturated brine, and dried over anhydrous magnesium sulfate, and the solvent was evaporated under reduced pressure. The residue was purified by basic silica gel column chromatography (ethyl acetate/hexane) to give the title compound (1.29 g).

MS (API+): 267.1[M+H]$^+$

B) 1-(6-(1,3-oxazol-5-yl)-4-(trifluoromethyl)pyridin-2-yl)pyrrolidin-3-ol

A mixture of 1-(6-chloro-4-(trifluoromethyl)pyridin-2-yl)pyrrolidin-3-ol (1.23 g), 5-(4,4,5,5-tetramethyl-1,3,2-dioxaborolan-2-yl)-2-(triisopropylsilyl)-1,3-oxazole (1.79 g), 2M aqueous sodium carbonate solution (2.55 mL), Pd(PPh$_3$)$_4$ (535 mg) and DME (15 mL) was irradiated with microwave at 120° C. for 30 min. The mixture was allowed to be cooled to room temperature, saturated aqueous sodium bicarbonate solution was added thereto, and the mixture was extracted with ethyl acetate. The organic layer was washed with water and saturated brine, and dried over anhydrous magnesium sulfate, and the solvent was evaporated under reduced pressure. The residue was dissolved in THF (10 mL), 1M hydrochloric acid (10 mL) was added thereto, and the mixture was stirred at room temperature for 1 hr. The reaction solution was neutralized with saturated aqueous sodium hydrogencarbonate solution at 0° C., and extracted with ethyl acetate. The organic layer was washed with water and saturated brine, and dried over anhydrous magnesium sulfate, and the solvent was evaporated under reduced pressure. The residue was purified by basic silica gel column chromatography (ethyl acetate/hexane), and crystallized from ethyl acetate/hexane to give the title compound (986 mg).

¹H NMR (300 MHz, DMSO-d₆) δ 2.00 (2H, s), 3.38-3.66 (4H, m), 4.42 (1H, brs), 5.02 (1H, d, J=2.3 Hz), 6.67 (1H, s), 7.11 (1H, s), 7.81 (1H, s), 8.53 (1H, s).

Example 107

1-(4-(3-(1,3-oxazol-5-yl)-5-(trifluoromethyl)phenyl) piperazin-1-yl)ethanone

A) tert-butyl 4-(3-bromo-5-(trifluoromethyl)phenyl) piperazine-1-carboxylate

To a solution of 3-bromo-5-fluorobenzotrifluoride (1.00 g) in DMSO (10 mL) were added 1-(tert-butoxycarbonyl)piperazine (0.916 g) and cesium carbonate (1.88 g) at 20° C. The reaction mixture was stirred at 90° C. for 16 hr. To the reaction mixture was added water, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/petroleum ether) to give the title compound (471 mg).

¹H NMR (400 MHz, CDCl₃) δ 1.51 (9H, s), 3.22 (4H, t, J=4.8 Hz), 3.60 (4H, t, J=5.2 Hz), 7.03 (1H, s), 7.18 (1H, s), 7.23 (1H, s).

B) 1-(4-(3-bromo-5-(trifluoromethyl)phenyl)piperazin-1-yl)ethanone tert-Butyl 4-(3-bromo-5-(trifluoromethyl)phenyl)piperazine-1-carboxylate (570 mg) was dissolved in 4M hydrogen chloride/ethyl acetate solution (6 mL), and the solution was stirred at 20° C. for 12 hr. The reaction mixture was diluted with ethyl acetate, and neutralized with saturated aqueous sodium hydrogencarbonate solution. The organic layer was washed with water and saturated brine, and dried over anhydrous sodium sulfate, and the solvent was evaporated under reduced pressure to give crude 1-(3-bromo-5-(trifluoromethyl)phenyl)piperazine (380 mg).

To a solution of the crude 1-(3-bromo-5-(trifluoromethyl) phenyl)piperazine (100 mg) in dichloromethane (3 mL) were added acetyl chloride (30 mg) and triethylamine (1 mL). The reaction mixture was stirred at 20° C. for 4 hr. The reaction mixture was diluted with dichloromethane, washed with water and saturated brine, and dried over anhydrous sodium sulfate, and the solvent was evaporated under reduced pressure. The residue was purified by preparative thin layer chromatography (ethyl acetate/petroleum ether) to give the title compound (70 mg).

¹H NMR (400 MHz, CDCl₃) δ 2.15 (3H, s), 3.21-3.28 (4H, m), 3.64 (2H, t, J=5.2 Hz), 3.78 (2H, t, J=5.6 Hz), 7.02 (1H, s), 7.16 (1H, s), 7.23 (1H, s).

C) 1-(4-(3-(1,3-oxazol-5-yl)-5-(trifluoromethyl)phenyl)piperazin-1-yl)ethanone

A mixture of 1-(4-(3-bromo-5-(trifluoromethyl)phenyl)piperazin-1-yl)ethanone (120 mg), 5-(4,4,5,5-tetramethyl-1,3,2-dioxaborolan-2-yl)-2-(triisopropylsilyl)-1,3-oxazole (132 mg), potassium carbonate (141 mg), Pd(PPh₃)₄ (20 mg), 1,4-dioxane (9 mL) and water (3 mL) was stirred at 80° C. for 40 hr under nitrogen gas atmosphere. The reaction mixture was diluted with ethyl acetate, washed with water and saturated brine, and dried over anhydrous sodium sulfate, and the solvent was evaporated under reduced pressure. The residue was purified by preparative thin layer chromatography (ethyl acetate/petroleum ether) to give the title compound (58 mg).

¹H NMR (300 MHz, CDCl₃) δ 2.16 (3H, s), 3.25-3.34 (4H, m), 3.67 (2H, t, J=5.2 Hz), 3.82 (2H, t, J=5.2 Hz), 7.08 (1H, s), 7.32 (1H, s), 7.39 (1H, s), 7.42 (1H, s), 7.94 (1H, s).

Example 127

3,3-dimethyl-1-(3-(1,3-oxazol-5-yl)-5-(trifluoromethyl)phenyl)pyrrolidin-2-one

A) 5-(3-bromo-5-(trifluoromethyl)phenyl)-1,3-oxazole

To a solution of 3-bromo-5-(trifluoromethyl)benzaldehyde (3.02 g) and p-toluenesulfonylmethyl isocyanide (2.56 g) in methanol (59.7 mL) was added potassium carbonate (3.46 g) at room temperature, and the mixture was heated with reflux for 2 hr. The solvent was evaporated under reduced pressure, to the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (3.24 g).

¹H NMR (300 MHz, DMSO-d₆) δ 7.98 (1H, s), 8.03 (1H, s), 8.07 (1H, s), 8.27 (1H, s), 8.57 (1H, s).

B) 3,3-dimethyl-1-(3-(1,3-oxazol-5-yl)-5-(trifluoromethyl)phenyl)pyrrolidin-2-one To a solution of 5-(3-bromo-5-(trifluoromethyl)phenyl)-1,3-oxazole (300 mg), 3,3-dimethylpyrrolidin-2-one (0.126 mL) and Xantphos (59.4 mg) in 1,4-dioxane (3 mL) were added Pd₂(dba)₃ (47 mg) and cesium carbonate (502 mg). The reaction mixture was irradiated with microwave at 120° C. for 1 hr. The mixture was allowed to be cooled to room temperature, water was added thereto, and the mixture was extracted with ethyl acetate. The organic layer was washed with saturated aqueous sodium hydrogencarbonate solution and saturated brine, and dried over anhydrous magnesium sulfate, and the solvent was evaporated under reduced pressure. The residue was purified by silica gel column chromatography (ethyl acetate/hexane) and basic silica gel column chromatography (ethyl acetate/hexane) to give the title compound (68.2 mg).

¹H NMR (300 MHz, CDCl₃) δ 1.30 (6H, s), 2.08 (2H, t, J=7.0 Hz), 3.86 (2H, t, J=6.8 Hz), 7.48 (1H, s), 7.67 (1H, s), 7.83 (1H, s), 7.96 (1H, s), 8.37 (1H, s).

Example 128

(1S,4S)-5-(6-(1,3-oxazol-5-yl)-4-(trifluoromethyl) pyridin-2-yl)-2-oxa-5-azabicyclo[2.2.1]heptane To a solution of 4-bromo-6-(trifluoromethyl)indoline (100 mg) in ethyl acetate (2 mL) were added triethylamine (0.063 mL) and bis(trichloromethyl)carbonate (134 mg) at 0° C. The reaction mixture was stirred at 0° C. for 20 min, saturated aqueous sodium hydrogencarbonate solution was added thereto, and the mixture was extracted with ethyl acetate. The organic layer was dried over anhydrous magnesium sulfate, and the solvent was evaporated under reduced pressure. The residue was dissolved in THF (2 mL), and triethylamine (0.126 mL) and 2-oxa-5-azabicyclo[2.2.1]heptane hydrochloride (61.2 mg) were added thereto. The mixture was stirred at room temperature for 2 hr, saturated aqueous sodium hydrogencarbonate solution was added thereto, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give 2-oxa-5-azabicyclo[2.2.1]heptan-5-yl(4-bromo-6-(trifluoromethyl)indolin-1-yl)methanone.

A mixture of the obtained 2-oxa-5-azabicyclo[2.2.1]heptan-5-yl(4-bromo-6-(trifluoromethyl)indolin-1-yl)methanone, 5-(4,4,5,5-tetramethyl-1,3,2-dioxaborolan-2-yl)-2-(triisopropylsilyl)-1,3-oxazole (147 mg), potassium carbonate (105 mg), Pd(PPh$_3$)$_4$ (44 mg), DME (2 mL) and water (0.5 mL) was irradiated with microwave at 120° C. for 30 min under nitrogen gas atmosphere. The mixture was allowed to be cooled to room temperature, water was added thereto, and the mixture was extracted with ethyl acetate. The organic layer was dried over anhydrous magnesium sulfate, and the solvent was evaporated under reduced pressure. The residue was dissolved in THF (2 mL), 1M hydrochloric acid (0.5 mL) was added thereto, and the mixture was stirred at room temperature for 2 hr. The reaction solution was neutralized with saturated aqueous sodium hydrogencarbonate solution, and extracted with ethyl acetate. The organic layer was dried over anhydrous magnesium sulfate, and the solvent was evaporated under reduced pressure. The residue was purified by silica gel column chromatography (ethyl acetate/hexane), and crystallized from ethyl acetate/hexane to give the title compound (34 mg).

$^1$H NMR (300 MHz, DMSO-d$_6$) δ 1.75-1.89 (2H, m), 3.26-3.41 (3H, m), 3.47-3.59 (1H, m), 3.75 (1H, dd, J=7.4, 1.3 Hz), 3.90-4.24 (3H, m), 4.45-4.65 (2H, m), 7.56 (1H, s), 7.64-7.77 (2H, m), 8.56 (1H, s).

The compounds of Examples produced according to the above-mentioned methods or a method analogous thereto are shown in the following tables. MS in the tables means actual measured value.

TABLE 1-1

| Example No. | IUPAC Name | Structure | MS |
|---|---|---|---|
| 1 | 3-chloro-N-(3-(1,3-oxazol-5-yl)-5-(trifluoromethyl)phenyl)benzamide | 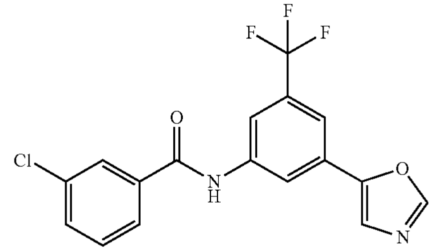 [SMILES: O=C(Nc1cc(-c2cnco2)cc(C(F)(F)F)c1)c1cccc(Cl)c1] | 367.0 |
| 2 | 3-chloro-N-(3-(1,3-oxazol-5-yl)-5-(trifluoromethyl)phenyl)benzenesulfonamide | 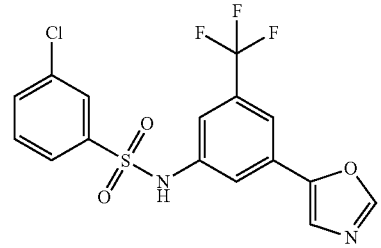 [SMILES: O=S(=O)(Nc1cc(-c2cnco2)cc(C(F)(F)F)c1)c1cccc(Cl)c1] | 402.9 |
| 3 | 3-chloro-N-(3-isopropyl-5-(1,3-oxazol-5-yl)phenyl)benzamide | 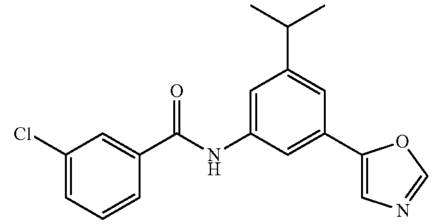 [SMILES: CC(C)c1cc(NC(=O)c2cccc(Cl)c2)cc(-c2cnco2)c1] | 341.1 |
| 4 | 3-chloro-N-(3-isopropyl-5-(1,3-oxazol-5-yl)phenyl)benzenesulfonamide | 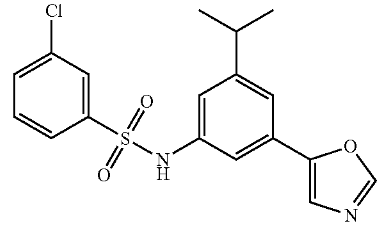 [SMILES: CC(C)c1cc(NS(=O)(=O)c2cccc(Cl)c2)cc(-c2cnco2)c1] | 377.1 |

TABLE 1-1-continued

| Example No. | IUPAC Name | Structure | MS |
|---|---|---|---|
| 5 | 3-chloro-N-(3-cyclopropyl-5-(1,3-oxazol-5-yl)phenyl)benzamide | 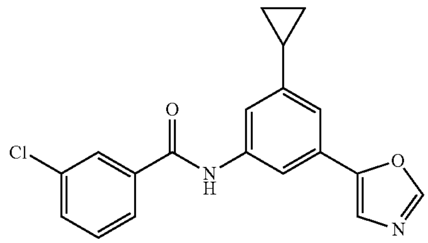 [SMILES: O=C(Nc1cc(-c2cnco2)cc(C2CC2)c1)c1cccc(Cl)c1] | 339.1 |
| 6 | N-(3-(1,3-oxazol-5-yl)-5-(trifluoromethyl)phenyl)benzamide | 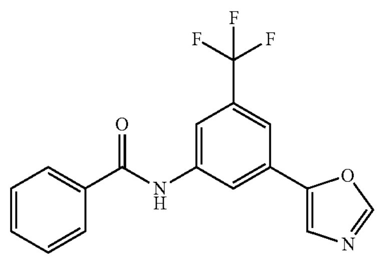 [SMILES: O=C(Nc1cc(-c2cnco2)cc(C(F)(F)F)c1)c1ccccc1] | 333.1 |
| 7 | 3-chloro-N-(3-cyano-5-(1,3-oxazol-5-yl)phenyl)benzamide | 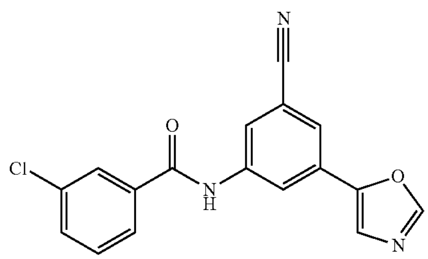 [SMILES: N#Cc1cc(NC(=O)c2cccc(Cl)c2)cc(-c2cnco2)c1] | 322.0 |
| 8 | 3-chloro-N-(3-cyano-5-(1,3-oxazol-5-yl)phenyl)benzenesulfonamide | 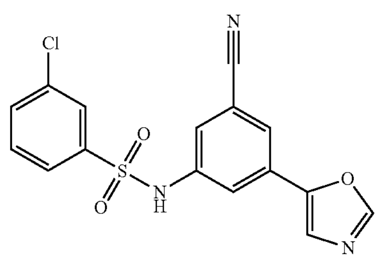 [SMILES: N#Cc1cc(NS(=O)(=O)c2cccc(Cl)c2)cc(-c2cnco2)c1] | 357.9 |
| 9 | 3-chloro-N-(7-(1,3-oxazol-5-yl)-2,3-dihydro-1-benzofuran-5-yl)benzamide | 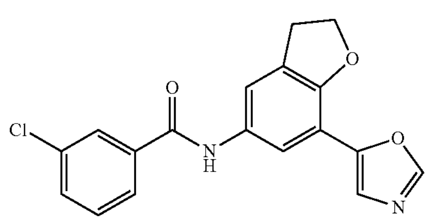 [SMILES: O=C(Nc1cc2c(c(-c3cnco3)c1)OCC2)c1cccc(Cl)c1] | 341.1 |
| 10 | 3-chloro-N-(7-(1,3-oxazol-5-yl)-2,3-dihydro-1-benzofuran-5-yl)benzenesulfonamide | 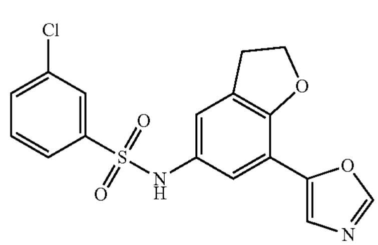 [SMILES: O=S(=O)(Nc1cc2c(c(-c3cnco3)c1)OCC2)c1cccc(Cl)c1] | 377.1 |

TABLE 1-2

| Example No. | IUPAC Name | Structure | MS |
|---|---|---|---|
| 11 | N-(3-(1,3-oxazol-5-yl)-5-(trifluoromethyl)phenyl)acetamide | 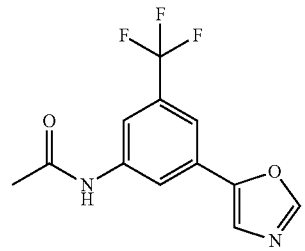 [SMILES: CC(=O)Nc1cc(-c2cnco2)cc(C(F)(F)F)c1] | 269.0 |
| 12 | N-(3-(1,3-oxazol-5-yl)-5-(trifluoromethyl)phenyl)thiophene-2-carboxamide | 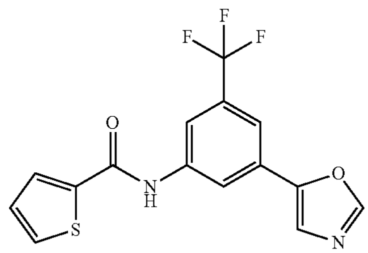 [SMILES: O=C(Nc1cc(-c2cnco2)cc(C(F)(F)F)c1)c1cccs1] | 336.9 |
| 13 | N-(3-(1,3-oxazol-5-yl)-5-(trifluoromethyl)phenyl)nicotinamide | 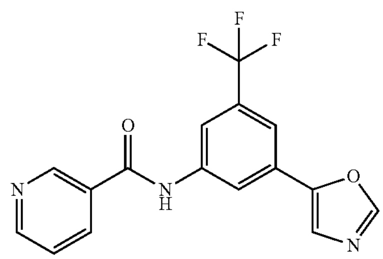 [SMILES: O=C(Nc1cc(-c2cnco2)cc(C(F)(F)F)c1)c1cccnc1] | 332.0 |
| 14 | 4-methoxy-N-(3-(1,3-oxazol-5-yl)-5-(trifluoromethyl)phenyl)benzamide | 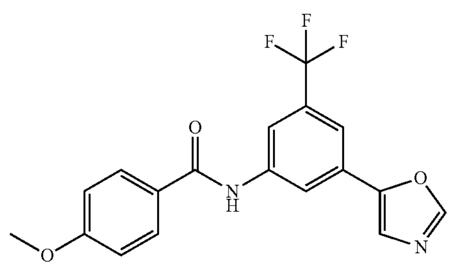 [SMILES: COc1ccc(C(=O)Nc2cc(-c3cnco3)cc(C(F)(F)F)c2)cc1] | 363.1 |
| 15 | N-(3-(1,3-oxazol-5-yl)-5-(trifluoromethyl)phenyl)cyclohexane carboxamide | 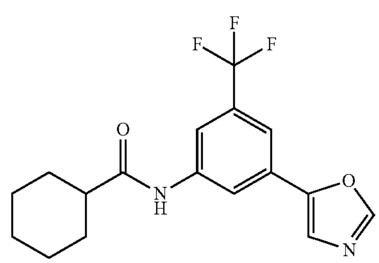 [SMILES: O=C(Nc1cc(-c2cnco2)cc(C(F)(F)F)c1)C1CCCCC1] | 336.8 |
| 16 | N-(3-(1,3-oxazol-5-yl)-5-(trifluoromethyl)phenyl)pyridine-2-carboxamide | 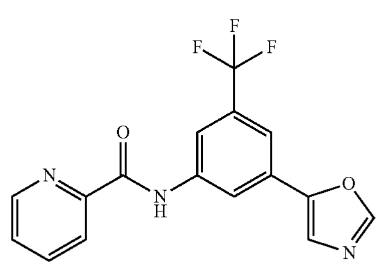 [SMILES: O=C(Nc1cc(-c2cnco2)cc(C(F)(F)F)c1)c1ccccn1] | 332.0 |

TABLE 1-2-continued

| Example No. | IUPAC Name | Structure | MS |
|---|---|---|---|
| 17 | N-(3-(1,3-oxazol-5-yl)-5-(trifluoromethyl)phenyl)cyclopropanecarboxamide | 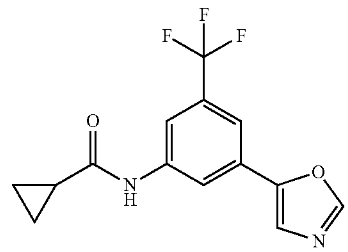 | 294.9 |
| 18 | 2-methoxy-N-(3-(1,3-oxazol-5-yl)-5-(trifluoromethyl)phenyl)acetamide | 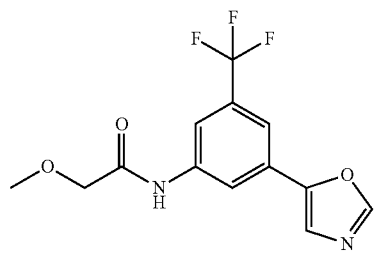 [SMILES: COCC(=O)Nc1cc(-c2cnco2)cc(C(F)(F)F)c1] | 299.0 |
| 19 | 2-chloro-N-(3-(1,3-oxazol-5-yl)-5-(trifluoromethyl)phenyl)benzamide | 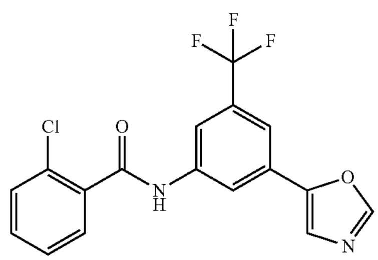 [SMILES: O=C(Nc1cc(-c2cnco2)cc(C(F)(F)F)c1)c1ccccc1Cl] | 364.9 |
| 20 | 2-methyl-N-(3-(1,3-oxazol-5-yl)-5-(trifluoromethyl)phenyl)propanamide | 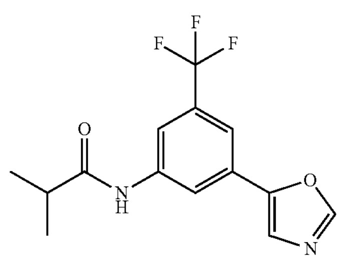 [SMILES: CC(C)C(=O)Nc1cc(-c2cnco2)cc(C(F)(F)F)c1] | 296.9 |

TABLE 1-3

| Example No. | IUPAC Name | Structure | MS |
|---|---|---|---|
| 21 | N-(3-(1,3-oxazol-5-yl)-5-(trifluoromethyl)phenyl)butanamide | 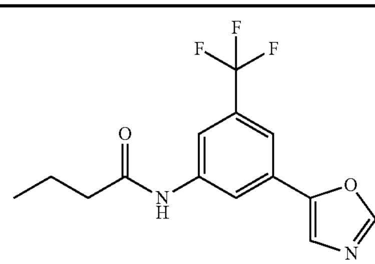 | 296.9 |

TABLE 1-3-continued

| Example No. | IUPAC Name | Structure | MS |
|---|---|---|---|
| 22 | N-(3-(1,3-oxazol-5-yl)-5-(trifluoromethyl)phenyl)cyclopentanecarboxamide | 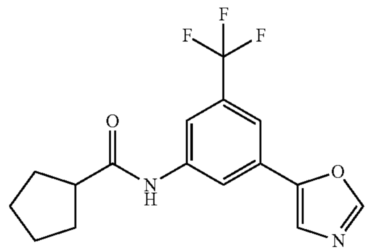 [SMILES: O=C(Nc1cc(-c2cnco2)cc(C(F)(F)F)c1)C1CCCC1] | 322.9 |
| 23 | 2,5-dimethyl-N-(3-(1,3-oxazol-5-yl)-5-(trifluoromethyl)phenyl)-3-furamide | 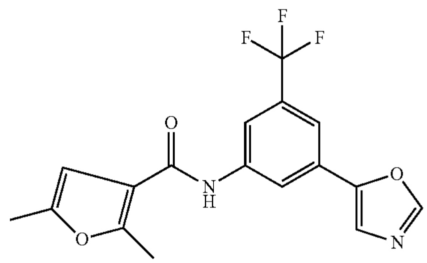 [SMILES: Cc1cc(C(=O)Nc2cc(-c3cnco3)cc(C(F)(F)F)c2)c(C)o1] | 349.0 |
| 24 | 3-methyl-N-(3-(1,3-oxazol-5-yl)-5-(trifluoromethyl)phenyl)butanamide | 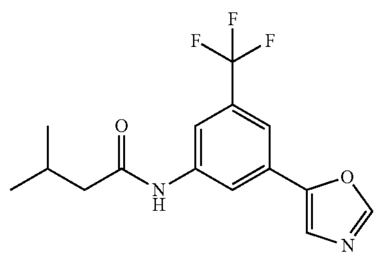 [SMILES: CC(C)CC(=O)Nc1cc(-c2cnco2)cc(C(F)(F)F)c1] | 310.9 |
| 25 | 4-chloro-N-(3-(1,3-oxazol-5-yl)-5-(trifluoromethyl)phenyl)benzamide | 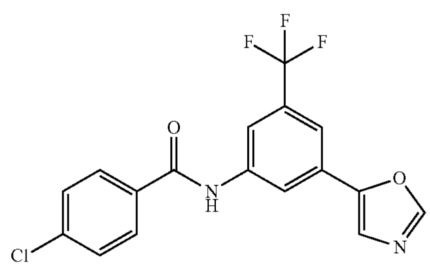 [SMILES: O=C(Nc1cc(-c2cnco2)cc(C(F)(F)F)c1)c1ccc(Cl)cc1] | 364.9 |
| 26 | 3-chloro-N-(3-chloro-5-(1,3-oxazol-5-yl)phenyl)benzamide | 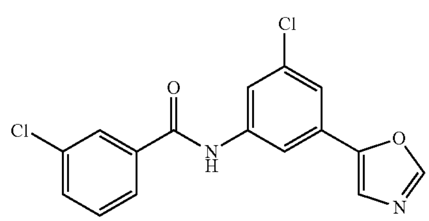 [SMILES: O=C(Nc1cc(Cl)cc(-c2cnco2)c1)c1cccc(Cl)c1] | 333.1 |
| 27 | 3-chloro-N-(3-chloro-5-(1,3-oxazol-5-yl)phenyl)benzenesulfonamide | 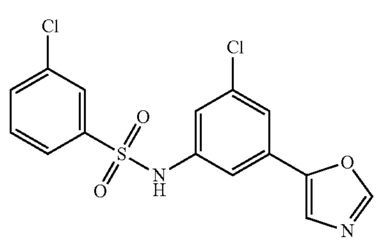 [SMILES: O=S(=O)(Nc1cc(Cl)cc(-c2cnco2)c1)c1cccc(Cl)c1] | 368.9 |

TABLE 1-3-continued

| Example No. | IUPAC Name | Structure | MS |
|---|---|---|---|
| 28 | N-cyclopropyl-3-(1,3-oxazol-5-yl)-5-(trifluoromethyl)benzamide | 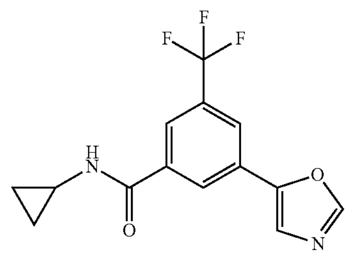 [SMILES: O=C(NC1CC1)c1cc(-c2cnco2)cc(C(F)(F)F)c1] | 294.9 |
| 29 | N-(3-cyano-5-(1,3-oxazol-5-yl)phenyl)cyclopropanecarboxamide | 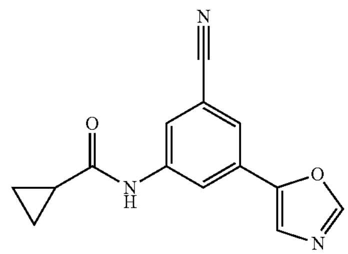 [SMILES: N#Cc1cc(NC(=O)C2CC2)cc(-c2cnco2)c1] | 251.9 |
| 30 | N-(3-cyclopropyl-5-(1,3-oxazol-5-yl)phenyl)cyclopropanecarboxamide | 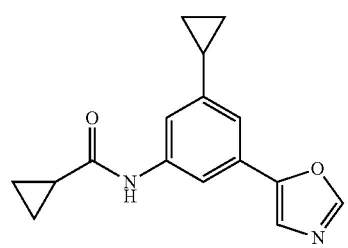 [SMILES: O=C(Nc1cc(-c2cnco2)cc(C2CC2)c1)C1CC1] | 267.0 |

TABLE 1-4

| Example No. | IUPAC Name | Structure | MS |
|---|---|---|---|
| 31 | N-(3-(difluoromethyl)-5-(1,3-oxazol-5-yl)phenyl)cyclopropanecarboxamide | 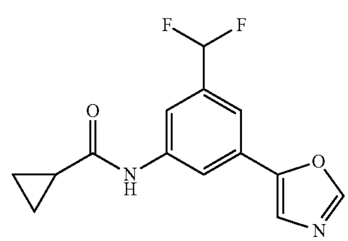 [SMILES: O=C(Nc1cc(-c2cnco2)cc(C(F)F)c1)C1CC1] | 276.9 |
| 32 | 1-(3-(1,3-oxazol-5-yl)-5-(trifluoromethyl)phenyl)piperidin-4-ol | 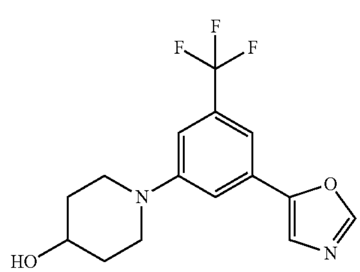 [SMILES: OC1CCN(c2cc(-c3cnco3)cc(C(F)(F)F)c2)CC1] | 313.1 |

TABLE 1-4-continued

| Example No. | IUPAC Name | Structure | MS |
|---|---|---|---|
| 33 | N-(3-chloro-5-(1,3-oxazol-5-yl)phenyl)cyclopropanecarboxamide | 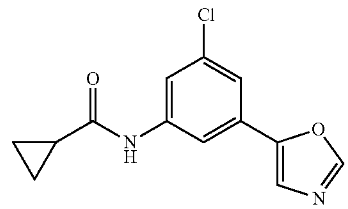 [SMILES: O=C(Nc1cc(Cl)cc(-c2cnco2)c1)C1CC1] | 260.8 |
| 34 | 1-(3-(1,3-oxazol-5-yl)-5-(trifluoromethyl)phenyl)pyridin-2(1H)-one | 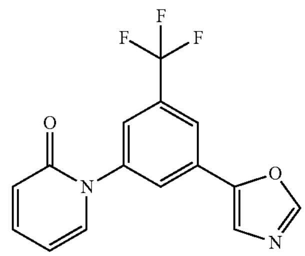 [SMILES: O=c1ccccn1-c1cc(-c2cnco2)cc(C(F)(F)F)c1] | 307.1 |
| 35 | 1-(3-(1,3-oxazol-5-yl)-5-(trifluoromethyl)phenyl)piperidin-2-one | 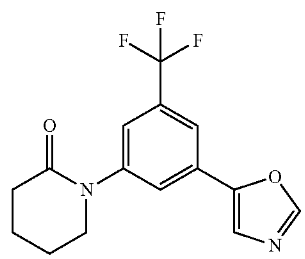 [SMILES: O=C1CCCCN1c1cc(-c2cnco2)cc(C(F)(F)F)c1] | 311.1 |
| 36 | cyclopropyl(4-(1,3-oxazol-5-yl)-6-(trifluoromethyl)-2,3-dihydro-1H-indol-1-yl)methanone | 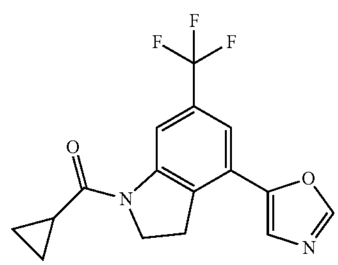 [SMILES: O=C(C1CC1)N1CCc2c(-c3cnco3)cc(C(F)(F)F)cc21] | 323.1 |
| 37 | 1-hydroxy-N-(3-(1,3-oxazol-5-yl)-5-(trifluoromethyl)phenyl)cyclopropanecarboxamide | 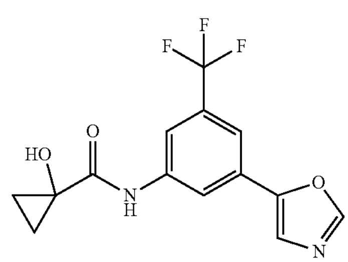 [SMILES: O=C(Nc1cc(-c2cnco2)cc(C(F)(F)F)c1)C1(O)CC1] | 310.9 |
| 38 | 4-(cyclopropylmethyl)-8-(1,3-oxazol-5-yl)-6-(trifluoromethyl)-2H-1,4-benzoxazin-3(4H)-one | 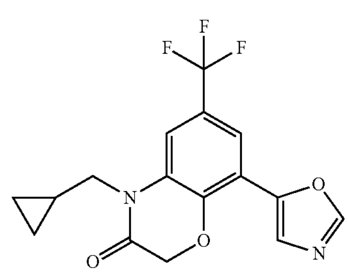 [SMILES: O=C1COc2c(-c3cnco3)cc(C(F)(F)F)cc2N1CC1CC1] | 339.1 |

TABLE 1-4-continued

| Example No. | IUPAC Name | Structure | MS |
|---|---|---|---|
| 39 | 3,3-difluoro-N-(3-(1,3-oxazol-5-yl)-5-(trifluoromethyl)phenyl)cyclobutanecarboxamide | 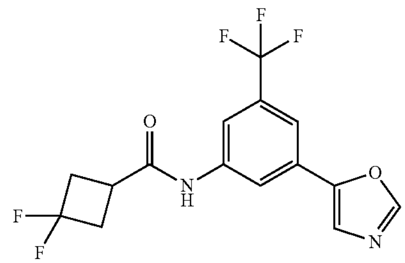 [SMILES: O=C(Nc1cc(-c2cnco2)cc(C(F)(F)F)c1)C1CC(F)(F)C1] | 344.9 |
| 40 | N-(3-(1,3-oxazol-5-yl)-5-(trifluoromethyl)phenyl)oxetane-3-carboxamide | 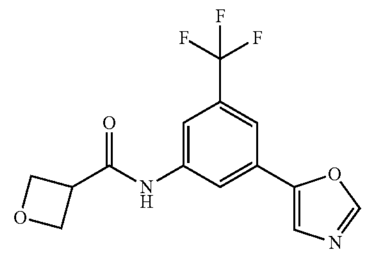 [SMILES: O=C(Nc1cc(-c2cnco2)cc(C(F)(F)F)c1)C1COC1] | 310.9 |

TABLE 1-5

| Example No. | IUPAC Name | Structure | MS |
|---|---|---|---|
| 41 | 3,3,3-trifluoro-N-(3-(1,3-oxazol-5-yl)-5-(trifluoromethyl)phenyl)propanamide | 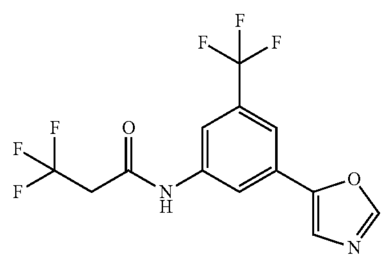 [SMILES: O=C(CC(F)(F)F)Nc1cc(-c2cnco2)cc(C(F)(F)F)c1] | 336.9 |
| 42 | N-(3-(1,3-oxazol-5-yl)-5-(trifluoromethyl)phenyl)-5-oxo-L-prolinamide | 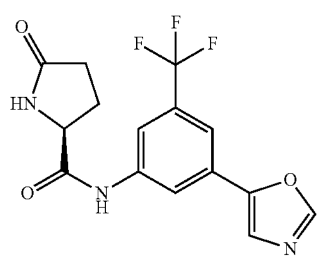 [SMILES: O=C1CC[C@@H](C(=O)Nc2cc(-c3cnco3)cc(C(F)(F)F)c2)N1] | 337.9 |
| 43 | 2-(1H-imidazol-1-yl)-N-(3-(1,3-oxazol-5-yl)-5-(trifluoromethyl)phenyl)acetamide | 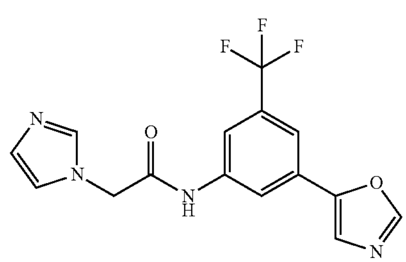 [SMILES: O=C(Cn1ccnc1)Nc1cc(-c2cnco2)cc(C(F)(F)F)c1] | 337.0 |

TABLE 1-5-continued

| Example No. | IUPAC Name | Structure | MS |
|---|---|---|---|
| 44 | 3,3-dimethyl-N-(3-(1,3-oxazol-5-yl)-5-(trifluoromethyl)phenyl)butanamide | 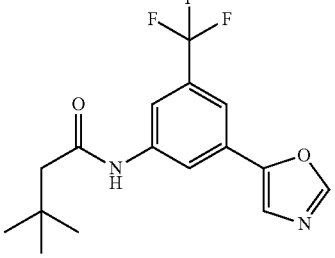 | 324.9 |
| 45 | 4-benzyl-N-(3-(1,3-oxazol-5-yl)-5-(trifluoromethyl)phenyl)morpholine-2-carboxamide | 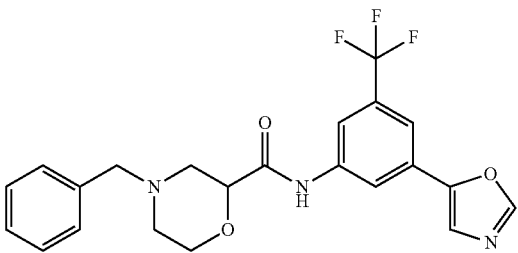 [SMILES: O=C(Nc1cc(-c2cnco2)cc(C(F)(F)F)c1)C1CN(Cc2ccccc2)CCO1] | 432.1 |
| 46 | 2,2-difluoro-N-(3-(1,3-oxazol-5-yl)-5-(trifluoromethyl)phenyl)acetamide | 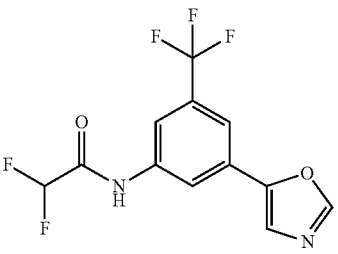 | 304.8 |
| 47 | 1-methyl-N-(3-(1,3-oxazol-5-yl)-5-(trifluoromethyl)phenyl)cyclopropanecarboxamide | 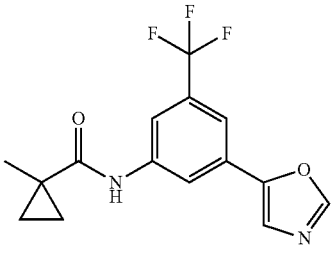 [SMILES: CC1(C(=O)Nc2cc(-c3cnco3)cc(C(F)(F)F)c2)CC1] | 308.9 |
| 48 | 1-cyano-N-(3-(1,3-oxazol-5-yl)-5-(trifluoromethyl)phenyl)cyclopropanecarboxamide | 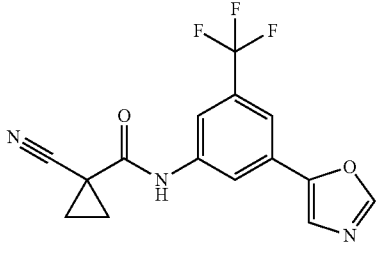 [SMILES: N#CC1(C(=O)Nc2cc(-c3cnco3)cc(C(F)(F)F)c2)CC1] | 319.9 |
| 49 | 2,2-dimethyl-N-(3-(1,3-oxazol-5-yl)-5-(trifluoromethyl)phenyl)cyclopropanecarboxamide | 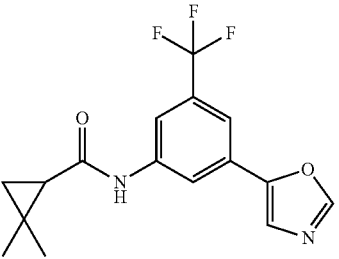 [SMILES: CC1(C)CC1C(=O)Nc1cc(-c2cnco2)cc(C(F)(F)F)c1] | 322.9 |

TABLE 1-5-continued

| Example No. | IUPAC Name | Structure | MS |
|---|---|---|---|
| 50 | 2-cyclopropyl-N-(3-(1,3-oxazol-5-yl)-5-(trifluoromethyl)phenyl)acetamide | 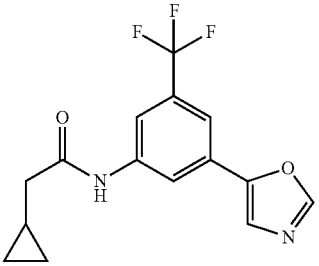 [SMILES: O=C(CC1CC1)Nc1cc(-c2cnco2)cc(C(F)(F)F)c1] | 308.9 |

TABLE 1-6

| Example No. | IUPAC Name | Structure | MS |
|---|---|---|---|
| 51 | 2-(2-furyl)-N-(3-(1,3-oxazol-5-yl)-5-(trifluoromethyl)phenyl)acetamide | 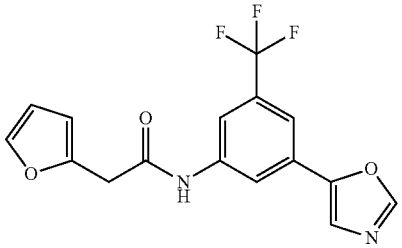 [SMILES: O=C(Cc1ccco1)Nc1cc(-c2cnco2)cc(C(F)(F)F)c1] | 334.9 |
| 52 | 2-(4-fluorophenyl)-N-(3-(1,3-oxazol-5-yl)-5-(trifluoromethyl)phenyl)acetamide | 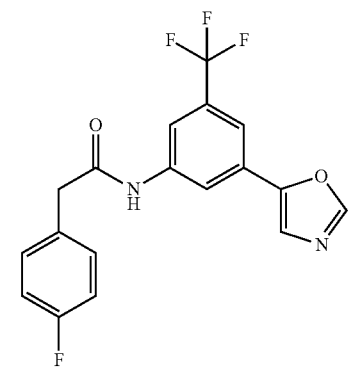 [SMILES: O=C(Cc1ccc(F)cc1)Nc1cc(-c2cnco2)cc(C(F)(F)F)c1] | 363.0 |
| 53 | cyclopropyl(9-(1,3-oxazol-5-yl)-7-(trifluoromethyl)-3,4-dihydro-1,5-benzoxazepin-5(2H)-yl)methanone | 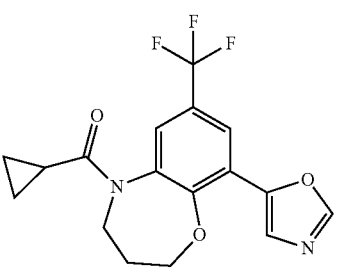 [SMILES: O=C(C1CC1)N1CCCOc2c(-c3cnco3)cc(C(F)(F)F)cc21] | 353.1 |
| 54 | cyclopropyl(8-(1,3-oxazol-5-yl)-6-(trifluoromethyl)-2,3-dihydro-4H-1,4-benzoxazin-4-yl)methanone | 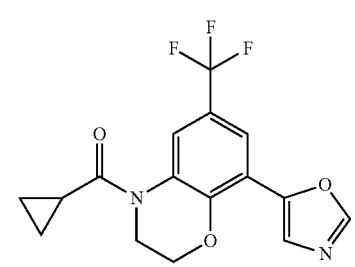 [SMILES: O=C(C1CC1)N1CCOc2c(-c3cnco3)cc(C(F)(F)F)cc21] | 339.1 |

TABLE 1-6-continued

| Example No. | IUPAC Name | Structure | MS |
|---|---|---|---|
| 55 | 5-(3-(1H-imidazol-1-yl)-5-(trifluoromethyl)phenyl)-1,3-oxazole | 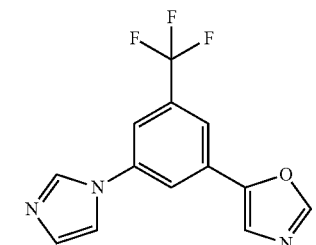 | 280.0 |
| 56 | 3-(1,3-oxazol-5-yl)-N-(pyridin-2-ylmethyl)-5-(trifluoromethyl)aniline | 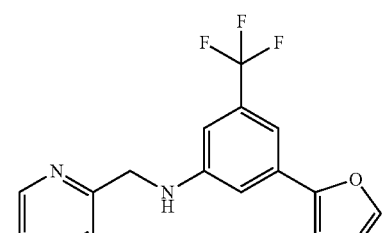 | 320.1 |
| 57 | 3-(1,3-oxazol-5-yl)-N-(pyridin-3-ylmethyl)-5-(trifluoromethyl)aniline | 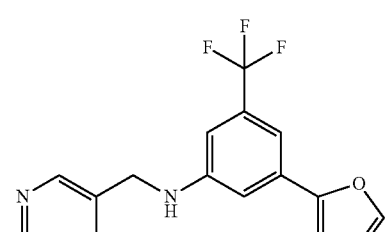 | 320.1 |
| 58 | N-(7-(1,3-oxazol-5-yl)-2,3-dihydro-1-benzofuran-5-yl)cyclopropanecarboxamide | 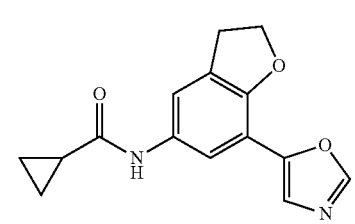 [SMILES: O=C(Nc1cc2c(c(-c3cnco3)c1)OCC2)C1CC1] | 271.0 |
| 59 | N-(7-(1,3-oxazol-5-yl)-2,3-dihydro-1-benzofuran-5-yl)cyclopropanesulfonamide | 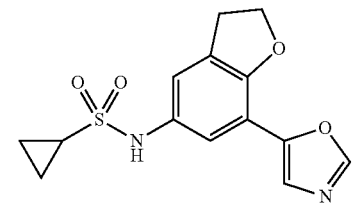 [SMILES: O=S(=O)(Nc1cc2c(c(-c3cnco3)c1)OCC2)C1CC1] | 307.1 |
| 60 | N-(3-(1,3-oxazol-5-yl)-5-(trifluoromethyl)phenyl)cyclopropanesulfonamide | 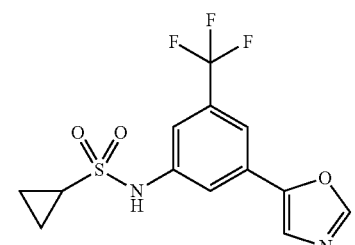 | 333.0 |

TABLE 1-7

| Example No. | IUPAC Name | Structure | MS |
|---|---|---|---|
| 61 | N-(6-(1,3-oxazol-5-yl)-4-(trifluoromethyl)pyridin-2-yl)cyclopropanecarboxamide | 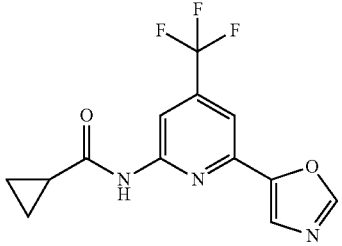 | 298.1 |
| 62 | tert-butyl 8-(1,3-oxazol-5-yl)-6-(trifluoromethyl)-2,3-dihydro-4H-1,4-benzoxazine-4-carboxylate | 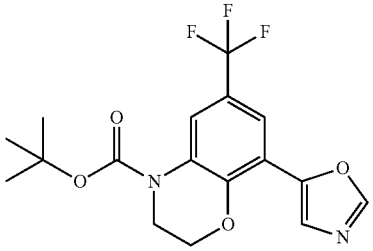 [SMILES: CC(C)(C)OC(=O)N1CCOc2c(-c3cnco3)cc(C(F)(F)F)cc21] | 371.0 |
| 63 | tert-butyl 4-(1,3-oxazol-5-yl)-6-(trifluoromethyl)indoline-1-carboxylate | 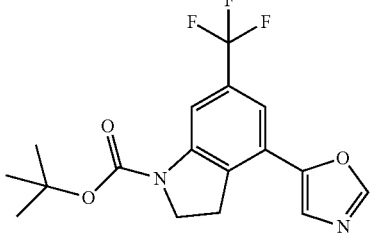 | 355.1 |
| 64 | N-(3-(1,3-oxazol-5-yl)-5-(trifluoromethyl)phenyl)-2-(1H-pyrazol-1-yl)acetamide | 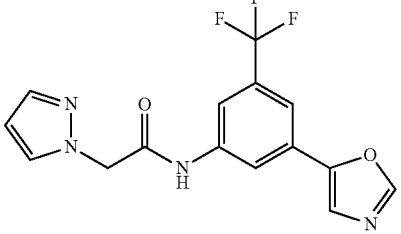 | 334.9 |
| 65 | 6-(1,3-oxazol-5-yl)-N-(pyridin-2-ylmethyl)-4-(trifluoromethyl)pyridin-2-amine | 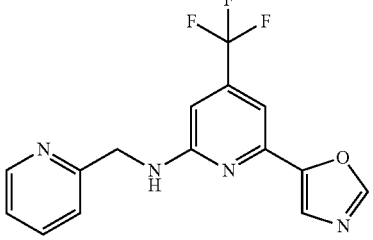 | 321.0 |
| 66 | 7-(1,3-oxazol-5-yl)-N-(pyridin-2-ylmethyl)-2,3-dihydro-1-benzofuran-5-amine | 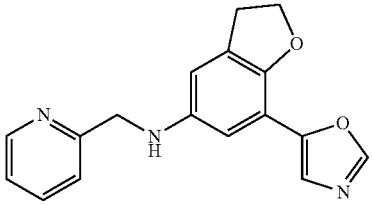 [SMILES: c1ccc(CNc2cc3c(c(-c4cnco4)c2)OCC3)nc1] | 294.1 |

TABLE 1-7-continued

| Example No. | IUPAC Name | Structure | MS |
|---|---|---|---|
| 67 | N-(4-(1,3-oxazol-5-yl)-6-(trifluoromethyl)pyridin-2-yl)cyclopropanecarboxamide | 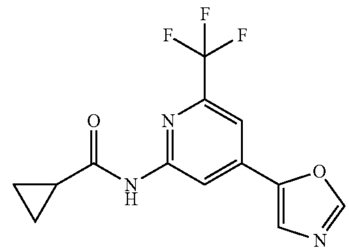 [SMILES: O=C(Nc1cc(-c2cnco2)cc(C(F)(F)F)n1)C1CC1] | 295.9 |
| 68 | N-(6-(1,3-oxazol-5-yl)-4-(trifluoromethyl)pyridin-2-yl)acetamide | 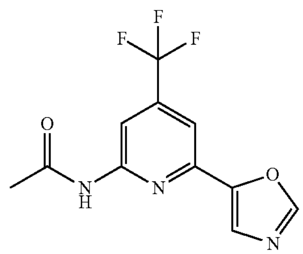 [SMILES: CC(=O)Nc1cc(C(F)(F)F)cc(-c2cnco2)n1] | 269.9 |
| 69 | 2-(1-methyl-1H-pyrazol-3-yl)-N-(3-(1,3-oxazol-5-yl)-5-(trifluoromethyl)phenyl)acetamide | 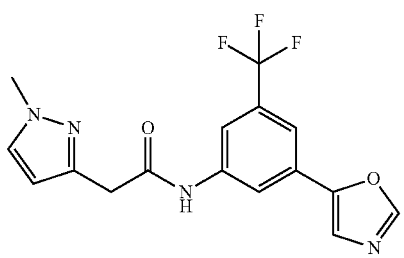 [SMILES: Cn1ccc(CC(=O)Nc2cc(-c3cnco3)cc(C(F)(F)F)c2)n1] | 351.1 |
| 70 | 2-methyl-N-(6-(1,3-oxazol-5-yl)-4-(trifluoromethyl)pyridin-2-yl)propanamide | 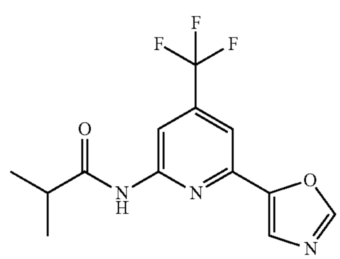 [SMILES: CCC(=O)Nc1cc(C(F)(F)F)cc(-c2cnco2)n1] | 300.1 |

TABLE 1-8

| Example No. | IUPAC Name | Structure | MS |
|---|---|---|---|
| 71 | N-(6-(1,3-oxazol-5-yl)-4-(trifluoromethyl)pyridin-2-yl)propanamide | 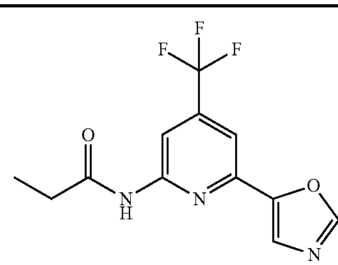 | 284.0 |

TABLE 1-8-continued

| Example No. | IUPAC Name | Structure | MS |
|---|---|---|---|
| 72 | N-(4-(1,3-oxazol-5-yl)-6-(trifluoromethyl)pyridin-2-yl)nicotinamide | 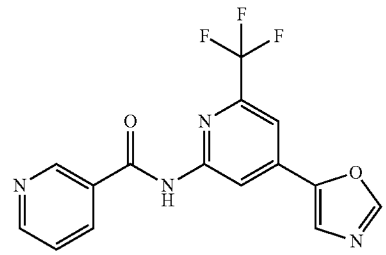 [SMILES: O=C(Nc1cc(-c2cnco2)cc(C(F)(F)F)n1)c1cccnc1] | 335.1 |
| 73 | 1-(4-(1,3-oxazol-5-yl)-6-(trifluoromethyl)-2,3-dihydro-1H-indol-1-yl)propan-1-one | 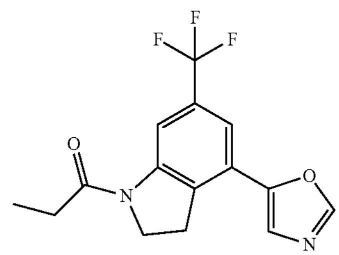 [SMILES: CCC(=O)N1CCc2c(-c3cnco3)cc(C(F)(F)F)cc21] | 311.1 |
| 74 | 1-(4-(1,3-oxazol-5-yl)-6-(trifluoromethyl)-2,3-dihydro-1H-indol-1-yl)ethanone | 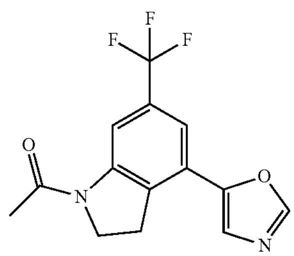 [SMILES: CC(=O)N1CCc2c(-c3cnco3)cc(C(F)(F)F)cc21] | 297.1 |
| 75 | 1-((4-(1,3-oxazol-5-yl)-6-(trifluoromethyl)-2,3-dihydro-1H-indol-1-yl)carbonyl)cyclopropanecarbonitrile | 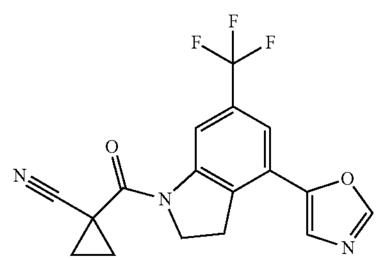 [SMILES: N#CC1(C(=O)N2CCc3c(-c4cnco4)cc(C(F)(F)F)cc32)CC1] | 348.1 |
| 76 | N-(2-(1,3-oxazol-5-yl)-6-(trifluoromethyl)pyridin-4-yl)cyclopropanecarboxamide | 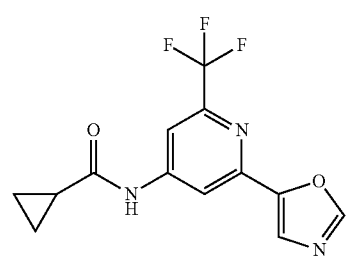 [SMILES: O=C(Nc1cc(-c2cnco2)nc(C(F)(F)F)c1)C1CC1] | 295.9 |
| 77 | cyclopropyl(6-(difluoromethyl)-4-(1,3-oxazol-5-yl)-2,3-dihydro-1H-indol-1-yl)methanone | 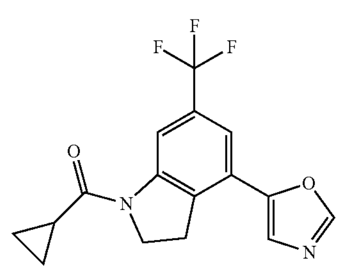 [SMILES: O=C(C1CC1)N1CCc2c(-c3cnco3)cc(C(F)(F)F)cc21] | 305.1 |

TABLE 1-8-continued

| Example No. | IUPAC Name | Structure | MS |
|---|---|---|---|
| 78 | N-(1-methyl-4-(1,3-oxazol-5-yl)-1H-indazol-6-yl)cyclopropanecarboxamide | 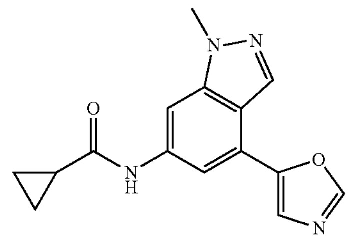 [SMILES: Cn1ncc2c(-c3cnco3)cc(NC(=O)C3CC3)cc21] | 283.1 |
| 79 | N-(1-methyl-4-(1,3-oxazol-5-yl)-1H-indazol-6-yl)cyclopropanesulfonamide | 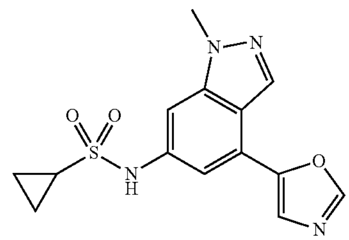 [SMILES: Cn1ncc2c(-c3cnco3)cc(NS(=O)(=O)C3CC3)cc21] | 319.1 |
| 80 | 2-methyl-1-(4-(1,3-oxazol-5-yl)-6-(trifluoromethyl)-2,3-dihydro-1H-indol-1-yl)propan-1-one | 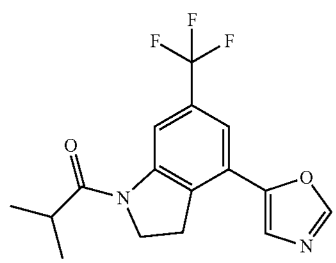 [SMILES: CC(C)C(=O)N1CCc2c(-c3cnco3)cc(C(F)(F)F)cc21] | 325.1 |

TABLE 1-9

| Example No. | IUPAC Name | Structure | MS |
|---|---|---|---|
| 81 | 1-(4-(1,3-oxazol-5-yl)-6-(trifluoromethyl)-2,3-dihydro-1H-indol-1-yl)butan-1-one | 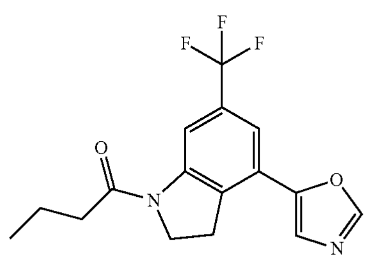 [SMILES: CCCC(=O)N1CCc2c(-c3cnco3)cc(C(F)(F)F)cc21] | 325.1 |
| 82 | N-ethyl-4-(1,3-oxazol-5-yl)-6-(trifluoromethyl)indoline-1-carboxamide | 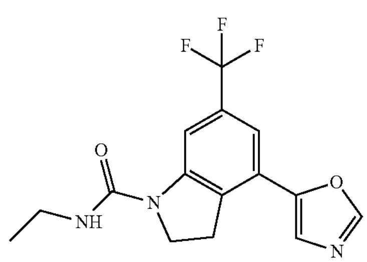 [SMILES: CCNC(=O)N1CCc2c(-c3cnco3)cc(C(F)(F)F)cc21] | 326.1 |

TABLE 1-9-continued

| Example No. | IUPAC Name | Structure | MS |
|---|---|---|---|
| 83 | morpholin-4-yl(4-(1,3-oxazol-5-yl)-6-(trifluoromethyl)-2,3-dihydro-1H-indol-1-yl)methanone | 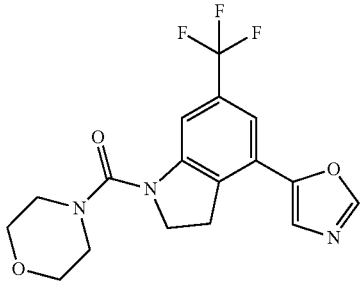 [SMILES: O=C(N1CCOCC1)N1CCc2c(-c3cnco3)cc(C(F)(F)F)cc21] | 368.0 |
| 84 | 1-(3-(1,3-oxazol-5-yl)-5-(trifluoromethyl)phenyl)piperidine | 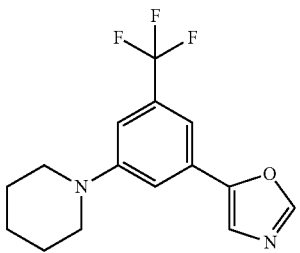 [SMILES: FC(F)(F)c1cc(-c2cnco2)cc(N2CCCCC2)c1] | 297.1 |
| 85 | 4-(3-(1,3-oxazol-5-yl)-5-(trifluoromethyl)phenyl)morpholine | 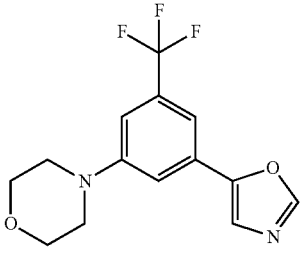 [SMILES: FC(F)(F)c1cc(-c2cnco2)cc(N2CCOCC2)c1] | 299.1 |
| 86 | (4-(1,3-oxazol-5-yl)-6-(trifluoromethyl)-2,3-dihydro-1H-indol-1-yl)(piperidin-1-yl)methanone | 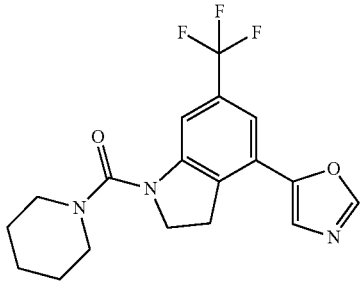 [SMILES: O=C(N1CCCCC1)N1CCc2c(-c3cnco3)cc(C(F)(F)F)cc21] | 366.1 |
| 87 | (4-(1,3-oxazol-5-yl)-6-(trifluoromethyl)-2,3-dihydro-1H-indol-1-yl)(tetrahydro-2H-pyran-4-yl)methanone | 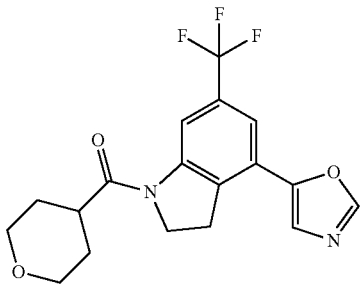 [SMILES: O=C(C1CCOCC1)N1CCc2c(-c3cnco3)cc(C(F)(F)F)cc21] | 367.0 |

TABLE 1-9-continued

| Example No. | IUPAC Name | Structure | MS |
|---|---|---|---|
| 88 | 1-(3-(1,3-oxazol-5-yl)-5-(trifluoromethyl)phenyl)pyrrolidin-3-ol | 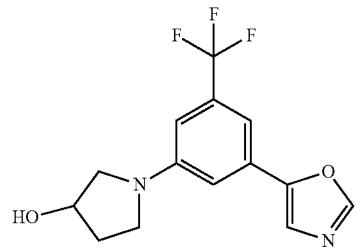 [SMILES: OC1CCN(c2cc(-c3cnco3)cc(C(F)(F)F)c2)C1] | 299.2 |
| 89 | 4,4-difluoro-1-(3-(1,3-oxazol-5-yl)-5-(trifluoromethyl)phenyl)piperidine | 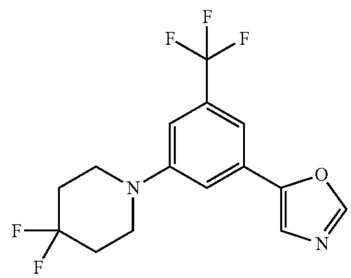 [SMILES: FC1(F)CCN(c2cc(-c3cnco3)cc(C(F)(F)F)c2)CC1] | 333.2 |
| 90 | tert-butyl 4-(3-(1,3-oxazol-5-yl)-5-(trifluoromethyl)phenyl)piperazine-1-carboxylate | 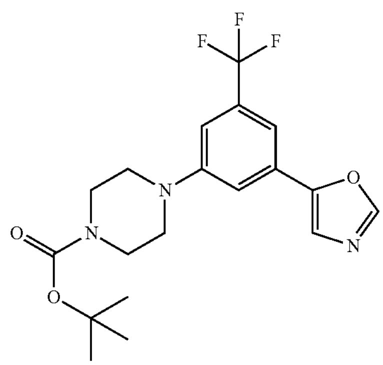 [SMILES: CC(C)(C)OC(=O)N1CCN(c2cc(-c3cnco3)cc(C(F)(F)F)c2)CC1] | 398.0 |

TABLE 1-10

| Example No. | IUPAC Name | Structure | MS |
|---|---|---|---|
| 91 | 4-hydroxy-1-(3-(1,3-oxazol-5-yl)-5-(trifluoromethyl)phenyl)piperidin-2-one | 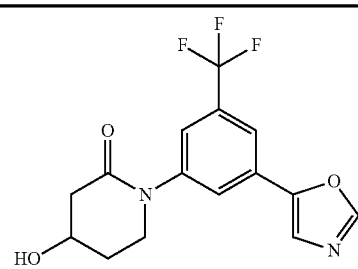 | 327.1 |
| 92 | 4-benzyl-1-(3-(1,3-oxazol-5-yl)-5-(trifluoromethyl)phenyl)piperidin-4-ol | 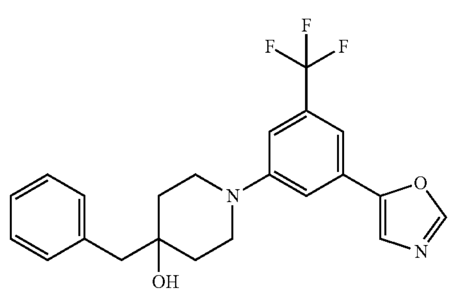 [SMILES: OC1(Cc2ccccc2)CCN(c2cc(-c3cnco3)cc(C(F)(F)F)c2)CC1] | 403.1 |

TABLE 1-10-continued

| Example No. | IUPAC Name | Structure | MS |
|---|---|---|---|
| 93 | (3R)-1-(3-(1,3-oxazol-5-yl)-5-(trifluoromethyl)phenyl)pyrrolidin-3-ol | 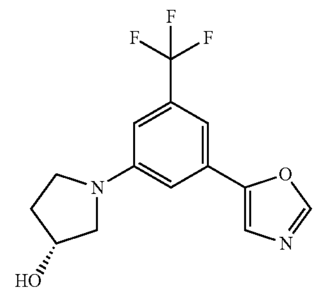 [SMILES: O[C@@H]1CCN(c2cc(-c3cnco3)cc(C(F)(F)F)c2)C1] | 299.2 |
| 94 | (2,6-dimethylmorpholin-4-yl)(4-(1,3-oxazol-5-yl)-6-(trifluoromethyl)-2,3-dihydro-1H-indol-1-yl)methanone | 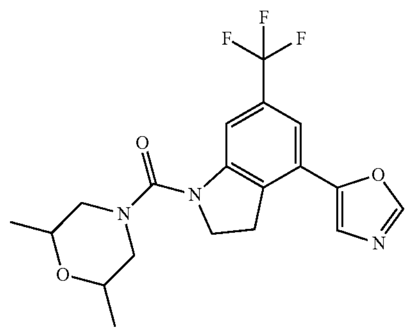 [SMILES: CC1CN(C(=O)N2CCc3c(-c4cnco4)cc(C(F)(F)F)cc32)CC(C)O1] | 396.2 |
| 95 | (3S)-1-(3-(1,3-oxazol-5-yl)-5-(trifluoromethyl)phenyl)pyrrolidin-3-ol | 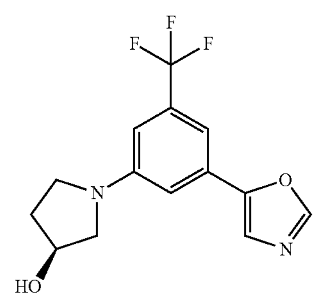 [SMILES: O[C@H]1CCN(c2cc(-c3cnco3)cc(C(F)(F)F)c2)C1] | 299.2 |
| 96 | 1-(6-(1,3-oxazol-5-yl)-4-(trifluoromethyl)pyridin-2-yl)pyrrolidin-3-ol | 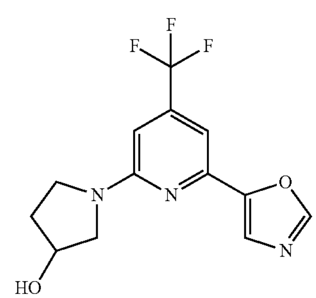 [SMILES: OC1CCN(c2cc(C(F)(F)F)cc(-c3cnco3)n2)C1] | 300.1 |
| 97 | 3-methyl-1-(3-(1,3-oxazol-5-yl)-5-(trifluoromethyl)phenyl)pyrrolidin-3-ol | 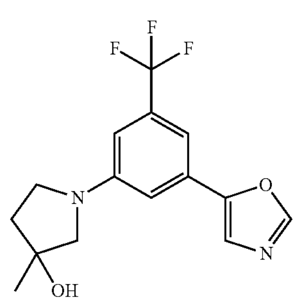 [SMILES: CC1(O)CCN(c2cc(-c3cnco3)cc(C(F)(F)F)c2)C1] | 313.1 |

TABLE 1-10-continued

| Example No. | IUPAC Name | Structure | MS |
|---|---|---|---|
| 98 | 1-(4-methoxybenzyl)-4-(3-(1,3-oxazol-5-yl)-5-(trifluoromethyl)phenyl)piperazine | 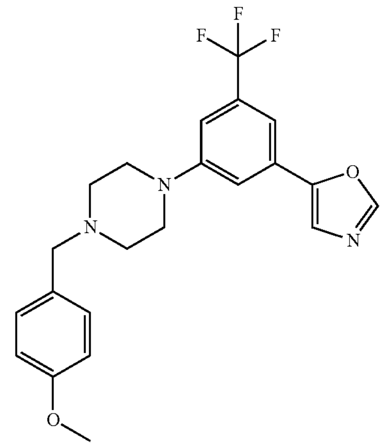 [SMILES: COc1ccc(CN2CCN(c3cc(-c4cnco4)cc(C(F)(F)F)c3)CC2)cc1] | 418.2 |
| 99 | N-(3-(1,3-oxazol-5-yl)-5-(trifluoromethyl)phenyl)tetrahydro-2H-pyran-4-carboxamide | 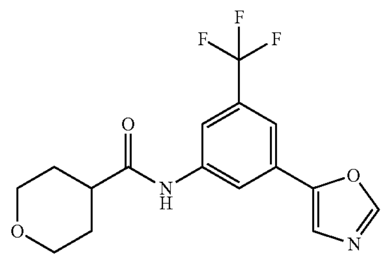 [SMILES: O=C(Nc1cc(-c2cnco2)cc(C(F)(F)F)c1)C1CCOCC1] | 338.9 |
| 100 | 4-benzyl-1-(3-(1,3-oxazol-5-yl)-5-(trifluoromethyl)phenyl)piperidin-3-ol | 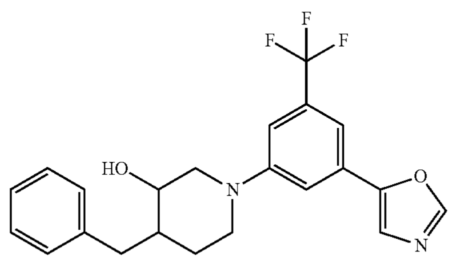 [SMILES: OC1CN(c2cc(-c3cnco3)cc(C(F)(F)F)c2)CCC1Cc1ccccc1] | 403.2 |

TABLE 1-11

| Example No. | IUPAC Name | Structure | MS |
|---|---|---|---|
| 101 | 1-(3-(1,3-oxazol-5-yl)-5-(trifluoromethyl)phenyl)piperidin-4-one | 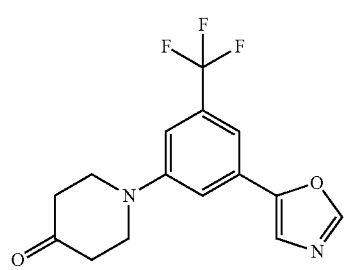 [SMILES: O=C1CCN(c2cc(-c3cnco3)cc(C(F)(F)F)c2)CC1] | 311.1 |

TABLE 1-11-continued

| Example No. | IUPAC Name | Structure | MS |
|---|---|---|---|
| 102 | 3,3-difluoro-N-(3-(1,3-oxazol-5-yl)-5-(trifluoromethyl)phenyl)azetidine-1-carboxamide | 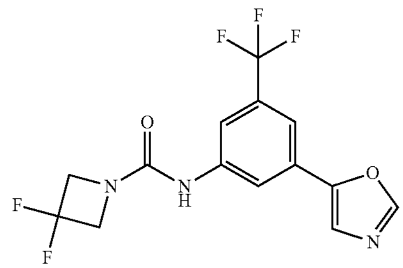 [SMILES: O=C(Nc1cc(-c2cnco2)cc(C(F)(F)F)c1)N1CC(F)(F)C1] | 345.9 |
| 103 | 5-(3-(3-methoxypyrrolidin-1-yl)-5-(trifluoromethyl)phenyl)-1,3-oxazole | 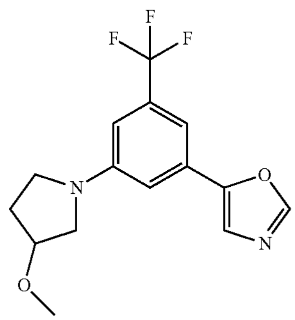 [SMILES: COC1CCN(c2cc(-c3cnco3)cc(C(F)(F)F)c2)C1] | 313.1 |
| 104 | 5-(3-(3,3-difluoropyrrolidin-1-yl)-5-(trifluoromethyl)phenyl)-1,3-oxazole | 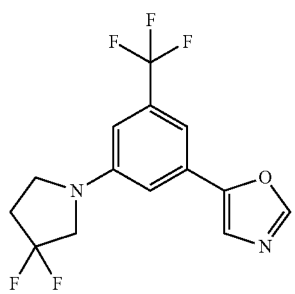 [SMILES: FC1(F)CCN(c2cc(-c3cnco3)cc(C(F)(F)F)c2)C1] | 319.1 |
| 105 | 5-(3-(3-fluoropyrrolidin-1-yl)-5-(trifluoromethyl)phenyl)-1,3-oxazole | 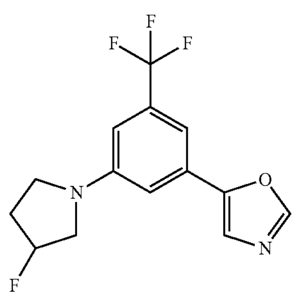 [SMILES: FC1CCN(c2cc(-c3cnco3)cc(C(F)(F)F)c2)C1] | 301.1 |
| 106 | 4-methyl-1-(3-(1,3-oxazol-5-yl)-5-(trifluoromethyl)phenyl)piperidin-4-ol | 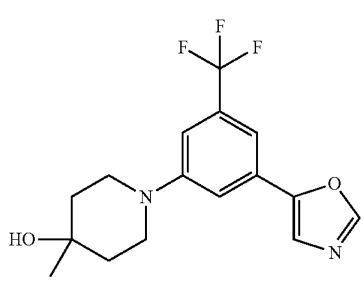 [SMILES: CC1(O)CCN(c2cc(-c3cnco3)cc(C(F)(F)F)c2)CC1] | 327.2 |

TABLE 1-11-continued

| Example No. | IUPAC Name | Structure | MS |
|---|---|---|---|
| 107 | 1-(4-(3-(1,3-oxazol-5-yl)-5-(trifluoromethyl)phenyl)piperazin-1-yl)ethanone | 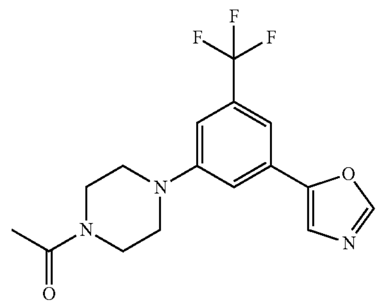 [SMILES: CC(=O)N1CCN(c2cc(-c3cnco3)cc(C(F)(F)F)c2)CC1] | 340.1 |
| 108 | 1-(methylsulfonyl)-4-(3-(1,3-oxazol-5-yl)-5-(trifluoromethyl)phenyl)piperazine | 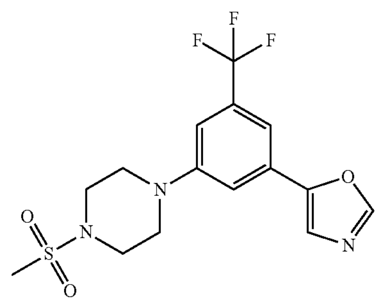 [SMILES: CS(=O)(=O)N1CCN(c2cc(-c3cnco3)cc(C(F)(F)F)c2)CC1] | 376.1 |
| 109 | 1-(2-(1,3-oxazol-5-yl)-6-(trifluoromethyl)pyrimidin-4-yl)pyrrolidin-3-ol | 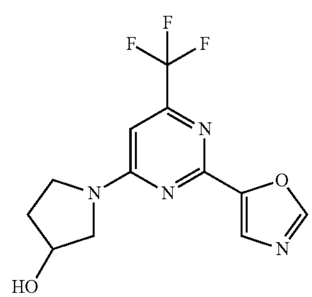 [SMILES: OC1CCN(c2cc(C(F)(F)F)nc(-c3cnco3)n2)C1] | 301.1 |
| 110 | 1-(4-(1,3-oxazol-5-yl)-6-(trifluoromethyl)pyrimidin-2-yl)pyrrolidin-3-ol | 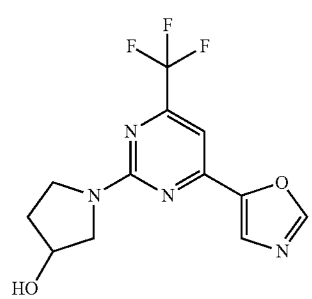 [SMILES: OC1CCN(c2nc(-c3cnco3)cc(C(F)(F)F)n2)C1] | 301.1 |

TABLE 1-12

| Example No. | IUPAC Name | Structure | MS |
|---|---|---|---|
| 111 | 1-(3-(1,3-oxazol-5-yl)-5-(trifluoromethyl)phenyl)pyrrolidin-3-one | 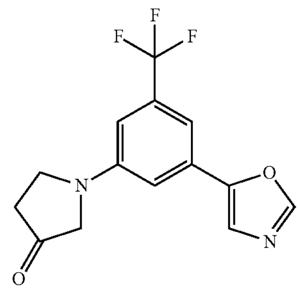 [SMILES: O=C1CCN(c2cc(-c3cnco3)cc(C(F)(F)F)c2)C1] | 294.8 |
| 112 | 5-(3-(3-(henzyloxy)pyrrolidin-1-yl)-5-(trifluoromethyl)phenyl)-1,3-oxazole | 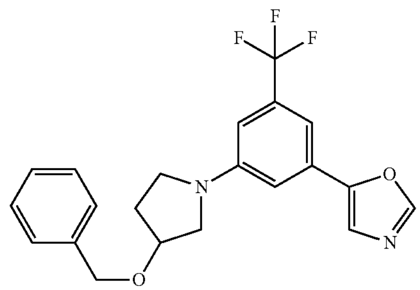 [SMILES: FC(F)(F)c1cc(-c2cnco2)cc(N2CCC(OCc3ccccc3)C2)c1] | 389.2 |
| 113 | 5-(3-(3-methylpyrrolidin-1-yl)-5-(trifluoromethyl)phenyl)-1,3-oxazole | 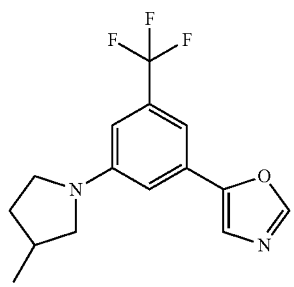 [SMILES: CC1CCN(c2cc(-c3cnco3)cc(C(F)(F)F)c2)C1] | 297.2 |
| 114 | 5-(3-((3S)-3-methoxypyrrolidin-1-yl)-5-(trifluoromethyl)phenyl)-1,3-oxazole | 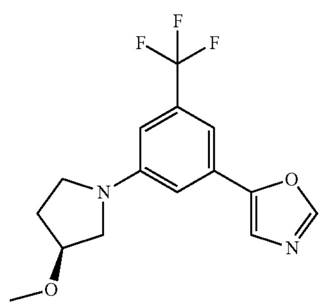 [SMILES: CO[C@H]1CCN(c2cc(-c3cnco3)cc(C(F)(F)F)c2)C1] | 313.1 |
| 115 | 5-(3-((3R)-3-methoxypyrrolidin-1-yl)-5-(trifluoromethyl)phenyl)-1,3-oxazole | 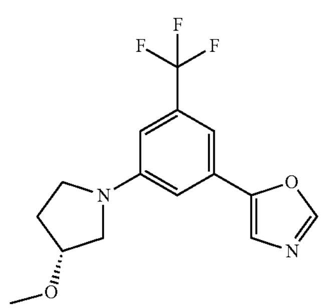 [SMILES: CO[C@@H]1CCN(c2cc(-c3cnco3)cc(C(F)(F)F)c2)C1] | 313.1 |

TABLE 1-12-continued

| Example No. | IUPAC Name | Structure | MS |
|---|---|---|---|
| 116 | 5-(3-(3-methoxy-3-methylpyrrolidin-1-yl)-5-(trifluoromethyl)phenyl)-1,3-oxazole | 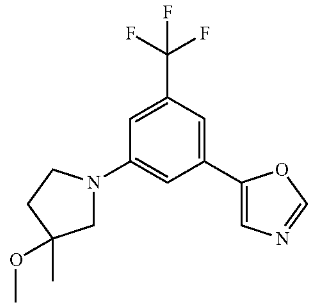 [SMILES: COC1(C)CCN(c2cc(-c3cnco3)cc(C(F)(F)F)c2)C1] | 327.2 |
| 117 | 2-(3-methoxypyrrolidin-1-yl)-6-(1,3-oxazol-5-yl)-4-(trifluoromethyl)pyridine | 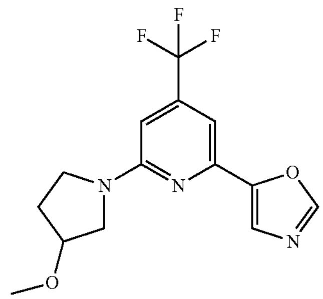 [SMILES: COC1CCN(c2cc(C(F)(F)F)cc(-c3cnco3)n2)C1] | 314.2 |
| 118 | 4-ethyl-1-(3-(1,3-oxazol-5-yl)-5-(trifluoromethyl)phenyl)piperidin-4-ol | 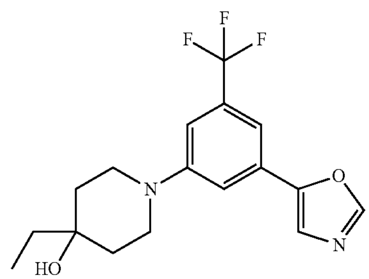 [SMILES: CCC1(O)CCN(c2cc(-c3cnco3)cc(C(F)(F)F)c2)CC1] | 341.1 |
| 119 | N-(1-(3-(1,3-oxazol-5-yl)-5-(trifluoromethyl)phenyl)pyrrolidin-3-yl)methanesulfonamide | 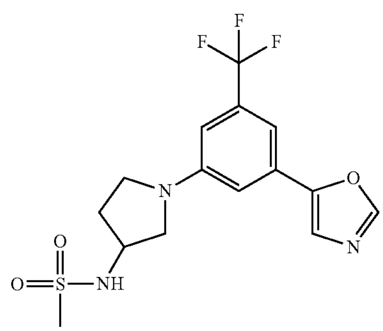 [SMILES: CS(=O)(=O)NC1CCN(c2cc(-c3cnco3)cc(C(F)(F)F)c2)C1] | 376.1 |
| 120 | N-(1-(3-(1,3-oxazol-5-yl)-5-(trifluoromethyl)phenyl)pyrrolidin-3-yl)acetamide | 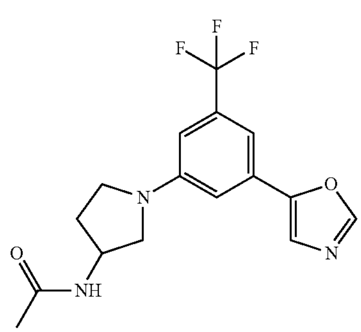 [SMILES: CC(=O)NC1CCN(c2cc(-c3cnco3)cc(C(F)(F)F)c2)C1] | 340.1 |

TABLE 1-13

| Example No. | IUPAC Name | Structure | MS |
|---|---|---|---|
| 121 | 1-(6-(1,3-oxazol-5-yl)-4-(trifluoromethyl)pyridin-2-yl)piperidin-4-ol | 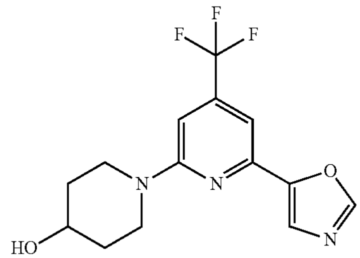 [SMILES: OC1CCN(c2cc(C(F)(F)F)cc(-c3cnco3)n2)CC1] | 314.2 |
| 122 | 2-(3-azidopyrrolidin-1-yl)-6-(1,3-oxazol-5-yl)-4-(trifluoromethyl)pyridine | 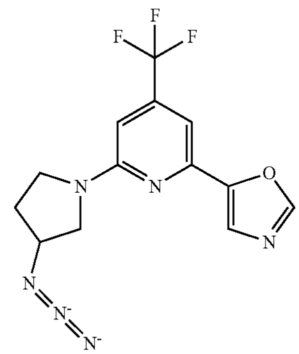 | 325.1 |
| 123 | 2-(4-methoxypiperidin-1-yl)-6-(1,3-oxazol-5-yl)-4-(trifluoromethyl)pyridine | 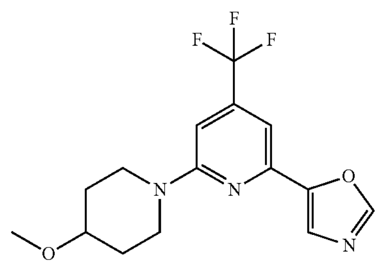 [SMILES: COC1CCN(c2cc(C(F)(F)F)cc(-c3cnco3)n2)CC1] | 328.2 |
| 124 | N-(1-(6-(1,3-oxazol-5-yl)-4-(trifluoromethyl)pyridin-2-yl)pyrrolidin-3-yl)methanesulfonamide | 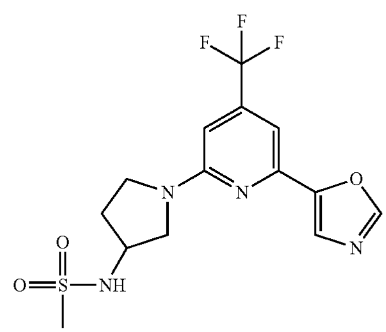 [SMILES: CS(=O)(=O)NC1CCN(c2cc(C(F)(F)F)cc(-c3cnco3)n2)C1] | 377.1 |
| 125 | N-(1-(6-(1,3-oxazol-5-yl)-4-(trifluoromethyl)pyridin-2-yl)pyrrolidin-3-yl)acetamide | 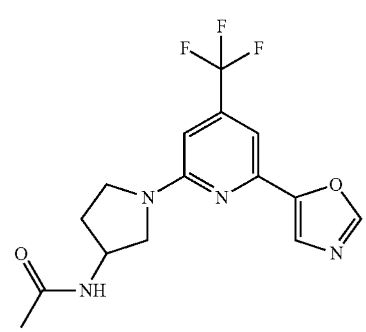 [SMILES: CC(=O)NC1CCN(c2cc(C(F)(F)F)cc(-c3cnco3)n2)C1] | 341.1 |

TABLE 1-13-continued

| Example No. | IUPAC Name | Structure | MS |
|---|---|---|---|
| 126 | (1S,4S)-5-(6-(1,3-oxazol-5-yl)-4-(trifluoromethyl)pyridin-2-yl)-2-oxa-5-azabicyclo[2.2.1]heptane | 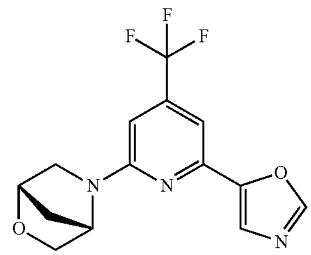 [SMILES: FC(F)(F)c1cc(-c2cnco2)nc(N2C[C@@H]3C[C@H]2CO3)c1] | 312.2 |
| 127 | 3,3-dimethyl-1-(3-(1,3-oxazol-5-yl)-5-(trifluoromethyl)phenyl)pyrrolidin-2-one | 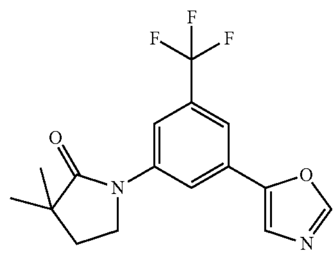 [SMILES: CC1(C)CCN(c2cc(-c3cnco3)cc(C(F)(F)F)c2)C1=O] | 325.2 |
| 128 | (1S,4S)-2-oxa-5-azabicyclo[2.2.1]hept-5-yl(4-(1,3-oxazol-5-yl)-6-(trifluoromethyl)-2,3-dihydro-1H-indol-1-yl)methanone | 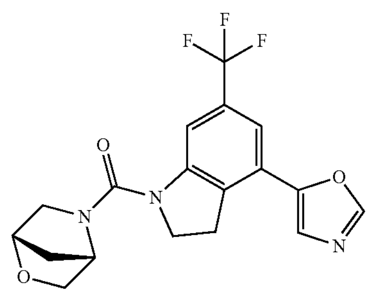 [SMILES: O=C(N1CCc2c(-c3cnco3)cc(C(F)(F)F)cc21)N1C[C@@H]2C[C@H]1CO2] | 380.1 |
| 129 | 3-oxa-6-azabicyclo[3.1.1]hept-6-yl(4-(1,3-oxazol-5-yl)-6-(trifluoromethyl)-2,3-dihydro-1H-indol-1-yl)methanone | 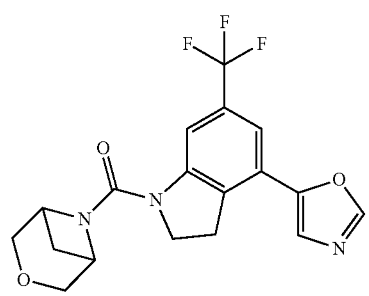 [SMILES: O=C(N1CCc2c(-c3cnco3)cc(C(F)(F)F)cc21)N1C2COCC1C2] | 380.2 |
| 130 | 3-oxa-8-azabicyclo[3.2.1]oct-8-yl(4-(1,3-oxazol-5-yl)-6-(trifluoromethyl)-2,3-dihydro-1H-indol-1-yl)methanone | 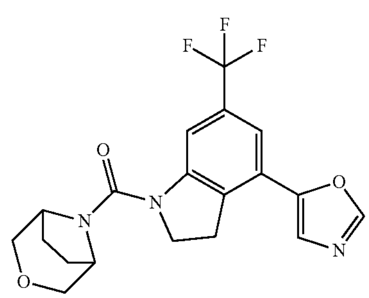 [SMILES: O=C(N1CCc2c(-c3cnco3)cc(C(F)(F)F)cc21)N1C2CCC1COC2] | 394.2 |

TABLE 1-14

| Example No. | IUPAC Name | Structure | MS |
|---|---|---|---|
| 131 | 4,4-dimethyl-1-(3-(1,3-ozazol-5-yl)-5-(trifluoromethyl)phenyl)pyrrolidin-2-one | 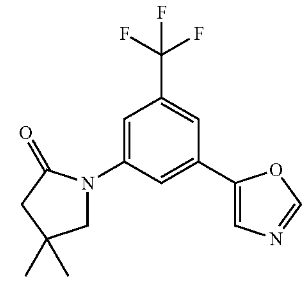 [SMILES: CC1(C)CC(=O)N(c2cc(-c3cnco3)cc(C(F)(F)F)c2)C1] | 325.1 |
| 132 | 4-methyl-1-(3-(1,3-ozazol-5-yl)-5-(trifluoromethyl)phenyl)pyridin-2(1H)-one | 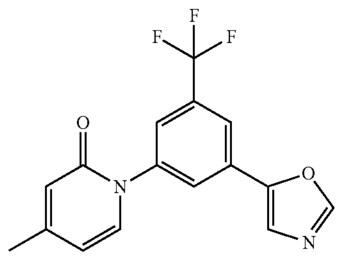 [SMILES: Cc1ccn(-c2cc(-c3cnco3)cc(C(F)(F)F)c2)c(=O)c1] | 321.1 |
| 133 | 4-methyl-1-(3-(1,3-ozazol-5-yl)-5-(trifluoromethyl)phenyl)piperidin-2-one | 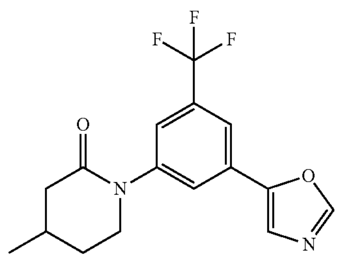 [SMILES: CC1CCN(c2cc(-c3cnco3)cc(C(F)(F)F)c2)C(=O)C1] | 325.1 |
| 134 | 3,3-dimethyl-1-(6-(1,3-ozazol-5-yl)-4-(trifluoromethyl)pyridin-2-yl)pyrrolidin-2-one | 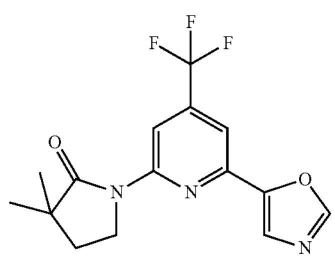 [SMILES: CC1(C)CCN(c2cc(C(F)(F)F)cc(-c3cnco3)n2)C1=O] | 326.2 |
| 135 | 1-(6-(1,3-ozazol-5-yl)-4-(trifluoromethyl)pyridin-2-yl)pyrrolidin-2-one | 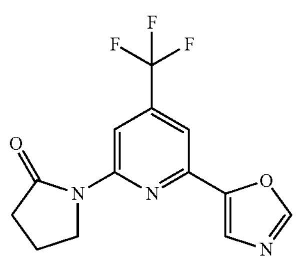 [SMILES: O=C1CCCN1c1cc(C(F)(F)F)cc(-c2cnco2)n1] | 298.1 |

TABLE 1-14-continued

| Example No. | IUPAC Name | Structure | MS |
|---|---|---|---|
| 136 | 4-hydroxy-1-(3-(1,3-ozazol-5-yl)-5-(trifluoromethyl)phenyl)pyrrolidin-2-one | 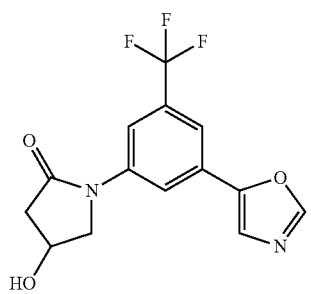 [SMILES: O=C1CC(O)CN1c1cc(-c2cnco2)cc(C(F)(F)F)c1] | 310.8 |
| 137 | 4-(6-(1,3-ozazol-5-yl)-4-(trifluoromethyl)pyridin-2-yl)morpholin-3-one | 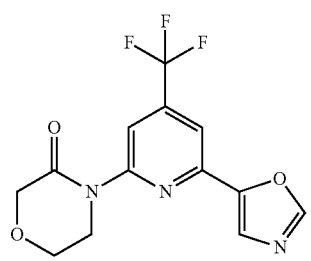 [SMILES: O=C1COCCN1c1cc(C(F)(F)F)cc(-c2cnco2)n1] | 314.2 |
| 138 | 1-methyl-3-(6-(1,3-ozazol-5-yl)-4-(trifluoromethyl)pyridin-2-yl)imidazolidin-2-one | 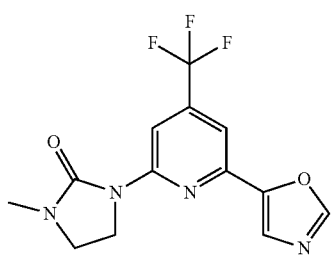 [SMILES: CN1CCN(c2cc(C(F)(F)F)cc(-c3cnco3)n2)C1=O] | 313.1 |
| 139 | optically active 4-methyl-1-(3-(1,3-ozazol-5-yl)-5-(trifluoromethyl)phenyl)piperidin-2-one | 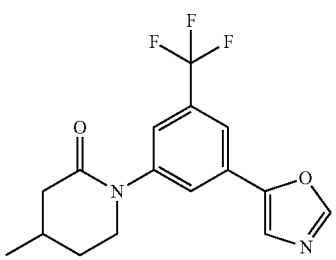 [SMILES: CC1CCN(c2cc(-c3cnco3)cc(C(F)(F)F)c2)C(=O)C1] | 325.1 |
| 140 | optically active 4-methyl-1-(3-(1,3-ozazol-5-yl)-5-(trifluoromethyl)phenyl)piperidin-2-one | 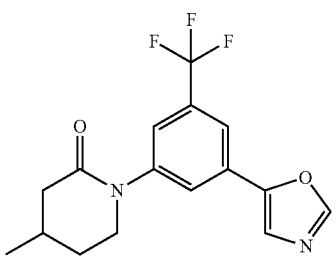 [SMILES: CC1CCN(c2cc(-c3cnco3)cc(C(F)(F)F)c2)C(=O)C1] | 325.1 |

TABLE 1-15

| Example No. | IUPAC Name | Structure | MS |
|---|---|---|---|
| 141 | N-(3-(1,3-oxazol-5-yl)-5-(trifluoromethyl)phenyl)cyclobutane carboxamide | 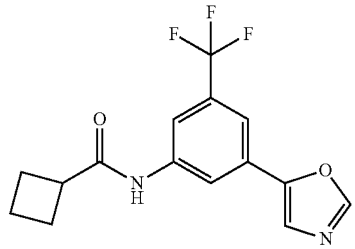 [SMILES: O=C(Nc1cc(-c2cnco2)cc(C(F)(F)F)c1)C1CCC1] | 309.0 |

Formulation Example 1

Production of Capsule

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Construction of Human CH24H (CYP46) Expression Vector

A plasmid DNA for expressing human CH24H in a FreeStyle 293 cell was produced as follows. Using Full-Length Mammalian Gene Collection No. 4819975 (Invitrogen) as a template, and the following two kinds of synthesized DNAs: 5'-GCCCCGGAGCCATGAGCCCCGGGCTG-3' (SEQ ID NO: 1) and 5'-GTCCTGCCTGGAGGCCCCCTCAGCAG-3' (SEQ ID NO: 2), PCR was performed to amplify 91-1625 bp region of human CH24H (BC022539). The obtained fragment was cloned using TOPO TA Cloning Kit (Invitrogen). The obtained fragment was subcloned to pcDNA3.1(+) digested with BamHI and XhoI to give a plasmid DNA for human CH24H expression (pcDNA3.1(+)/hCH24H).

Experimental Example 2

Expression of Human CH24H and Preparation of Human CH24H Lysate

The expression of human CH24H was performed using FreeStyle 293 Expression System (Invitrogen). According to the manual attached to FreeStyle 293 Expression System and using the plasmid DNA for human CH24H expression (pcDNA3.1(+)/hCH24H) constructed in Experimental Example 1, a transient expression using FreeStyle 293-F cell was performed. After transfection, the cells were cultured at 37° C., 8% $CO_2$ with shaking at 125 rpm for 2 days. The cells were collected by centrifugation, and suspended in a suspension buffer (100 mM potassium phosphate (pH 7.4), 0.1 mM EDTA, 1 mM DTT, 20% Glycerol). The suspended product was disrupted by a polytron homogenizer (manufactured by Kinematica), and centrifuged at 9000×g for 10 min, and the supernatant was collected. The collected supernatant was cryopreserved (−80° C.) as a human CH24H lysate standard product.

Experimental Example 3

Measurement of CH24H Inhibitory Activity

For the measurement of CH24H inhibitory activity, using the human CH24H lysate prepared in Experimental Example 2, the amount of 24-HC produced from cholesterol by catalytic activity of CH24H was measured in the presence of a test compound, and compared with that measured in the absence of the test compound. That is, a test compound solution at various concentrations was mixed with a reaction buffer (50 mM potassium phosphate containing 0.1% BSA and Complete, EDTA-free, pH 7.4) and human CH24H lysate. Then, [$^{14}$C] cholesterol (53 mCi/mmol specific activity, 15 μM) was added, and CH24H reaction was performed at 37° C. for 5 hr. After completion of the reaction, a quenching solution consisting of chloroform/methanol/distilled water (2:2:1 v/v) was added, and the resulting 24-HC was extracted by shaking. The extract was applied to silica gel thin layer chromatography (ethyl acetate:toluene=4:6), and the obtained $^{14}$C-24HC fraction was measured with BAS2500 (Fujifilm Corporation).

The inhibitory rate (%) was calculated from the ratio of radioactivity in the presence of a test compound relative to the radioactivity in the absence of the test compound. The results are shown in the following Table 2.

TABLE 2

| Test Compound | Inhibitory Rate in 1 μM (%) |
| --- | --- |
| Example 1 | 89 |
| Example 4 | 89 |
| Example 5 | 79 |
| Example 10 | 83 |
| Example 17 | 89 |
| Example 31 | 90 |
| Example 36 | 92 |
| Example 43 | 90 |
| Example 53 | 52 |
| Example 54 | 92 |
| Example 56 | 88 |
| Example 58 | 84 |
| Example 61 | 88 |
| Example 80 | 91 |
| Example 83 | 92 |
| Example 87 | 97 |
| Example 89 | 93 |
| Example 92 | 89 |
| Example 95 | 96 |
| Example 96 | 91 |
| Example 100 | 97 |
| Example 107 | 91 |
| Example 119 | 95 |
| Example 127 | 91 |
| Example 128 | 97 |
| Example 134 | 89 |

Experimental Example 4

Quantification Test of 24-HC

Animals used were 6-week-old female C57BL/6N mice (3 mice/group). A test compound was suspended in a 0.5% aqueous methylcellulose [133-14255 WAKO] solution (1 mg/mL). The body weight of the mice was measured, and the solution was forcibly administered orally and repeatedly once a day for 3 days. At 16 hours after the third administration, half of the brain was harvested, and the amount of 24-HC was measured.

The wet weight of the brain was measured, and the brain was homogenized with 4-fold amount of saline. This solution was used as a brain extract. The 24-HC in the brain extract was extracted with an acetonitrile solution (98% acetonitrile, 1.98% methanol, 0.02% formic acid), and quantified by HPLC. The average value of 24-HC amount was calculated and the results are shown in relative values with the control group as 100%. The results are shown in the following Table 3.

TABLE 3

| Test Compound | Decreasing Rate in 10 mg/kg (%) | Decreasing Rate in 30 mg/kg (%) |
| --- | --- | --- |
| Example 17 | 80 | |
| Example 36 | 73 | |
| Example 87 | | 56 |
| Example 95 | | 66 |

INDUSTRIAL APPLICABILITY

The compound of the present invention has a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

This application is based on patent application No. 2013-079024 filed on Apr. 4, 2013 in Japan, the contents of which are encompassed in full herein.

The invention claimed is:
1. A compound represented by the formula (I):

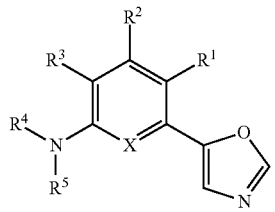

wherein
X is a nitrogen atom or $CR^6$;
$R^1$ is a hydrogen atom;
$R^2$ is
(1) a halogen atom,
(2) a cyano group,
(3) a $C_{1-6}$ alkyl group optionally substituted by 1 to 3 halogen atoms, or
(4) a $C_{3-8}$ cycloalkyl group; or
$R^1$ and $R^2$ in combination optionally form a dihydrofuran ring or a pyrazole ring, each optionally further substituted by $C_{1-6}$ alkyl group(s);
$R^3$ is a hydrogen atom;
$R^4$ is
(1) a $C_{1-6}$ alkyl group optionally substituted by 1 to 3 substituents selected from
  (a) a $C_{3-8}$ cycloalkyl group, and
  (b) a pyridyl group,
(2) a $C_{1-6}$ alkyl-carbonyl group optionally substituted by 1 to 3 substituents selected from
  (a) a halogen atom,
  (b) a $C_{3-8}$ cycloalkyl group,
  (c) a $C_{1-6}$ alkoxy group,
  (d) a $C_{6-14}$ aryl group optionally substituted by 1 to 3 halogen atoms, and
  (e) an imidazolyl group, a pyrazolyl group and a furyl group, each optionally substituted by 1 to 3 $C_{1-6}$ alkyl groups,
(3) a $C_{1-6}$ alkoxy-carbonyl group,
(4) a $C_{3-8}$ cycloalkyl-carbonyl group optionally substituted by 1 to 3 substituents selected from
  (a) a hydroxy group,
  (b) a halogen atom,
  (c) a cyano group, and
  (d) a $C_{1-6}$ alkyl group,
(5) a $C_{6-14}$ aryl-carbonyl group optionally substituted by 1 to 3 substituents selected from
  (a) a halogen atom, and
  (b) a $C_{1-6}$ alkoxy group,
(6) an azetidinylcarbonyl group, an oxetanylcarbonyl group, a pyrrolidinylcarbonyl group, a thienylcarbonyl group, a furylcarbonyl group, a piperidylcarbonyl group, a pyridylcarbonyl group, a morpholinylcarbonyl group, a tetrahydropyranylcarbonyl group, a 2-oxa-5-azabicyclo[2.2.1]heptylcarbonyl group, a 3-oxa-6-azabicyclo[3.1.1]heptylcarbonyl group or a 3-oxa-8-azabicyclo[3.2.1]octylcarbonyl group, each optionally substituted by 1 to 3 substituents selected from
  (a) a halogen atom,
  (b) a $C_{1-6}$ alkyl group optionally substituted by 1 to 3 $C_{6-14}$ aryl groups, and
  (c) an oxo group,
(7) a $C_{3-8}$ cycloalkylsulfonyl group,
(8) a $C_{6-14}$ arylsulfonyl group optionally substituted by 1 to 3 halogen atoms, or
(9) a carbamoyl group optionally mono- or di-substituted by $C_{1-6}$ alkyl group(s);
$R^5$ is a hydrogen atom; and
$R^6$ is a hydrogen atom; or
$R^4$ and $R^5$ in combination optionally form a pyrrolidine ring, an imidazolidine ring, a dihydropyridine ring, a piperidine ring, a piperazine ring, a morpholine ring or a 2-oxa-5-azabicyclo[2.2.1]heptane ring, each optionally substituted by 1 to 3 substituents selected from
(1) a hydroxy group,
(2) a halogen atom,
(3) a $C_{1-6}$ alkyl group optionally substituted by $C_{6-14}$ aryl group(s) optionally substituted by 1 to 3 $C_{1-6}$ alkoxy groups,
(4) a $C_{1-6}$ alkoxy group optionally substituted by 1 to 3 $C_{6-14}$ aryl groups,
(5) a $C_{1-6}$ alkyl-carbonyl group,
(6) a $C_{1-6}$ alkoxy-carbonyl group,
(7) a $C_{1-6}$ alkylsulfonyl group,
(8) an amino group optionally mono- or di-substituted by substituent(s) selected from
  (a) a $C_{1-6}$ alkyl-carbonyl group, and
  (b) a $C_{1-6}$ alkylsulfonyl group,
(9) an azido group, and
(10) an oxo group; or
$R^5$ and $R^6$ in combination optionally form a dihydropyrrole ring, a dihydrooxazine ring or a tetrahydrooxazepine ring, each optionally substituted by one oxo group.

2. The compound or salt of claim 1, wherein
X is a nitrogen atom or $CR^6$;
$R^1$ is a hydrogen atom;
$R^2$ is
(1) a halogen atom,
(2) a cyano group,
(3) a $C_{1-6}$ alkyl group optionally substituted by 1 to 3 halogen atoms, or
(4) a cyclopropyl group; or
$R^1$ and $R^2$ in combination optionally form a dihydrofuran ring or a pyrazole ring, each optionally further substituted by $C_{1-6}$ alkyl group(s);
$R^3$ is a hydrogen atom;
$R^4$ is
(1) a $C_{1-6}$ alkyl group optionally substituted by 1 to 3 substituents selected from
  (a) a cyclopropyl group, and
  (b) a pyridyl group,
(2) a $C_{1-6}$ alkyl-carbonyl group optionally substituted by 1 to 3 substituents selected from
  (a) a halogen atom,
  (b) a cyclopropyl group,
  (c) a $C_{1-6}$ alkoxy group,
  (d) a phenyl group optionally substituted by 1 to 3 halogen atoms, and
  (e) an imidazolyl group, a pyrazolyl group and a furyl group, each optionally substituted by 1 to 3 $C_{1-6}$ alkyl groups,
(3) a $C_{1-6}$ alkoxy-carbonyl group,
(4) a cyclopropylcarbonyl group, a cyclobutylcarbonyl group, a cyclopentylcarbonyl group or a cyclohexylcarbonyl group, each optionally substituted by 1 to 3 substituents selected from (a) a hydroxy group,
(b) a halogen atom,
(c) a cyano group, and
(d) a $C_{1-6}$ alkyl group,
(5) a benzoyl group optionally substituted by 1 to 3 substituents selected from
(a) a halogen atom, and
(b) a $C_{1-6}$ alkoxy group,
(6) an azetidinylcarbonyl group, an oxetanylcarbonyl group, a pyrrolidinylcarbonyl group, a thienylcarbonyl group, a furylcarbonyl group, a piperidylcarbonyl group, a pyridylcarbonyl group, a morpholinylcarbonyl group, a tetrahydropyranylcarbonyl group, a 2-oxa-5-azabicyclo[2.2.1]heptylcarbonyl group, a 3-oxa-6-azabicyclo[3.1.1]heptylcarbonyl group or a 3-oxa-8-azabicyclo[3.2.1]octylcarbonyl group, each optionally substituted by 1 to 3 substituents selected from
(a) a halogen atom,
(b) a $C_{1-6}$ alkyl group optionally substituted by 1 to 3 phenyl groups, and
(c) an oxo group,
(7) a cyclopropylsulfonyl group,
(8) a phenylsulfonyl group optionally substituted by 1 to 3 halogen atoms, or
(9) a carbamoyl group optionally mono- or di-substituted by $C_{1-6}$ alkyl group(s);
$R^5$ is a hydrogen atom; and
$R^6$ is a hydrogen atom; or
$R^4$ and $R^5$ in combination optionally form a pyrrolidine ring, an imidazolidine ring, a dihydropyridine ring, a piperidine ring, a piperazine ring, a morpholine ring or a 2-oxa-5-azabicyclo[2.2.1]heptane ring, each optionally substituted by 1 to 3 substituents selected from
(1) a hydroxy group,
(2) a halogen atom,
(3) a $C_{1-6}$ alkyl group optionally substituted by phenyl group(s) optionally substituted by 1 to 3 $C_{1-6}$ alkoxy groups,
(4) a $C_{1-6}$ alkoxy group optionally substituted by 1 to 3 phenyl groups,
(5) a $C_{1-6}$ alkyl-carbonyl group,
(6) a $C_{1-6}$ alkoxy-carbonyl group,
(7) a $C_{1-6}$ alkylsulfonyl group,
(8) an amino group optionally mono- or di-substituted by substituent(s) selected from
(a) a $C_{1-6}$ alkyl-carbonyl group, and
(b) a $C_{1-6}$ alkylsulfonyl group,
(9) an azido group, and
(10) an oxo group; or
$R^5$ and $R^6$ in combination optionally form a dihydropyrrole ring, a dihydrooxazine ring or a tetrahydrooxazepine ring, each optionally substituted by one oxo group.

3. The compound or salt of claim 1, wherein
X is a nitrogen atom or $CR^6$;
$R^1$ is a hydrogen atom;
$R^2$ is a $C_{1-6}$ alkyl group substituted by 1 to 3 halogen atoms;
$R^3$ is a hydrogen atom;
$R^4$ is
(1) a cyclopropylcarbonyl group, or
(2) a tetrahydropyranylcarbonyl group or a morpholinylcarbonyl group;
$R^5$ is a hydrogen atom; and
$R^6$ is a hydrogen atom; or
$R^5$ and $R^6$ in combination optionally form a dihydropyrrole ring.

4. Cyclopropyl(4-(1,3-oxazol-5-yl)-6-(trifluoromethyl)-2,3-dihydro-1H-indol-1-yl)methanone or a salt thereof.

5. N-(6-(1,3-Oxazol-5-yl)-4-(trifluoromethyl)pyridin-2-yl)cyclopropanecarboxamide or a salt thereof.

6. (4-(1,3-Oxazol-5-yl)-6-(trifluoromethyl)-2,3-dihydro-1H-indol-1-yl)(tetrahydro-2H-pyran-4-yl)methanone or a salt thereof.

7. A pharmaceutical composition comprising the compound or salt of claim 1, and a pharmacologically acceptable carrier.

8. A method of inhibiting cholesterol 24-hydroxylase in a mammal, which comprises administering an effective amount of the compound or salt of claim 1 to the mammal.

9. A method for the treatment of epilepsy or neurodegenerative disease in a mammal, which comprises administering an effective amount of the compound or salt of claim 1 to the mammal.

10. The method of claim 9, wherein the neurodegenerative disease is Alzheimer's disease, mild cognitive disorder, Huntington's disease, Parkinson's disease or multiple sclerosis.

* * * * *